US012624363B2

(12) United States Patent
Mattozzi et al.

(10) Patent No.: US 12,624,363 B2
(45) Date of Patent: May 12, 2026

(54) PLASMID ADDICTION SYSTEM TO DRIVE DESIRED GENE EXPRESSION

(71) Applicant: Sumitomo Chemical Company, Limited, Tokyo (JP)

(72) Inventors: Matthew de la Pena Mattozzi, Boston, MA (US); Daniel Kim, Carlisle, MA (US); Sonya Clarkson, Renton, WA (US)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 17/810,373

(22) Filed: Jul. 1, 2022

(65) Prior Publication Data

US 2023/0142094 A1 May 11, 2023

Related U.S. Application Data

(62) Division of application No. 16/036,261, filed on Jul. 16, 2018, now Pat. No. 11,421,239.

(60) Provisional application No. 62/697,531, filed on Jul. 13, 2018, provisional application No. 62/535,596, filed on Jul. 21, 2017.

(51) Int. Cl.
| | |
|---|---|
| *C12P 21/00* | (2006.01) |
| *C12N 15/70* | (2006.01) |
| *C12P 21/02* | (2006.01) |

(52) U.S. Cl.
CPC .............. *C12N 15/70* (2013.01); *C12P 21/00* (2013.01); *C12P 21/02* (2013.01); *C12N 2840/002* (2013.01)

(58) Field of Classification Search
None
See application file for complete search history.

(56) References Cited

U.S. PATENT DOCUMENTS

| | | | |
|---|---|---|---|
| 6,872,547 | B1 | 3/2005 | Curtiss, III |
| 11,421,239 | B2 | 8/2022 | Mattozzi et al. |
| 2007/0015248 | A1 | 1/2007 | Anton et al. |
| 2007/0149766 | A1 | 6/2007 | Mouillac et al. |
| 2015/0361436 | A1 | 12/2015 | Hitchcock et al. |
| 2016/0122788 | A1 * | 5/2016 | Lee ...................... C12N 9/1029 435/193 |
| 2017/0306337 | A1 | 10/2017 | Tabita et al. |

FOREIGN PATENT DOCUMENTS

| | | |
|---|---|---|
| JP | 2000-050888 A | 2/2000 |
| WO | WO 2017/097383 A1 | 6/2017 |

OTHER PUBLICATIONS

Baeshen (Microbial Cell Factories 2014, vol. 13, No. 141, pp. 1-9). (Year: 2014).*
Kimple (Current Protocols in Protein Science 9.9.1-9.923, 2013). (Year: 2013).*
Baba et al., Construction of *Escherichia coli* K-12 in-frame, single-gene knockout mutants: the Keio collection. Mol Syst Biol. 2006;2:2006. 0008. doi: 10.1038/msb4100050. Epub Feb. 21, 2006.
Balbás, Understanding the art of producing protein and nonprotein molecules in *Escherichia coli*. Mol Biotechnol. Nov. 2001;19(3):251-67. doi: 10.1385/MB:19:3:251.
Balbás et al., Plasmid vector pBR322 and its special-purpose derivatives—a review. Gene. 1986;50(1-3):3-40. doi: 10.1016/0378-1119(86)90307-0.
Beck et al., A multifunctional gene (tetR) controls Tn10-encoded tetracycline resistance. J Bacteriol. May 1982;150(2):633-42. doi: 10.1128/jb.150.2.633-642.1982.
Brantl, Antisense RNAs in plasmids: control of replication and maintenance. Plasmid. Nov. 2002;48(3):165-73. doi: 10.1016/s0147-619x(02)00108-7.
Brosius et al., Construction and fine mapping of recombinant plasmids containing the rrnB ribosomal RNA operon of *E. coli*. Plasmid. Jul. 1981;6(1):112-8. doi: 10.1016/0147-619x(81)90058-5.
Chang et al., Construction and characterization of amplifiable multicopy DNA cloning vehicles derived from the P15A cryptic miniplasmid. J Bacteriol. Jun. 1978;134(3):1141-56. doi: 10.1128/jb.134.3.1141-1156.1978.
Choi et al., Novel, versatile, and tightly regulated expression system for *Escherichia coli* strains. Appl Environ Microbiol. Aug. 2010;76(15):5058-66. doi: 10.1128/AEM.00413-10. Epub Jun. 18, 2010.
Cranenburgh et al., *Escherichia coli* strains that allow antibiotic-free plasmid selection and maintenance by repressor titration. Nucleic Acids Res. Mar. 1, 2001;29(5):E26. doi: 10.1093/nar/29.5.e26.
Datsenko et al., One-step inactivation of chromosomal genes in *Escherichia coli* K-12 using PCR products. Proc Natl Acad Sci U S A. Jun. 6, 2000;97(12):6640-5. doi: 10.1073/pnas.120163297.
Deboy et al., Target site selection by Tn7: attTn7 transcription and target activity. J Bacteriol. Jun. 2000;182(11):3310-3. doi: 10.1128/JB.182.11.3310-3313.2000.
Del Solar et al., Replication and Control of Circular Bacterial Plasmids. Microbiolology And Molecular Biology Reviews. 1998; 62(2): 434-64.
Eguchi et al., Complexes formed by complementary RNA stem-loops. Their formations, structures and interaction with ColE1 Rom protein. J Mol Biol. Aug. 20, 1991;220(4):831-42. doi: 10.1016/0022-2836(91)90356-b.
Fu et al., Development of a chromosome-plasmid balanced lethal system for Lactobacillus acidophilus with thyA gene as selective marker. Microbiol Immunol. 2000;44(7):551-6. doi: 10.1111/j.1348-0421.2000.tb02533.x.

(Continued)

*Primary Examiner* — Celine X Qian

(74) *Attorney, Agent, or Firm* — Wolf, Greenfield & Sacks, P.C.

(57) ABSTRACT

The present invention relates to a Plasmid Addiction System for the stabilization of expression plasmids encoding proteins of interest. The invention uses a succinate cycle optimization to ensure the expression of plasmid(s) of interest. By ensuring that plasmids of interest contain genes necessary in the succinate cycle, the system ensures that the passage of the plasmid to daughters and therefore improves the efficiency of production and expression of genes and/or products of interest.

10 Claims, 16 Drawing Sheets

Specification includes a Sequence Listing.

(56) References Cited

OTHER PUBLICATIONS

Funke et al., The baffled microtiter plate: increased oxygen transfer and improved online monitoring in small scale fermentations. Biotechnol Bioeng. Aug. 15, 2009;103(6):1118-28. doi: 10.1002/bit.22341.

Fürste et al., Molecular cloning of the plasmid RP4 primase region in a multi-host-range tacP expression vector. Gene. 1986;48(1):119-31. doi: 10.1016/0378-1119(86)90358-6.

Gerdes et al., Mechanism of post-segregational killing by the hok/sok system of plasmid R1: sok antisense RNA regulates formation of a hok mRNA species correlated with killing of plasmid-free cells. Mol Microbiol. Nov. 1990;4(11):1807-18. doi: 10.1111/j.1365-2958.1990.tb02029.x.

Gerdes et al., Experimental determination and system level analysis of essential genes in *Escherichia coli* MG1655. J Bacteriol. Oct. 2003;185(19):5673-84. doi: 10.1128/JB.185.19.5673-5684.2003.

Hägg et al., A host/plasmid system that is not dependent on antibiotics and antibiotic resistance genes for stable plasmid maintenance in *Escherichia coli*. J Biotechnol. Jul. 1, 2004;111(1):17-30. doi: 10.1016/j.jbiotec.2004.03.010.

Helinski et al., Replication Control and Other Stable Maintenance Mechanisms of Plasmids. American Society for Microbiology Press. 1996; 2295-2324.

Hiszczyńska-Sawicka et al., Effect of integration host factor of Rna Ii synthesis in replication of plasmid containing orip 15A. Plasmid. Sep. 1998;40(2):150-7. doi: 10.1006/plas.1998.1361.

Herring et al., Conditional lethal amber mutations in essential *Escherichia coli* genes. J Bacteriol. May 2004;186(9):2673-81. doi: 10.1128/JB.186.9.2673-2681.2004.

Jensen et al., A Substrate-Dependent Biological Containment System for Pseudonomas Putida Based on the *Escherichia coli* gef Gene. Appl Environ Microbiol. Nov. 1993;59(11):3713-7. doi: 10.1128/aem.59.11.3713-3717.1993.

Knudsen et al., Development and Testing of Improved Suicide Functions for Biological Containment of Bacteria. Appl Environ Microbiol. Mar. 1995;61(3):985-91. doi: 10.1128/aem.61.3.985-991.1995.

Kroll et al., Plasmid Addiction Systems: Perspectives and Applications in Biotechnology. Microb Biotechnol. Nov. 2010;3(6):634-57. doi: 10.1111/j.1751-7915.2010.00170.x.

Kües et al., Replication of plasmids in gram-negative bacteria. Microbiol Rev. Dec. 1989;53(4):491-516. doi: 10.1128/mr.53.4.491-516.1989.

Mairhofer et al., A novel antibiotic free plasmid selection system: advances in safe and efficient DNA therapy. Biotechnol J. Jan. 2008;3(1):83-9. doi: 10.1002/biot.200700141.

Mattozzi et al., Expression of the sub-pathways of the Chloroflexus aurantiacus 3-hydroxypropionate carbon fixation bicycle in *E. coli*: Toward horizontal transfer of autotrophic growth. Metab Eng. Mar. 2013;16:130-9. doi: 10.1016/j.ymben.2013.01.005. Epub Jan. 29, 2013.

Merlin et al., Assessment of quantitative models for plasmid ColEl copy number control. J Mol Biol. Apr. 28, 1995;248(2):211-9. doi: 10.1016/s0022-2836(95)80043-3.

Michel, Gerhard and Dietmar Schomberg; Metabolic Pathways. 2012. John Wiley and Sons, Eds. Poster.

O'Kennedy et al., Effects of fermentation strategy on the characteristics of plasmid DNA production. Biotechnol Appl Biochem. Feb. 2003;37(Pt 1):83-90. doi: 10.1042/ba20020099.

O'Kennedy et al., Effects of growth medium selection on plasmid DNA production and initial processing steps. J Biotechnol. Jan. 21, 2000;76(2-3):175-83. doi: 10.1016/s0168-1656(99)00187- X.

Postle et al., Nucleotide sequence of the repressor gene of the TN10 tetracycline resistance determinant. Nucleic Acids Res. Jun. 25, 1984;12(12):4849-63. doi: 10.1093/nar/12.12.4849.

Pfaffenzeller et al., Using ColE1-derived RNA I for suppression of a bacterially encoded gene: implication for a novel plasmid addiction system. Biotechnol J. Jun. 2006;1(6):675-81. doi: 10.1002/biot.200600017.

Rawlings, Proteic toxin-antitoxin, bacterial plasmid addiction systems and their evolution with special reference to the pas system of pTF-FC2. FEMS Microbiol Lett. Jul. 15, 1999;176(2):269-77. doi: 10.1111/j.1574-6968.1999.tb13672.x.

Reinikainen et al., *Escherichia coli* plasmid production in fermenter. Biotechnol Bioeng. Jan. 20, 1989;33(4):386-93. doi: 10.1002/bit.260330403.

Ronchel et al., Characterization of Cell Lysis in Pseudomonas putida Induced upon Expression of Heterologous Killing Genes. Applied and Environmental Microbiology. 1998; 64(12): 4904-11.

Rosano et al., Recombinant protein expression in *Escherichia coli*: advances and challenges. Front Microbiol. Apr. 17, 2014;5:172. doi: 10.3389/fmicb.2014.00172. eCollection 2014.

Schumacher et al., Bacterial plasmid partition machinery: a minimalist approach to survival. Curr Opin Struct Biol. Feb. 2012;22(1):72-9. doi: 10.1016/j.sbi.2011.11.001. Epub Dec. 6, 2011.

Tomizawa et al., Plasmid ColEl incompatibility determined by interaction of RNA I with primer transcript. Proc Natl Acad Sci U S A. Oct. 1981;78(10):6096-100. doi: 10.1073/pnas.78.10.6096.

Tomizawa, Control of ColEl plasmid replication: the process of binding of RNA I to the primer transcript. Cell. Oct. 1984;38(3):861-70. doi: 10.1016/0092-8674(84)90281-2.

Tomizawa, Control of ColEl plasmid replication: binding of RNA I to RNA II and inhibition of primer formation. Cell. Oct. 10, 1986;47(1):89-97. doi: 10.1016/0092-8674(86)90369-7.

Torres et al., A gene containment strategy based on a restriction-modification system. Environ Microbiol. Oct. 2000;2(5):555-63. doi: 10.1046/j.1462-2920.2000.00138.x.

Vieira et al., The pUC plasmids, an M13mp7-derived system for insertion mutagenesis and sequencing with synthetic universal primers. Gene. Oct. 1982;19(3):259-68. doi: 10.1016/0378-1119(82)90015-4.

Williams et al., Repressor titration: a novel system for selection and stable maintenance of recombinant plasmids. Nucleic Acids Res. May 1, 1998;26(9):2120-4. doi: 10.1093/nar/26.9.2120.

Yu et al., suc AB and sucCD are mutually essential genes in *Escherichia coli*. FEMS Microbiol Lett. Jan. 2006;254(2):245-50. doi: 10.1111/j.1574-6968.2005.00026.x.

Yu et al., An efficient recombination system for chromosome engineering in *Escherichia coli*. Proc Natl Acad Sci U S A. May 23, 2000;97(11):5978-83. doi: 10.1073/pnas.100127597.

* cited by examiner (5829) PfoI
(5608) MluI
(5456) StuI
(5424) NaeI
(6022) PasI (5353) BlpI (5074) ScaI (4827) SbfI
(4761) BstEII (4564) AfeI — sucA (4357) XcmI (3967) HpaI
(3706) AclI
(3450) PacI
(3314) SgrAI
(3120) AvrII RBS
promoter sucD RsrII (683)
terminator DrdI (1200)

pBR322 ori.

pDvK-sucAD
6101 bp

HindIII (2235)

KanR

XmaI (2481)
SmaI (2483)
NruI (2700)
BanII (2706)
DraIII (2891)
EcoRI (3062)

PLASMID ADDICTION SYSTEM TO DRIVE DESIRED GENE EXPRESSION

CROSS-REFERENCE TO RELATED APPLICATIONS

This application is a Division of U.S. application Ser. No. 16/036,261, filed Jul. 16, 2018, entitled "PLASMID ADDICTION SYSTEM TO DRIVE DESIRED GENE EXPRESSION", which claims priority to U.S. Provisional Patent Application No. 62/697531, filed Jul. 13, 2018, entitled PLASMID ADDICTION SYSTEM TO DRIVE DESIRED GENE EXPRESSION, and to U.S. Provisional Patent Application No. 62/535,596, filed Jul. 21, 2017, entitled PLASMID ADDICTION SYSTEM TO DRIVE DESIRED GENE EXPRESSION. The entire contents of these applications are incorporated herein by reference in their entirety.

REFERENCE TO AN ELECTRONIC SEQUENCE LISTING

The contents of the electronic sequence listing (C149770027US02-SEQ-ZJG.xml; Size: 81,435 bytes; and Date of Creation: Jun. 30, 2022) is herein incorporated by reference in its entirety.

FIELD OF THE INVENTION

The field of the invention relates to methods and processes useful in maintaining extrachromosomal elements of interest in a microbial production strain using genes from the succinate pathway to ensure inclusion and expression of the elements in daughter cells. More specifically, it relates to the use of a plasmid addiction system that ensures that modified microbial cells will maintain plasmids carrying genes involved in producing desired expression products.

BACKGROUND OF THE INVENTION

The present invention is directed to a method of manipulating microbial cells in culture to maintain at least one extrachromosomal element of interest containing at least one gene of interest. Typically, this extrachromosomal element is a plasmid, though phages, prophages, phagemids, cosmids, bacterial artificial chromosomes (BACs) also contain extrachromosomal elements to contain transgenes of heterologous interest. Though naturally occurring in bacteria, not all wild type plasmids contain genetic information that is required to maintain the viability of the host cell in normal conditions. However, plasmids can contain genetic information that provides selective advantages to the host under specific environmental challenges such as antibiotic resistance or resistance to noxious compounds present in the environment. However, in those situations where adverse environmental conditions are not present, the presence of the plasmid is, in fact, a metabolic burden upon the cell (Nordstrom and Austin, 1989). In other words, the metabolic activity required to maintain plasmids exerts a small but real metabolic cost to the host cell relative to those cells not carrying the plasmid in question. This metabolic burden is why many daughter cells tend to 'lose' the plasmid of interest over time if they can continue to exist or reproduce without it. This process of loss or limited replication of the extrachromosomal element(s) also leads to diminished efficiency in those experiments that require the presence of a plasmid genetic component to produce a product of interest and therefore cultures with significant amounts of daughter cells that do not have the plasmid(s) of interest provide a reduced efficiency for the experiment being conducted. This is particularly acute in those fermentation experiments that rely upon economies of scale and consistent production of a molecule of interest to make their cost targets. Daughter cells deficient in the desired plasmids or extrachromosomal elements represent a media and energy sink in overall production and contribute to the economic benefits of fermentation costs.

In the biotechnology industry, plasmids and similar extrachromosomal elements have become very important tools in the genetic engineering of microbes and in the expression of proteins of interest and commercial synthetic biology. Such elements can be manipulated and designed to force the host cell to carry them forward or perish. (Balbas 2001: Baba 2006). In this sense, the cells become irreversibly 'addicted' to maintaining the extrachromosomal element in the cell despite the consequent metabolic burden (hence the term, Plasmid Addiction System or "PAS"). With such a system in hand the researcher can then focus on driving the host cell culture not just to maintain and express the PAS system genes, but to express all the genes contained on such an extrachromosomal element. According to the current invention, this can entail the expression of a number of genes and potential gene products of interest in microbial systems.

Plasmid Addiction Systems and Alternatives

Given the power of such techniques to drive the expression of proteins of interest, it is not surprising that a variety of approaches have been developed to ensure the stable maintenance of plasmids in cells (Nordstrom and Austin, 1989). This includes: (i) site-specific recombination systems functioning as plasmid maintenance systems for high-copy plasmid systems (Grindley et al., 2006); (ii) active partition systems (Funnell and Slavcev, 2004); and, as mentioned above, (iii) plasmid addiction systems (PAS), like the invention provided herein, that prevent the continuing survival/replication of cells not containing and expressing the genes of the plasmid of interest (Gerdes et al., 2005).

Site-Specific Recombination Control Systems

Site-specific recombination is a type of genetic recombination in which a DNA strand exchange takes place between segments possessing at least a certain degree of sequence homology. In this system, a site-specific recombinase(s) (SSRs) performs rearrangements of DNA segments by recognizing and binding to short DNA sequences (sites), at which they cleave the DNA backbone, exchange the two DNA helices involved and then rejoin the DNA strands. (Datsenko and Wanner, 2000). While in some site-specific recombination systems just a single recombinase enzyme and the corresponding recombination sites is enough to perform all these reactions, in other systems a number of accessory proteins and/or accessory sites are also needed— each addition adding to the complexity and thereby decreasing both the reliability and versatility of this system. (Baba et al., 2006). In addition, the constitutive expression of the required recombinases can also lead to undesired genotypic changes and the use of the system in terms of its initial development can be challenging in terms of the transfer of the recombinases genes to progeny.

Plasmid Instability

As mentioned above, microbes tend towards eliminating plasmids or limiting the reproduction of plasmids in cells due to the ongoing metabolic burden of both maintaining the plasmid itself and of expressing the gene(s) contained therein. (Rosano et al., 2014). Additionally, cells may not favor plasmid replication and expression when the plasmids in question may contain genes, that when expressed, produce toxic products in the cell or in its immediate environment of the cell. Of course, the interest to those utilizing such microbial systems is the maintenance of the engineered genetic changes and consequent expression of the inserted genes. In this sense, stable inheritance of the plasmid and host generally requires that: (1) the plasmid must replicate once each generation; (2) copy number deviations must be rapidly corrected before cell division, and, (3) upon cell division, the products of plasmid replication must be distributed to both daughter cells in a reliable and consistent manner. (Balbas et al., 1986).

In general, the stable maintenance of low-copy-number plasmids in bacteria is actively driven by partition mechanisms that are responsible for the positioning of plasmids inside the cell prior to replication. Various such partition systems are ubiquitous in the microbial world and are encoded by many bacterial chromosomes as well as plasmids. These systems, although different in sequence and mechanism, typically consist of two proteins and a DNA partition site or prokaryotic centromere on the plasmid in question. One protein binds to the centromere to form a partition complex, and the other protein uses the energy of nucleotide binding and hydrolysis to transport the plasmid as needed. For plasmids, this minimal cassette is sufficient to conduct appropriate segregation. In an optimal setting the strain selected to carry a plasmid of interest will have a partition system that provides or consistent and reliable plasmid reproduction. (Balbas et al., 1986; Rawlings 1999).

Engineered Plasmid Stabilization Systems

There are systems engineered to stably maintain the plasmids of interest. One particularly common system is the use of antibiotics as selection tools. In such systems, the antibiotic resistance gene in the plasmid of interest protects the cell carrying it, at the same time it effectively "forces" the cell to maintain it when the bacterial cell is grown in a media-enriched with the corresponding antibiotic. (Cranenburgh, R. M. et al., 2001). However, this method is subject to a number of difficulties and concerns. The antibiotic resistance approach is expensive, requiring the use of costly antibiotics and some may find it objectionable as a culture method in when used in industrial production methods could be a way that accelerates and/or spreads the development of bacterial antibiotic resistance that could affect human and/or animal populations negatively. Moreover, in large-scale production applications, the use of antibiotics may impose other limitations. With respect to commercial bioreactors, antibiotic resistance mechanisms can degrade the antibiotic itself and permit a substantial population of plasmid-less cells to persist in the culture. Such plasmid-less cells are unproductive and decrease the overall output of the bioreactor, thereby increasing cost and decreasing efficiency. (Balbas 2001; Baba 2006).

Segregational Plasmid Maintenance Functions

Stable lower copy number plasmids typically employ a partitioning function that actively distributes plasmid copies between daughter cells. Examples of partitioning mechanisms include: pSC101, F factor, P1 prophage, and IncFII drug resistance plasmids. Such functions act to physically segregate plasmids during replication. In terms of functionality many small plasmids rely on a high copy number, distributed throughout the cell, to ensure at least one copy is maintained by each daughter cell upon division. Many large, low-copy number plasmids, on the other hand, encode active segregation systems to avoid stochastic loss. A variety of partitioning systems exist, but most rely on three components: a centromeric DNA region, a cytomotive filament, and an adaptor protein linking the two. In type II segregation bacterial actin-like protein (ALP) filaments drive plasmid separation. (Balbas et al., 2001; Balbas 1986; Schumacher 2014).

Post-Segregational Killing (PSK) Functions

Naturally occurring PSK plasmid maintenance functions typically employ a two-component toxin-antitoxin system and generally operate as follows: The plasmid encodes both a toxin and an antitoxin. The antitoxins are less stable than the toxins, which tend to be quite stable. In a plasmid-less daughter cell, the toxins and anti-toxins are no longer being produced; however, the less stable antitoxins quickly degrade, thereby freeing the toxin to kill the cells in the surrounding area without the antitoxins being present. (Gerdes 1990).

The toxins are generally small proteins and the antitoxins are either small proteins or antisense RNAs which bind to the toxin-encoding mRNAs preventing their synthesis (EX: antisense systems such as hok-sok). In antisense maintenance systems, the antitoxins are antisense RNAs that inhibit translation of toxin-encoding mRNAs. Like the antitoxin peptides, the antisense RNAs are less stable than the toxin-encoding mRNA. Loss of the plasmid permits existing antitoxins to degrade, thereby permitting synthesis of the toxin which kills the host cell. A limitation of the hok-sok system is that a significant number of plasmid-less cells can arise when the hok-sok system is inactivated by mutations within the Hok open reading frame. (Gerdes 1990).

Balanced Lethal Systems

In a balanced-lethal system (a PSK function), a chromosomal gene encoding an essential structural protein or enzyme is deleted from the bacterial chromosome or is mutated such that the gene can no longer operate (Fu., 2000). The removed or damaged gene is then replaced by a plasmid comprising a fully operating gene. Loss of the plasmid results in an insufficiency of the essential protein and the death of the plasmid-less cell. Balanced-lethal systems based on catalytic enzyme production are subject to a number of deficiencies. In particular, since complementation of the chromosomal gene deletion requires only a single gene copy, it is inherently difficult to maintain more than a few copies of an expression plasmid. The plasmid less host strain must be grown on special media to chemically complement the existing metabolic deficiency. (Fu 2000).

Commercial Efforts & Need

Biotechnical production processes often operate with plasmid-based expression systems in well-established prokaryotic and eukaryotic hosts such as *Escherichia coli* or *Saccharomyces cerevisiae*, respectively. Genetically engineered organisms produce important chemicals, biopolymers, biofuels and high-value proteins like insulin. In those bioprocesses plasmids in recombinant hosts have an essential impact on productivity. (Kroll J., 2010). Plasmid-free cells lead to losses in the entire product recovery and decrease the profitability of the whole process (Table 1). Often, the use of antibiotics in industrial fermentations is not an available or desirable option to maintain plasmid stability. Especially in pharmaceutical or GMP-based fermentation processes, deployed antibiotics must be inactivated and removed. As stated above, they are also costly. Several plasmid addiction systems (PAS) have been described in the literature and referenced above. The current PAS provides a new method that is antibiotic free, remains absolutely necessary for cellular replication and homeostasis and allows multiple gene carrying plasmids, or the like, to be maintained efficiently in culture.

Given the above, there remains a need in the art for a new PAS that is reliant on a balanced lethal system, not requiring antibiotics is useful to industry and can drive the production of high volumes of compounds of interest in a commercially efficient way.

SUMMARY OF THE INVENTION

The present invention encompasses improved methods of devising a plasmid addiction system that can enhance the production of proteins of interest and do so at commercial scale.

According to the current invention, a biosynthetic method is provided for the production of one or more proteins of interest in a microbial system.

Recombinant plasmids carrying the gene of interest are obtained by cultivation of bacteria. For selecting bacterial transformants, and in order to ensure the maintenance of the plasmids in the bacterial host cell, an antibiotic resistance gene is traditionally included in the plasmid backbone. Selection for plasmids is achieved by growing the cells in a medium containing the respective antibiotic, in which only plasmid bearing cells are able to grow, often with a marker gene included. A number of plasmid addiction systems (PAS) already exist, mainly as toxin-antitoxin systems that limit the plasmids to single copy or aimed for use in open environments like bioremediation contexts. However, there are few examples of nutrition-based plasmid addiction systems, or ones exhibiting long-term stability in an industrial setting. The current invention provides both.

According to the current invention a plasmid addiction system utilizing the succinate pathway as the conditional mutant where key chromosomal genes have been removed and placed in the plasmids to be expressed and maintained in daughter cells. Such a system could be used for the production of specific amylases, pathway genes, lipases, proteases, vitamins or antibiotics, and according to the current invention could be forced to maintain up to four different plasmids.

According to the preferred embodiments of the invention, the applicants provide a plasmid addiction system based on the synthetic lethal deletion of either the double mutant sucAD or the quadruple mutant sucABCD, wherein the native mutations are complemented on one or more plasmids. The plasmid(s) of interest allows for near wild-type growth without supplementation of DAP or any other intermediate and is retained for many generations in the absence of selective markers. It is useful in a laboratory context, as transformants can be grown LB plates without any additional supplementation; the parent strains cannot grow without supplementation with DAP. It is useful in an industrial context wherein neither antibiotics nor their requisite selection marker genes are wanted or desired. Given the inclusion of up to four required genes this means that four plasmids of different compositions can be retained in a fermentation of interest and at low cost. That is, a single plasmid can be maintained with a single gene of interest or up to four different plasmid types, each with one of the four required genes, carrying other genes of interest can be provided in the current system efficiently and with low cost.

BRIEF DESCRIPTION OF THE DRAWINGS

FIG. 2B provides a schematic of the genomic context of *E. coli* BW25113 ΔsucAD; and FIG. 2C provides a schematic of the genomic context of *E. coli* BW25113 ΔsucABCD.

DETAILED DESCRIPTION OF THE INVENTION

Figure 1A:
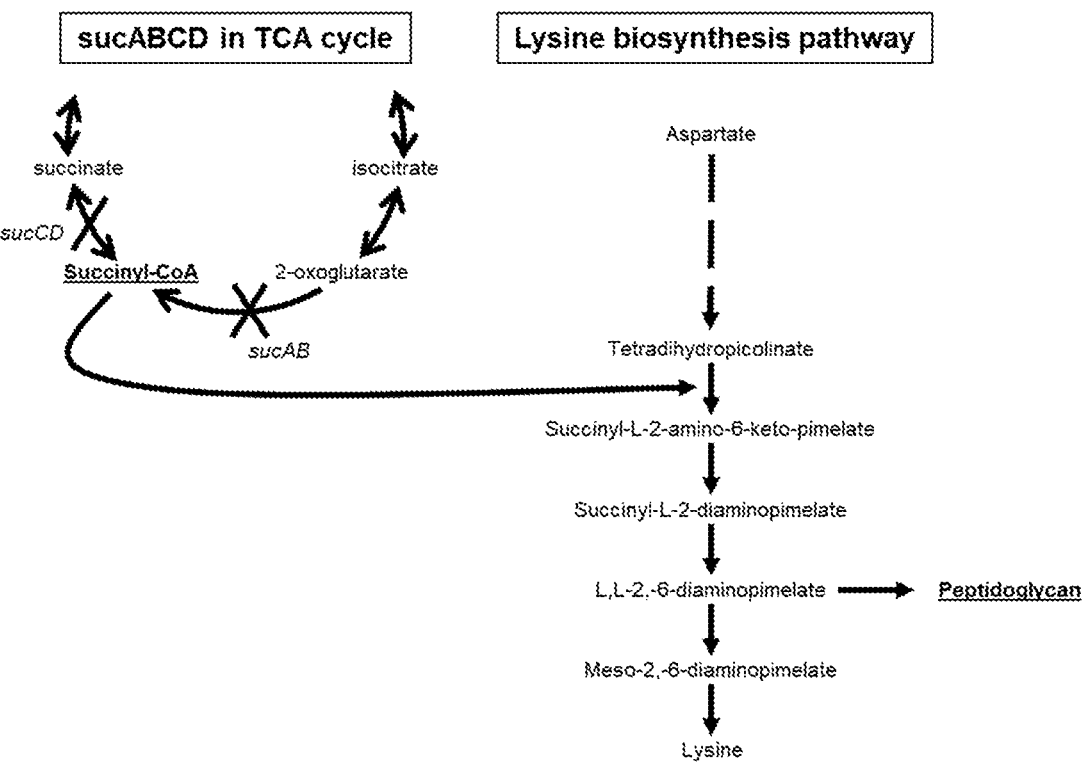
FIGS. 1A-1B. Show succinate and succinyl-CoA in context of central *E. coli* metabolism and cell wall biosynthesis (FIGS. 1A and 1B).

The following abbreviations have designated meanings in the specification:

Explanation of Terms

Cellular system is any cells that provide for the expression of ectopic proteins. It included bacteria, yeast, plant cells and animal cells. It includes both prokaryotic and eukaryotic cells. It also includes the in vitro expression of proteins based on cellular components, such as ribosomes.

Growing the Cellular System. Growing includes providing an appropriate medium that would allow cells to multiply and divide given the changes to the succinate pathway. It also includes providing resources so that cells or cellular components can translate and make recombinant proteins. According to the current invention the cells grow on LB media. Such cells do not unless they are supplied with 120 μM DAP.

Protein Expression. Protein production can occur after requisite gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Acronyms

TCA—Tricarboxylic Acid
DAP—Diaminopimelic Acid
PAS—Plasmid addiction system
TB—Terrific Broth
LB—Luria Broth
Y(E)PD—Yeast Extract Peptone Dextrose (medium)
sucA—*E. coli* gene encoding the E1 component of the 2-oxoglutarate dehydrogenase enzyme
sucB—*E. coli* gene encoding the E2 component of the 2-oxoglutarate dehydrogenase enzyme
sucC—*E. coli* gene encoding the 0 subunit of the succinyl-CoA synthetase enzyme
sucD—*E. coli* gene encoding the a subunit of the succinyl-CoA synthetase enzyme

Alternative Marker Genes

If marker genes are required for one or more genes of the current invention examples include: genes encoding restriction nucleases (e.g. CviAII, a restriction endonuclease originating from *Chlorella* virus PBCV-1; Zhang et al., 1992), EcoRI (Torres et al., 2000), genes encoding toxins that interact with proteins, e.g. streptavidin or stv13 (a truncated, easy soluble streptavidin variant), as described by Szafransky et al., 1997: Kaplan et al., 1999; Sano et al., 1995, which act by deprivation of biotin, an essential protein in cell growth); genes encoding proteins that damage membranes (the E gene protein of φX174 (Ronchel et al., 1998; Haidinger et al., 2002), gef (Jensen et al., 1993; Klemm et al., 1995), relF (Knudsen et al., 1995); genes that encode other bacterial toxins, e.g. the ccdb gene (Bernard and Couturier, 1992) that encodes a potent cell killing protein from the F-plasmid trapping the DNA gyrase or sacB from *Bacillus subtilis* (Gay et al., 1983); or genes that encode eukaryotic toxins that are toxic to the bacterial host (e.g. FUS; Crozat et al., 1993). When using toxic genes, it is essential that their expression can be modulated by an inducible promoter. This promoter must not be active without an inductor, but provide expression upon induction, sufficient to inhibit cell growth.

In certain embodiments, the marker gene is selected from genes encoding restriction nucleases, streptavidin or genes that have an indirect toxic effect, e.g. sacB, as described above.

A repressor is a protein that binds to an operator located within the promoter of an operon, thereby down-regulation transcription of the gene(s) located within said operon. Examples for repressors suitable in the present invention are the tetracycline repressor (tet) protein TetR, which regulates transcription of a family of tetracycline resistance determinants in Gram-negative bacteria and binds to tetracycline (Williams, et al., 1998; Beck, et al., 1982; Postle et al., 1984), the tryptophan repressor (trp), which binds to the operator of the trp operon, which contains the tryptophan biosynthesis gene (Yanofski et al., 1987).

Examples for inducible promoters are promoters, where transcription starts upon addition of a substance, thus being regulatable by the environment, e.g. the lac promoter, which is inducible by IPTG (Jacob and Monod, 1961), the arabinose-promoter (pBAD), inducible by arabinose (Guzman et al., 1995), copper-inducible promoters (Rouch and Brown, 1997), and cumate-inducible promoters (Choi et al 2010).

Alternately, constitutive promoters may be used, wherein transcription of the desired transgene is always driven on, regardless of the growth phase or environmental variables.

In an alternative embodiment, one could monitor the expression of a single gene of interest through the use of a marker gene as a reporter gene. Genes that could be used to provide this functionality include genes encoding GFP (Green Fluorescent Protein), hSOD (human superoxide dismutase), lacZ (beta-glucosidase), CAT (chloramphenicol acetyltransferase), nptII (neomycin phosphotransferase) or luciferase.

A reporter gene is useful in cultivation processes whenever information on the presence or absence of a plasmid in a host cell or on plasmid copy number is needed. Such information is particularly useful when fermentation processes are to be optimized with regard to control of plasmid copy number. A reporter gene may also serve as a surrogate of a toxic marker gene and may thus be used in experimental settings that aim at proving the functionality of constructs to be employed for the gene-regulating or silencing and to determine their effect on a toxic marker gene.

In certain embodiments of the invention, the marker gene may be an endogenous host gene, which may be any gene of interest that is intended to be regulated. In this case, the host cell is engineered such that the sequence encoding the sequence is operably associated with the relevant host gene.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

The present invention relates to a system for an improved production method for proteins of interest in a microbial system that does not require markers, antibiotics and can produce proteins of interest at a high-level.

Bacterial Strains and Growth Conditions

BW25113 and the deletions for ΔsucA::KanR and ΔsucD::KanR were obtained from the *E. coli* Genetic Stock Center (CGSC). Cells were typically grown in Luria Broth (LB), but experiments were also performed in TB, YPD, YEPD, Nutrient Broth with corn steep liquor, and other rich media (Miller, 1972). Diaminopimelic acid (Sigma D1377)

was used at 120 μM to aid in screening as the ΔsucAD double deletion is synthetic lethal (Mattozzi et al., 2013; Yu et al., 2006).

Construction of Strains with Chromosomal Mutations

P1vir transduction (Miller, 1972) was used to create kanamycin-resistant double knockout strains of *E. coli* BW25113 and screened with 120 μM DAP on LB kanamycin plates. These were screened for deletions of ΔsucA and ΔsucD via colony PCR. This KanR donor strain was also used to create double knockouts of *E. coli* strains BL21, BL21(DE3), MG1655, MG1655(DE3) ΔlacY, and W3110. Plasmid pCP20 was used to remove the kanamycin resistance markers using its FLP/FRT-based recombinase (Baba et al., 2006; Datsenko and Wanner, 2000). Since sucA and sucD are separated by only 6 kb, Kan sensitive cells exhibiting the quadruple deletion ΔsucABCD were usually isolated after the pCP20 FLP recombinase step (Datsenko and Wanner, 2000).

Construction of Recombinant Plasmids

Codon-optimized sequences encoding sucA, sutcB, sucC, and sucD were synthesized (Quintara Bioworks, Emeryville Calif.). CIDAR *E. coli* Modular cloning (Iverson et al., 2016), was used to generate versions of sucABCD natural operon and the sucAD synthetic operon. Both versions were based on the *E. coli* MG1655 native sequence, but with illegal BsaI and BpiI sites replaced in-frame so as not to affect protein sequences. Additional codon optimization was performed to minimize recombination effects. Operons sucABCD and sucAD were identical except that the sequence between the start codon of sucB and the stop codon of sucC were deleted. (Yu et al., 2005).

According to the current invention, plasmids were transformed into ΔsucAD and ΔsucABCD strains via electroporation and selected on LB plates without any additional supplementation; the parent strains cannot grow without supplementation with DAP. Clones were confirmed by sequence.

Cultivation of Plasmid-Addicted Strains

Plasmid-bearing *E. coli* strains were grown in LB without additional supplementation in 24-well plates and in a Bio-Lector flower plates (Funke et al., 2009).

The present invention can be widely used in state-of-the-art fermentations, both for plasmid DNA production and for producing recombinant proteins.

Several approaches for fermentation of pDNA have been described that are useful for applying the present invention. The methods for plasmid DNA production differ with regard to the level of control imposed upon the cells and the numerous factors that influence fermentation.

To obtain higher quantities of plasmids, the cells can be cultivated in controlled fermenters in so-called "batch fermentations", in which all nutrients are provided at the beginning and in which no nutrients are added during cultivation. (Reinikainen, P., et al; 1988). Cultivations of this type may be carried out with culture media containing so called "complex components" as carbon and nitrogen sources, as described e.g. by O'Kennedy et al., 2003, and Lahijani et al., 1996, and in WO 96/40905, U.S. Pat. No. 5,487,986 and WO 02/064752. Alternatively, synthetic media may be used for pDNA production, e.g. defined culture media that are specifically designed for pDNA production (Wang et al., 2001; WO 02/064752).

The present invention may also be used in fed batch fermentations of *E. coli*, in which one or more nutrients are supplied to the culture by feeding, typically by using a feed-back control algorithm by feeding nutrients in order to control a process parameter at a defined set point. Feed-back control is hence directly related to cell activities throughout fermentation. Control parameters which may be used for feed-back control of fermentations include pH value, on line measured cell density or dissolved oxygen tension (DOT). A feed-back algorithm for controlling the dissolved oxygen tension at a defined set point by the feeding rate was described in WO 99/61633.

Alternatively, the invention may be applied in a process for producing plasmid DNA, in which *E. coli* cells are first grown in a pre-culture and subsequently fermented in a main culture, the main culture being a fed-batch process comprising a batch phase and a feeding phase. The culture media of the batch phase and the culture medium added during the feeding phase are chemically defined, and the culture medium of the feeding phase contains a growth-limiting substrate and is added at a feeding rate that follows a pre-defined exponential function, thereby controlling the specific growth rate at a pre-defined value.

When the marker gene is under the control of an inducible promoter, the inducer may be added to the batch at the beginning and/or pulse-wise (both in a batch and in fed-batch cultivations). During the feed phase, the inducer may be added pulse-wise or continuously.

At the end of the fermentation process, the cells are harvested and the plasmid DNA is isolated and purified according to processes known in the art, e.g. by methods based on anion exchange and gel permeation chromatography, as described in U.S. Pat. No. 5,981,735 or by using two chromatographic steps, i.e. an anion exchange chromatography as the first step and reversed phase chromatography as the second step, as described in U.S. Pat. No. 6,197,553. Another suitable method for manufacturing plasmid DNA is described in WO 03/051483, which uses two different chromatographic steps, combined with a monolithic support.

In addition to applying the invention for plasmid production, e.g. for production of plasmids for gene therapy applications, it is also useful for recombinant protein production. (Rawlings 1999).

With regard to recombinant protein production, in principle, any method may be used that has proven useful for expressing a gene of interest in *E. coli*, in particular from a ColE1 type plasmid (see, for review, e.g. Jonasson et al., 2002; Balbas, 2001). The protein may be obtained intracellularly (completely or partially soluble or as inclusion bodies) or by secretion (into the cell culture medium or the periplasmic space) from batch fermentations or, preferably, fed-batch cultivations, using complex, synthetic or semisynthetic media.

In plasmid DNA production, usually plasmid DNA for gene therapy applications, the gene of interest is not expressed in the bacterial host cell. In view of its application in mammals, preferably in humans, where it is to be ultimately expressed, the gene of interest is usually operably associated with a eukaryotic promoter. In contrast, for recombinant production of proteins in *E. coli*, the gene of interest is to be expressed in the host cell therefore under the control of a prokaryotic promoter.

For recombinant protein production, the two promoters, i.e. the promoter controlling the marker gene and the promoter controlling the gene of interest, may be different or the same, as long as no interference occurs that disturbs expression of either one.

Advantageously, since their activity is independent of each other concerning time-point and level of transcription, the promoters are differently regulated. Preferably, the promoter controlling the marker gene is active at the start of the fermentation process and produces moderate amounts of mRNA, while the promoter of the gene of interest is rather strong and activated at a chosen time-point during fermentation. If inducible promoters are used for both the gene of interest and the marker gene, they are usually chosen such that they are turned on by different inducers. Alternatively, the marker gene may be under an inducible promoter and the gene of interest under a constitutive promoter, or vice versa. This applies both for methods in which the marker gene construct is integrated in the bacterial host genome and in which the marker gene construct is contained in a plasmid or phage, as described above.

With regard to induction of the promoter in the various phases of fermentation, the principle described above for plasmid DNA production applies.

The invention has the great advantage that all replicated plasmids are devoid of antibiotic resistance genes and are therefore, in addition to gene therapy applications, suitable for all applications for which the absence of antibiotic resistance genes is required or desirable, e.g. for the generation of recombinant yeast strains that are intended for human and animal food production or for the generation of recombinant plants.

Expression and Maintenance During Fermentation

Maintenance of heterologous DNA presents a major challenge in industrial systems. A number of systems already exist, but there are drawbacks to each of them. Integrating genes into the genome can be slow, require extensive screening, and is limited to a single copy per cell. Larger DNA loops like cosmids and bacterial artificial chromosomes (BACs) can be difficult to isolate from chromosomal DNA or cell debris pellets, and again are limited by copy number. Phages can be difficult to keep contained to the cell types of interest. They could become lytic unexpectedly, causing drastic consequences on a factory-scale. Thus, the most common way to introduce and maintain heterologous DNA into E. coli and other bacterial cultures is via plasmid, wherein the gene(s) of interest are maintained on a small loop of DNA containing sequences comprising an origin of replication and, typically, an antibiotic resistance marker. This marker can be problematic: antibiotics in the media can be expensive and can contaminate final small-molecule products with similar chemical properties. As well, the genes encoding these markers pose a biosafety issue: the antibiotics used in fermentation are the same or similar to the ones used in clinical settings. Though laboratory containment is usually good, large-scale use of antibiotic resistance genes could encourage the spread of dangerous resistant bacteria like methicillin-resistant Staphylococcus aureus (MRSA).

The principle of the invention, i.e. the metabolic context of the succinyl-CoA synthetic lethal deletions is shown in FIG. 1.

In embodiments of the invention, the following components are useful:

Host Cells

Since their replication depends on the host machinery, many plasmids are plasmids with a narrow host range.

Replication is often limited to E. coli and related bacteria such as Salmonella and Klebsiella (Kues and Stahl, 1989). However, according to the current invention a great variety of functional hosts are available including eukaryotic systems. Other suitable hosts include: cells of the genera Corynebacterium, Bacillus, Pseudomonas, Vibrio, Bulkholderia, and really any other bacterium that can stably maintain a heterologous plasmid and has a peptidoglycan cell wall.

Preferred genetic features of the host cell are mutations that improve plasmid stability and quality or recovery of intact recombinant protein. Examples of desirable genetic deletions are:

sucA—E. coli gene encoding the E1 component of the 2-oxoglutarate dehydrogenase enzyme sucB—E. coli gene encoding the E2 component of the 2-oxoglutarate dehydrogenase enzyme sucC—E. coli gene encoding the S subunit of the succinyl-CoA synthetase enzyme sucD—E. coli gene encoding the a subunit of the succinyl-CoA synthetase enzyme.

Each of the genes in this operon encodes part of a heterodimeric enzyme within the TCA cycle. Since sucAB and sucCD are synthetic lethal (Yu et al 2006), either sucAB OR sucCD pair may be deleted and still allow cell growth; albeit with reduced growth rates due to the inability of the cells to use oxygen as a terminal electron acceptor. This can eventually cause cell death, a reduced growth rate, low maximum cell density, and inefficient usage of carbon source. Deletion of at least three of the genes within the sucABCD cluster (or two from opposite conjugate pairs, e.g. ΔsucAD) creates a cell that is auxotrophic for succinyl-CoA. Because succinyl-CoA itself is unstable and expensive to procure commercially, it was discovered that supplementation of DAP in the medium can allow the cells to grow. This is because the external DAP can be incorporated into the cell walls, negating the need for the succinyl-CoA cofactor (FIG. 1). The cells can still grow, but albeit with a growth defect due to their inability to fully utilize oxygen as a terminal electron acceptor.

Constructs for Engineering the Host Cells

The principle of a construct suitable for engineering the host cells is shown in FIG. 2: The host strains were generated via P1 transduction (above), and the plasmids were produced via Gibson assembly, cloning, Golden Gate and/or modular cloning.

Characteristics of Plasmids for the System

The plasmids are required to express the genes specifically deleted in the host strain. In this example, codon-optimized versions of E. coli sucAD and sucABCD are expressed on plasmids, complementing the deletions made to BW25113 ΔsucAD and ΔsucABCD respectively.

EXAMPLES

Two or four key genes expressing essential proteins for the tricarboxylic acid (TCA) cycle were deleted from the E. coli genome. Previously these genes have been shown to be synthetic lethal (Yu et al., 2006). These cells are thus auxotrophic for succinyl-CoA. The cells can make up the energetic needs of the TCA cycle simply through fermentative growth, but the lack of a complete TCA cycle causes inefficient growth, and accumulation of toxic fermentative byproducts ethanol and acetate because the cells are unable to effectively use oxygen as a terminal electron acceptor. This can eventually cause cell death, a reduced growth rate, low maximum cell density, and inefficient usage of carbon source. In addition to the TCA cycle, succinyl-CoA is also used as a cofactor in many metabolic pathways. Perhaps the most important is the lysine synthesis pathway, wherein succinyl-CoA is required as an essential cofactor for generating diaminopimelic acid (DAP). DAP is a key monomer in the murein or peptidoglycan cell wall and was thus required for growth.

Previously, we built a system taking advantage of this fact (Mattozzi et al., 2013), as a test of a carbon fixation system. However, the knockouts were only used as a proxy for cell metabolic processes from *Chloroflexus aurantiacus*, not the ability of the cells to retain the plasmid or drive the production of proteins of interest. Double mutant ΔsucAD cells containing a plasmid expressing a succinyl-CoA:(S)-malyl-CoA transferase operon reduced but did not entirely remove the need for DAP in the system.

Bacterial Strains and Growth Conditions

BW25113 and the deletions for ΔsucA::KanR and ΔsucD::KanR were obtained from the *E. coli* Genetic Stock Center (CGSC) at Yale University. Cells were typically grown in Luria Broth (LB), but experiments were also performed in TB, YPD, YEPD, Nutrient Broth with corn steep liquor, and other rich media (Miller, 1972). Diaminopimelic acid (Sigma D1377) was used at 120 μM to aid in screening as the ΔsucA(B) Δsuc(C)D double deletion is synthetic lethal (Mattozzi et al., 2013; Yu et al., 2006).

Construction of Strains with Chromosomal Mutations

P1vir transduction (Miller, 1972) was used to create kanamycin-resistant double knockout strains of *E. coli* BW25113 and screened with 120 μM DAP on LB kanamycin plates. These were screened for deletions of ΔsucA and ΔsucD via colony PCR. This KanR donor strain was also used to create double knockouts of *E. coli* strains BL21, BL21(DE3), BL21*(DE3), MG1655, MG1655(DE3) ΔlacY, C41, and W3110. Plasmid pCP20 was used to remove the kanamycin resistance markers using its FLP/FRT-based recombinase (Baba et al., 2006; Datsenko and Wanner, 2000). Since sucA and sucD are separated by only 6 kb, Kan sensitive cells exhibiting the quadruple deletion ΔsucABCD were usually isolated after the pCP20 FLP recombinase step (Datsenko and Wanner, 2000).

Construction of Recombinant Plasmids

CIDAR *E. coli* Modular cloning (Iverson et al., 2016), a Golden Gate based technology, was used to generate versions of sucABCD natural operon and the sucAD synthetic operon. Both versions were based on the *E. coli* MG1655 native sequence, but with illegal BsaI and BpiI sites replaced in-frame so as not to affect protein sequences. Operons sucABCD and sucAD were identical except that the sequence between the start codon of sucB and the stop codon of sucC were deleted. Plasmids were transformed into sucAD and sucABCD strains via electroporation and selected on LB plates without any additional supplementation; the parent strains cannot grow without supplementation with DAP. Clones were confirmed by sequence.

Plasmids were transformed into ΔsucAD and ΔsucABCD strains via electroporation and selected on LB plates without any additional supplementation; the parent strains cannot grow without supplementation with DAP. Clones were confirmed by sequence.

Figure 1B:
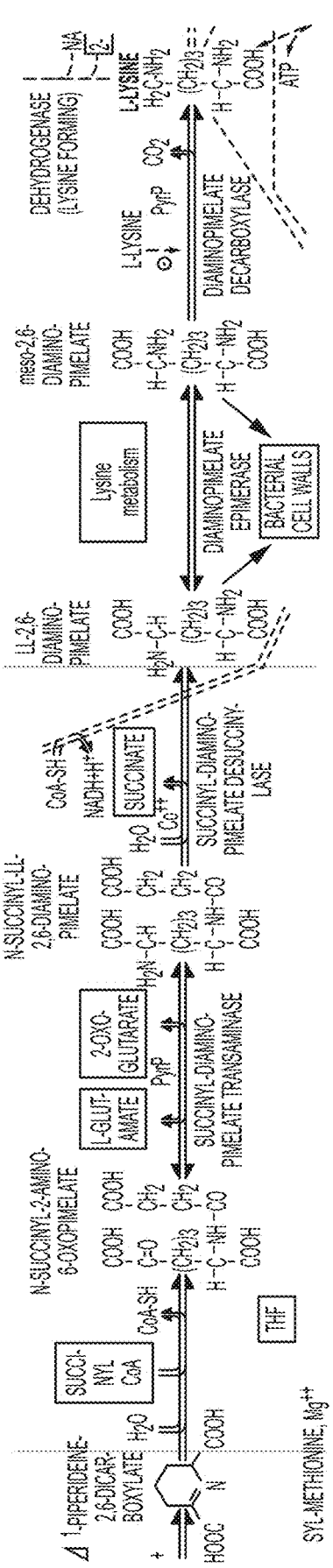
Figure 2A:
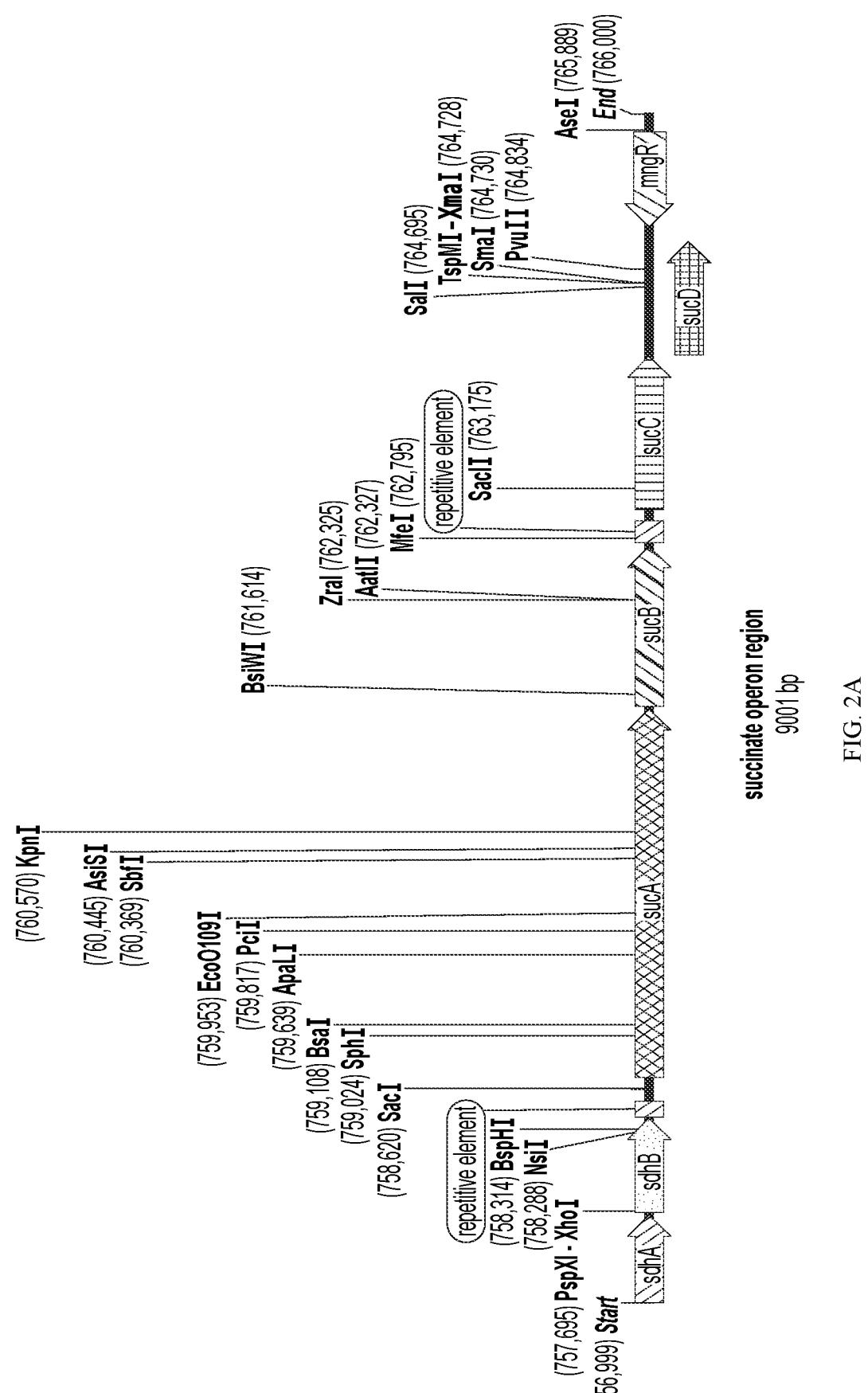
FIGS. 2A-2C. Show the multiple deletions sucAD (FIG. 2B) and sucABCD (FIG. 2C), which are synthetic lethal in the *E. coli* chromosome. The genomic context for the native *E. coli* strain of the invention—BW25113 and its succinyl-CoA operon is shown in FIG. 2A.

In FIG. 1A, we see the general metabolic context of succinyl-CoA, diaminopimelic acid, and peptidoglycan on murein cell walls. Succinyl-CoA generated by the gene products of sucAB and sucCD is used to produce lysine and its immediate biochemical precursor, diaminopimelate (DAP), critically required for *E. coli* cell wall (peptidoglycan or murein) biosynthesis. FIG. 1B provides the detailed metabolic context of the succinyl-CoA cofactor in diaminopimelate and lysine metabolism (Excerpted from Michel and Schomberg 2012). In FIG. 2A, the genomic context for the native *E. coli* strain of the invention—BW25113 and its succinyl-CoA operon are provided. According to the current invention the DNA sequence for this is (SEQ ID NO: 1).

Figure 2B:
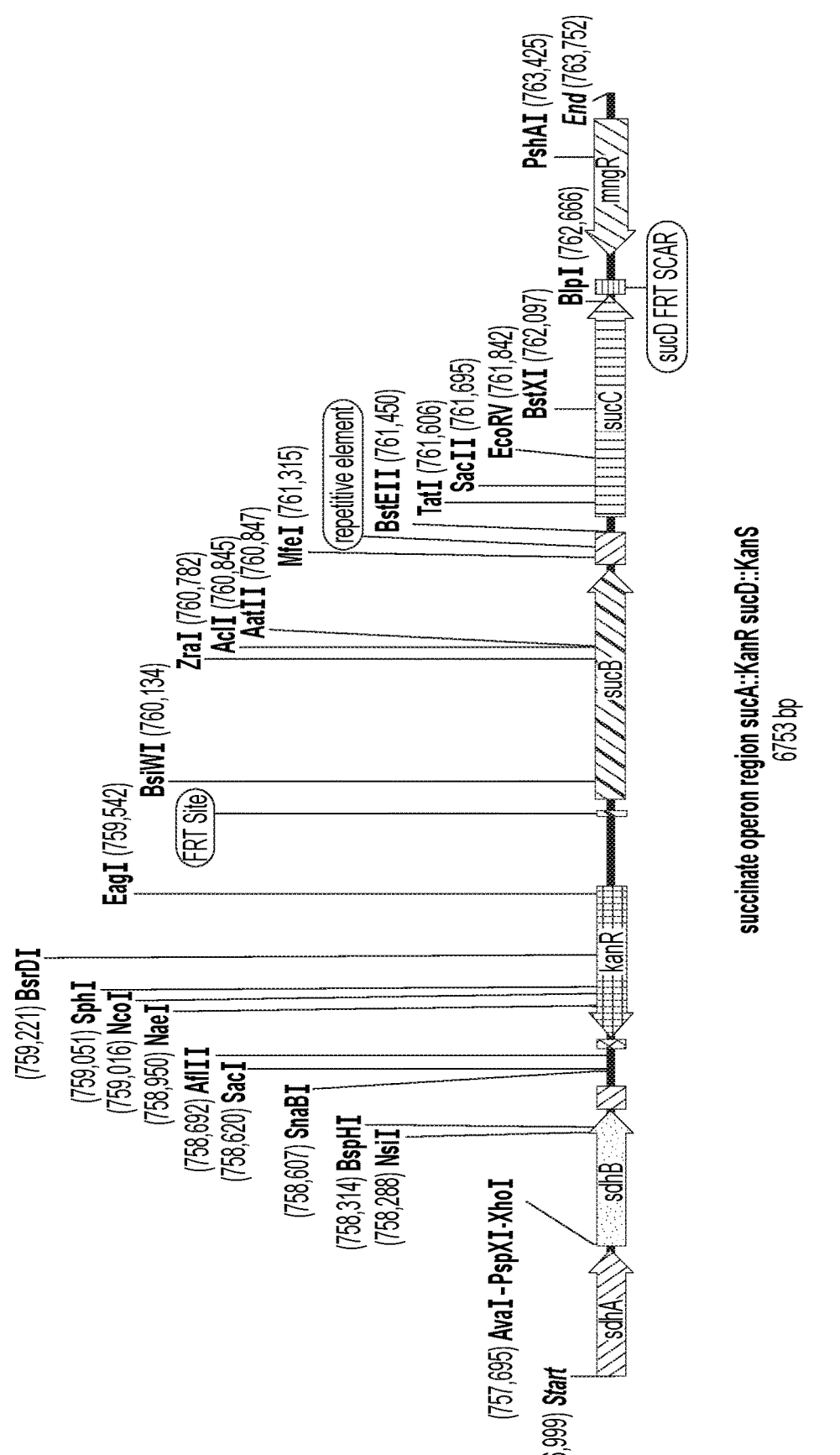
Figure 2C:
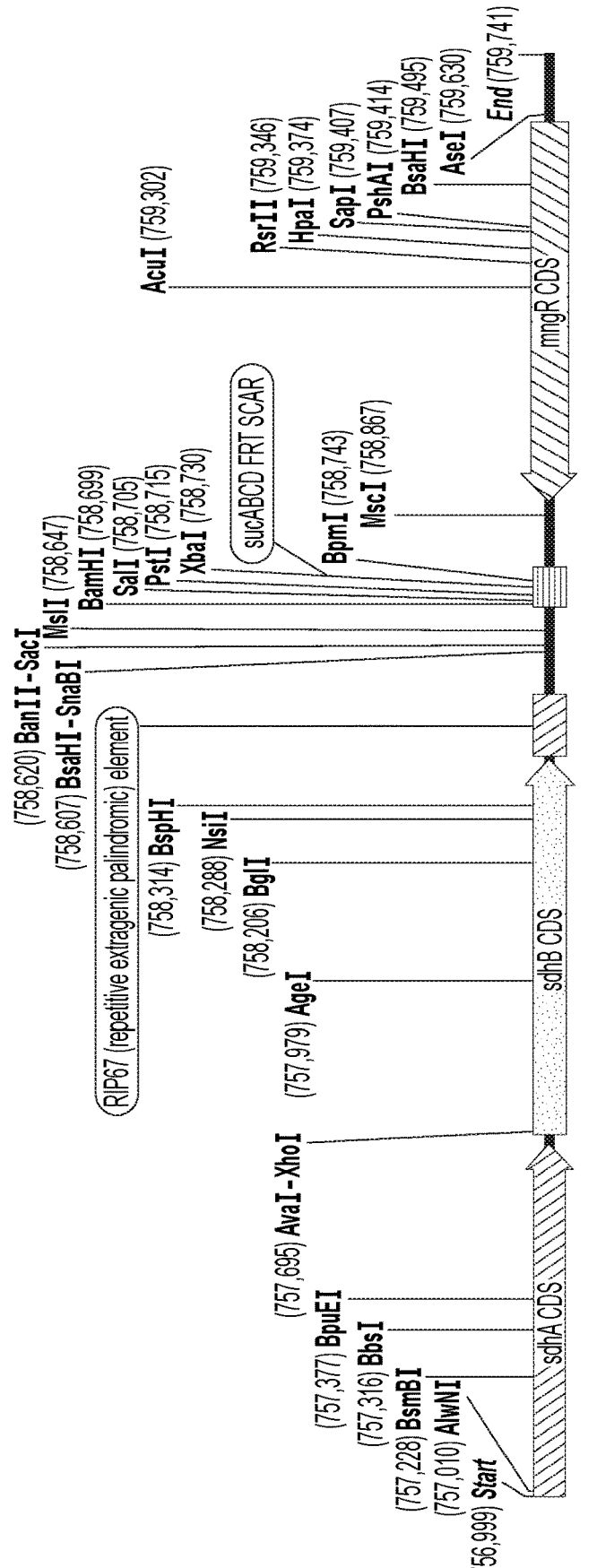

FIG. 2B provides a schematic of the genomic context of *E. coli* BW25113 ΔsucAD. This is the result of a P1 transduction in the *E. coli* genome wherein ΔsucA::kanR was used as a donor. Recipient strain was *E. coli* BW25113 ΔsucD::kanS, generated by removing kanamycin resistance via pCP20-mediated FRT excision (thereby providing SEQ ID NO: 2). FIG. 2C provides a schematic of the genomic context of *E. coli* BW25113 ΔsucABCD. The result is the removal of kanamycin resistance via pCP20-mediated FRT excision. Since sucA and sucD are within 6 kb, deletions of the entire sucABCD operon were isolated in the purification process (SEQ ID NO: 3).

Figure 3A:
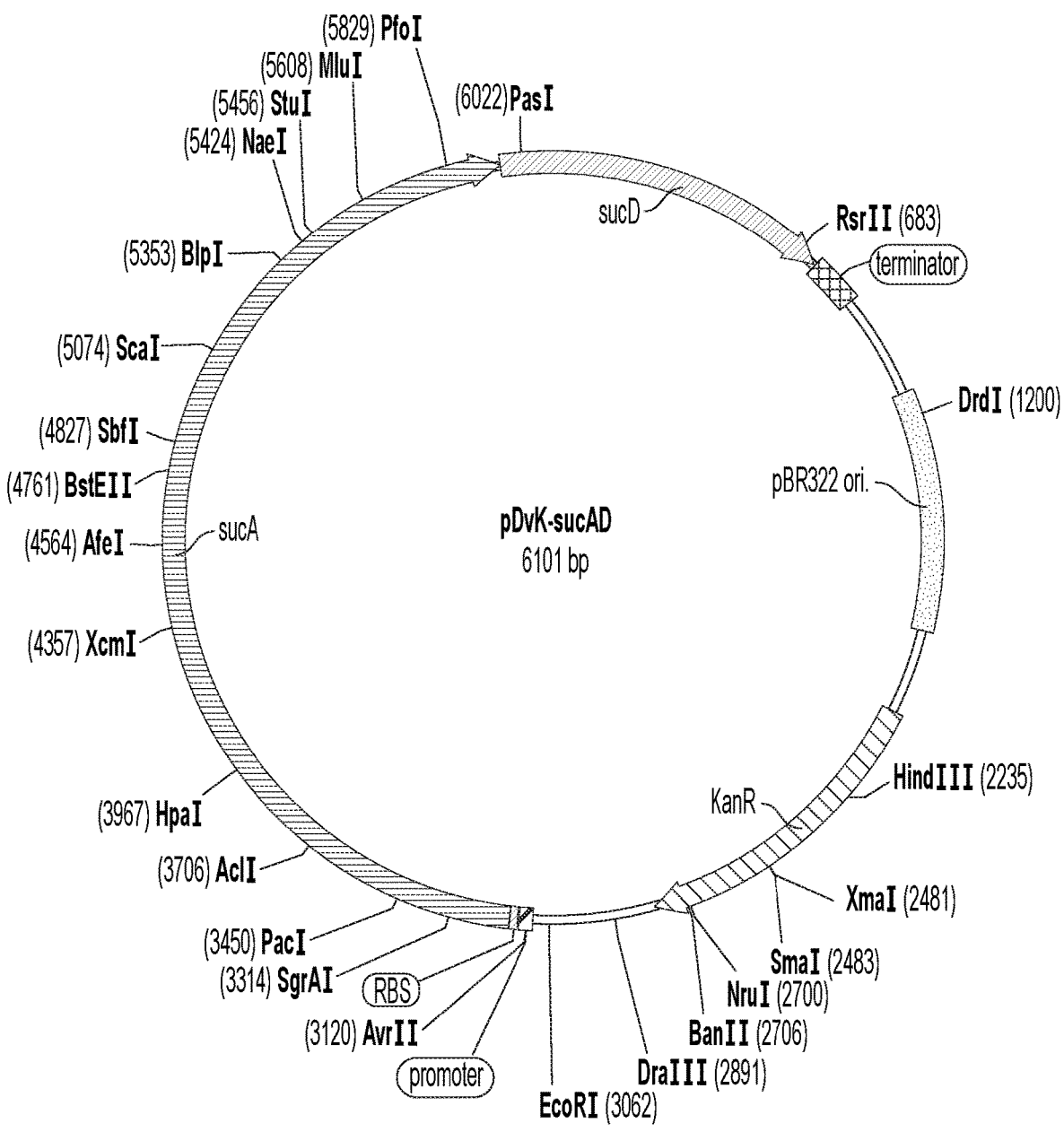
FIGS. 3A-3E. Show plasmid maps of pDvS and pDvQ plasmids, cloning vectors designed to express sucAB and sucABCD complements rather than antibiotic resistance markers. pDvK-sucAD (FIG. 3A); pDvK-sucABCD (FIG. 3B); pDvS-Kan-dropout (FIG. 3C); and pDvQ-Kan-dropout (FIG. 3D); pDvK-sucBC (FIG. 3E)
Figure 3B:
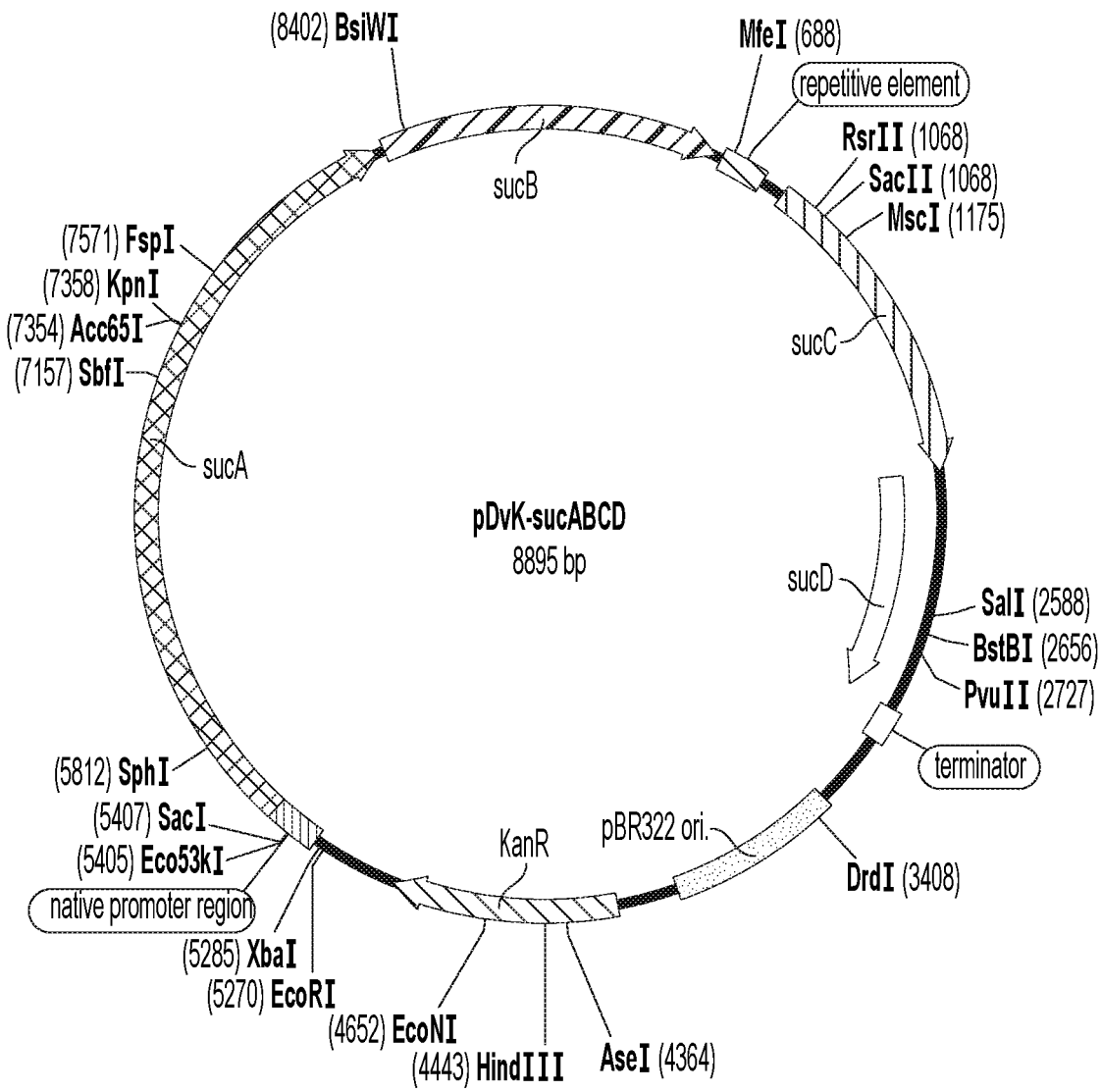
Figure 3C:
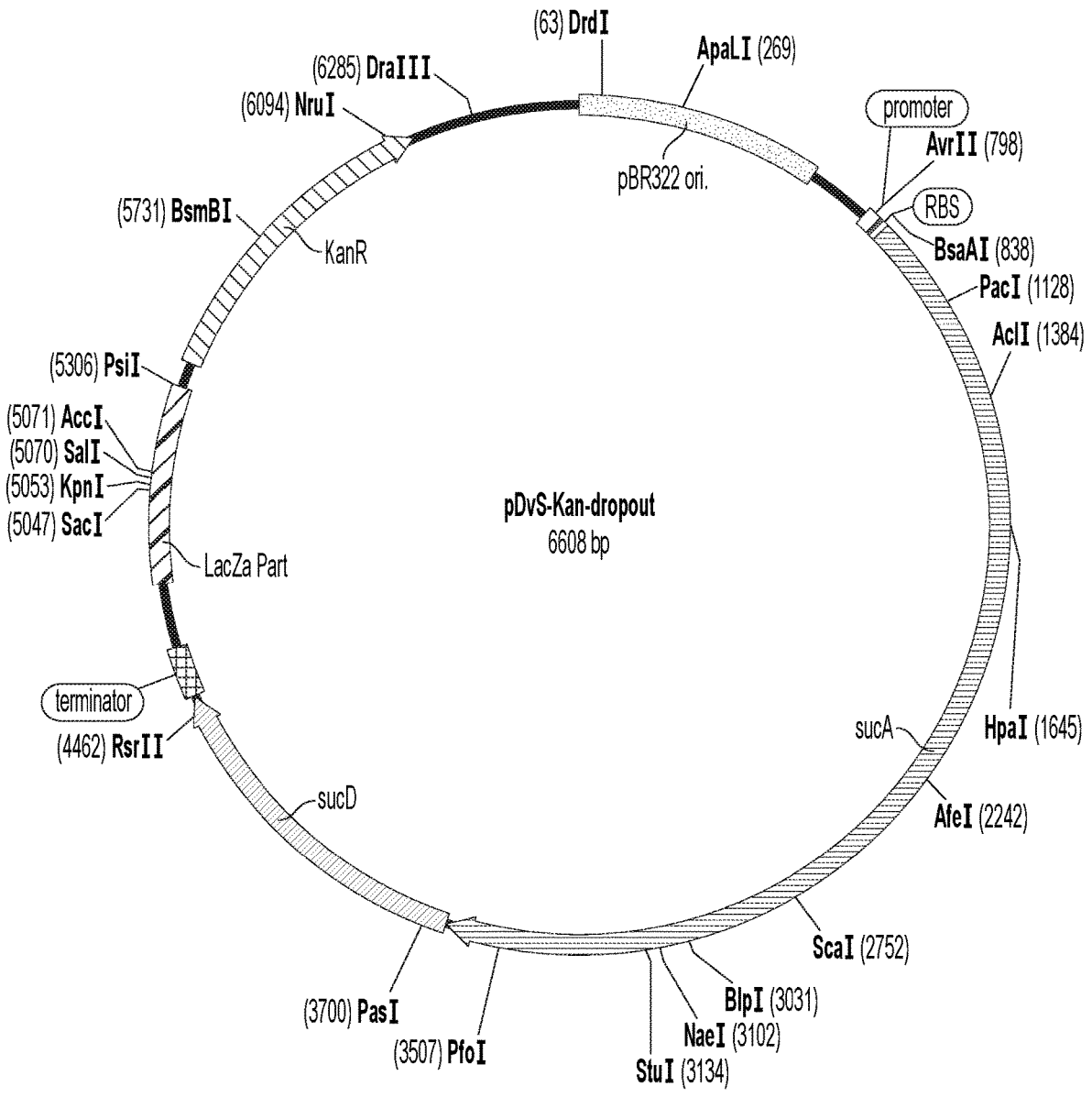
Figure 3D:
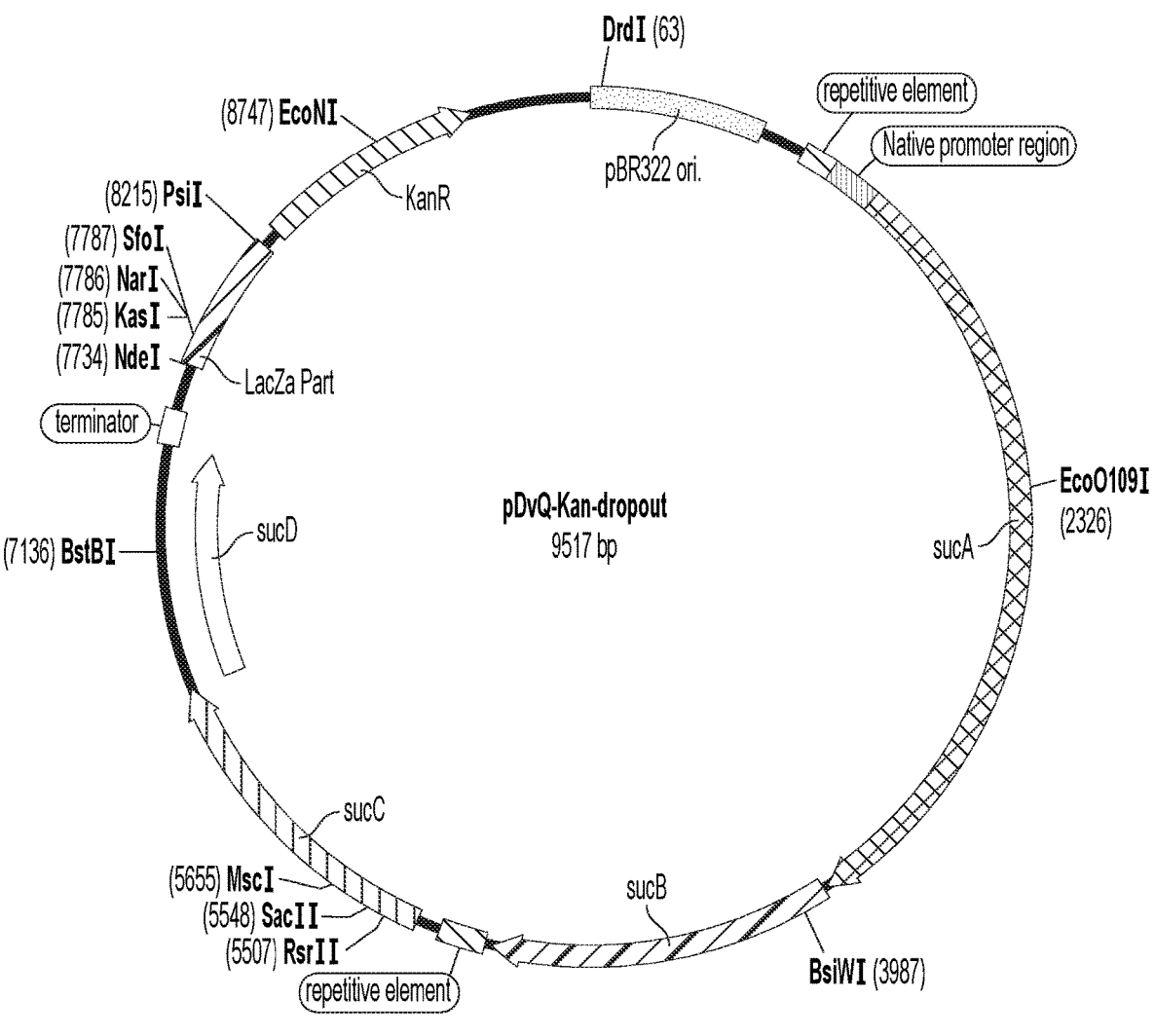
Figure 3E:
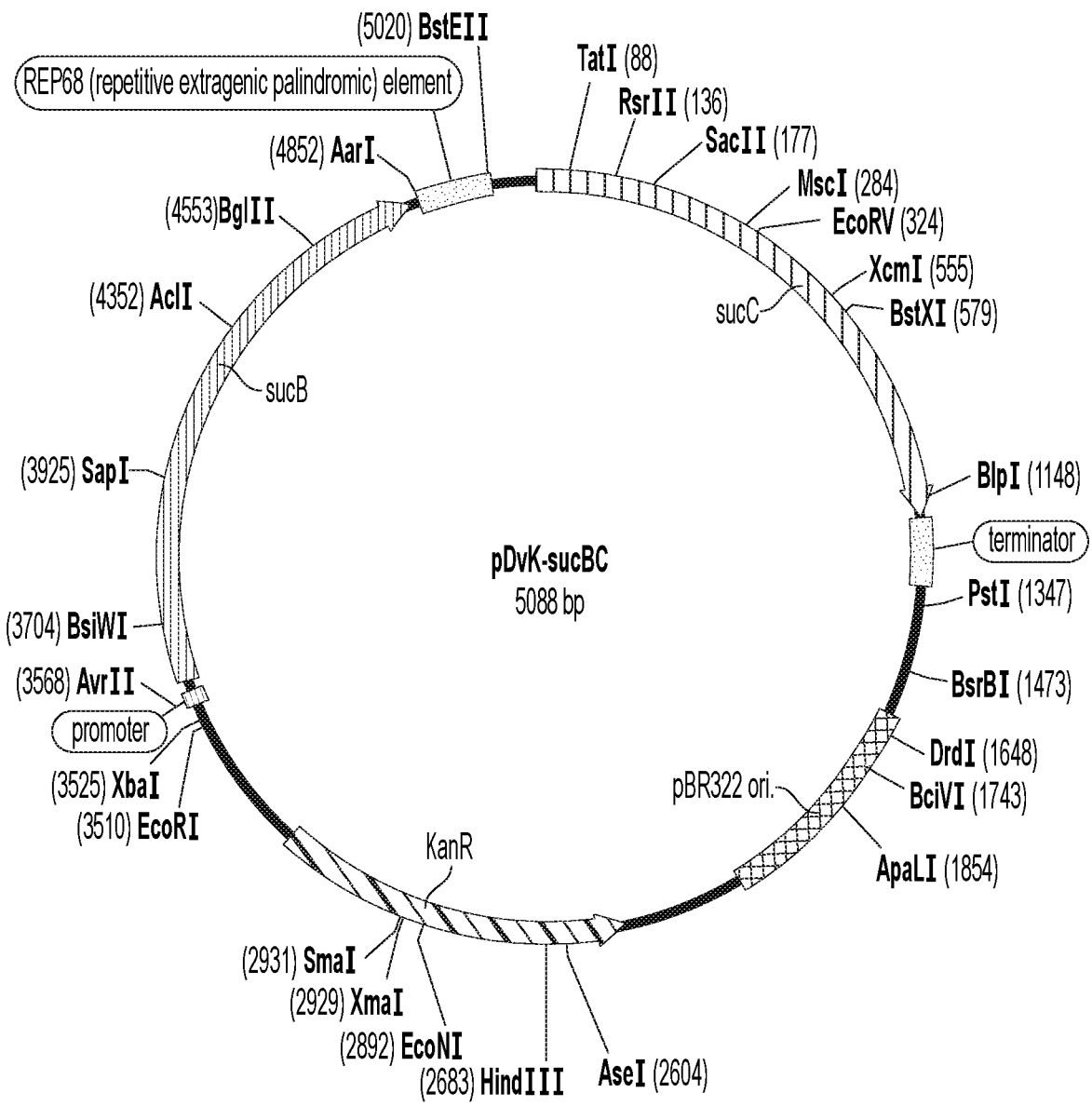

In FIG. 3A, a map of plasmid pDvK-SucAD, according to the current invention is provided. It was used to test for plasmid retention in nonselective media, as hosted in ΔsucAD cells. In this case, the plasmid retains kanamycin resistance markers for later testing. Although promoters, RBS, and terminators are specifically enumerated here, the experiments have shown effectively no difference in expression upon varying these (SEQ ID NO: 4). In FIG. 3B, we provide a map of plasmid pDvK-SucABCD, used to test for plasmid retention in nonselective media, as hosted in ΔsucABCD cells. According to the current invention, the plasmid retains kanamycin resistance markers for later testing. Although promoters, RBS, and terminators are specifically enumerated here, the experiments have shown effectively no difference in expression upon varying these (SEQ ID NO: 5). In FIG. 3C, we see the plasmid map of pDvS-Kan of the invention, wherein the kanamycin resistance marker is easily removed by the gene of interest, and the genes sucAD can instead be used as a selection marker. Although promoters, RBS, and terminators are specifically enumerated here, the experiments have shown effectively no difference in expression upon varying these (SEQ ID NO: 6). In FIG. 3E, a map of plasmid pDvK-SucBC, according to the current invention is provided. It was used to test for plasmid retention in nonselective media, as hosted in ΔsucABCD cells in combination with pDvK-SucAD. In this case, the plasmid retains kanamycin resistance markers for later testing. Although promoters, RBS, and terminators are specifically enumerated here, the experiments have shown effectively no difference in expression upon varying these sequences (SEQ ID NO: 10).

Figure 4A:
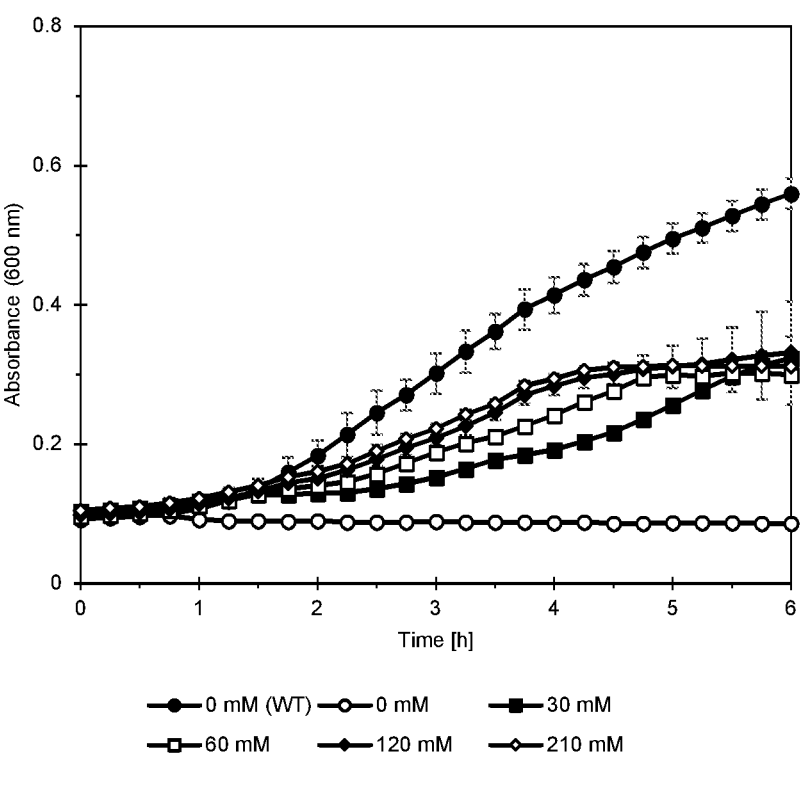
FIGS. 4A-4B. Show succinate pathway knockout mutants, such as BW25113 ΔucAD (FIG. 4A) and BW25113 ΔsucABCD (FIG. 4B), cannot grow on rich fermentation media.
Figure 4B:
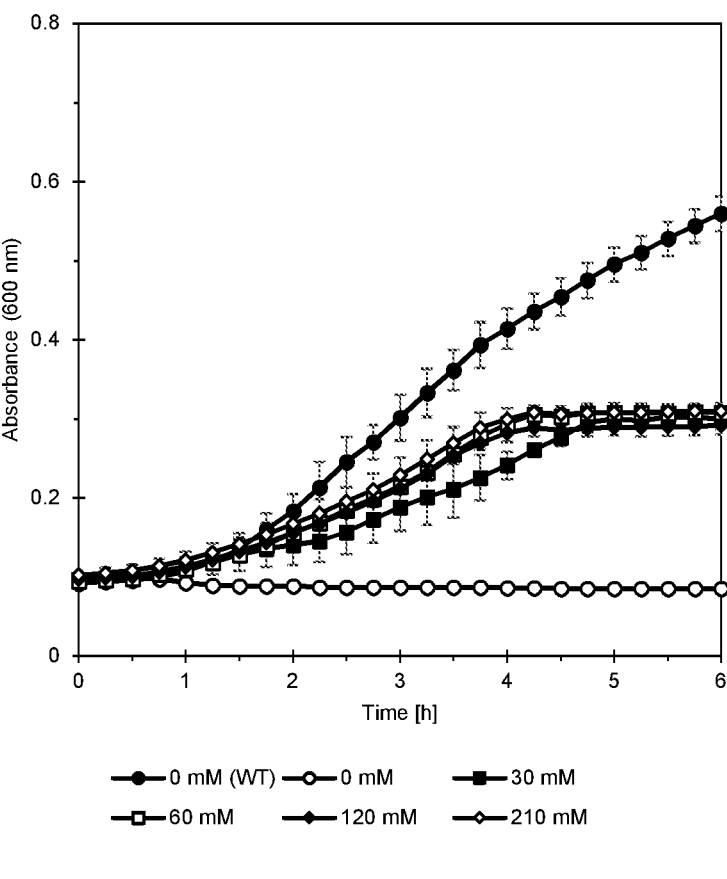

In FIG. 4A, applicants show the succinate pathway knockout mutant BW25113 ΔsucAD cannot grow on rich fermentation media Luria Broth. However, supplanting the media with diaminopimelic acid (DAP) allows for an increase in growth rate, correlating to the concentration of DAP provided. According to the current invention, the plasmid map of pDvQ-Kan is provided in FIG. 3D, wherein the kanamycin resistance marker is easily removed by the gene of interest, and the genes sucABCD can instead be used as a selection marker. Although promoters, RBS, and terminators are specifically enumerated here, the experiments have shown effectively no difference in expression upon varying these (SEQ ID NO: 7). In FIG. 4B, applicants demonstrate that the succinate pathway knockout mutant respectively, rows E-F). 50-mL cultures were grown in LB without kanamycin as selective pressure. Aliquots of cells were plated on kanamycin and non-selective plates and cfu calculated daily. The fraction of KanR cfu over total cfu is reported.

Over time in the absence of kanamycin selection, the cells lacking the deletions lose kanamycin resistance (borne on the plasmids) within a few days, whereas the deletion mutants retain their resistance and their plasmids over the entire course of the study.

TABLE 1

Table of growth characteristics for the retention of a single plasmid in the system. Fraction of cfu that retain kanamycin sensitivity (and thus maintain the plasmid expressing succinate pathway and kanamycin resistance genes) over time.

| Strain | Plasmid | Day | | | | | | | |
|---|---|---|---|---|---|---|---|---|---|
| | | 1 | 2 | 3 | 4 | 5 | 6 | 7 | 8 |
| BW25113 | | 0 | 0 | 0 | 0 | 0 | 0 | 0 | 0 |
| BW25113 ΔsucAD | | 0 | 0 | 0 | 0 | 0 | 0 | 0 | 0 |
| BW25113 ΔsucABCD | | 0 | 0 | 0 | 0 | 0 | 0 | 0 | 0 |
| BW25113 | pDvK-sucAD | <1.0 | 1.35 ± 0.53 | 0.75 ± 0.17 | 0.48 ± 0.03 | 0.09 ± 0.03 | 0.08 ± 0.08 | ~0 | ~0 |
| BW25113 | pDvK-sucABCD | <1.0 | <1.0 | 0.04 ± 0.06 | 0.04 ± 0.00 | 0.16 ± 0.05 | ~0 | ~0 | ~0 |
| BW25113 | pDvK | <1.0 | 0.96 ± 0.12 | 0.63 ± 0.17 | 0.55 ± 0.19 | 0.44 ± 0.15 | 0.50 ± 0.37 | 0.08 ± 0.07 | 0.12 ± 0 15 |
| BW25113 ΔsucAD | pDvK-sucAD | 0.99 ± 0.23 | 1.93 ± 0.12 | 0.84 ± 0.17 | 1.05 ± 0.42 | 1.06 ± 0.04 | 1.30 ± 0.61 | 1.15 ± 0.30 | 1.11 ± 0.19 |
| BW25113 ΔsucABCD | pDvK-sucABCD | 0.86 ± 0.02 | 0.99 ± 0.27 | 0.98 ± 0.17 | 1.26 ± 0.44 | 1.02 ± 0.02 | 0.94 ± 0.21 | 1.23 ± 0.24 | 1.19 ± 0.01 |

BW25113 ΔsucABCD cannot grow on rich fermentation media Luria Broth. However, supplanting the media with diaminopimelic acid (DAP) allows for an increase in growth rate, correlating to the concentration of DAP provided.

Figure 5:
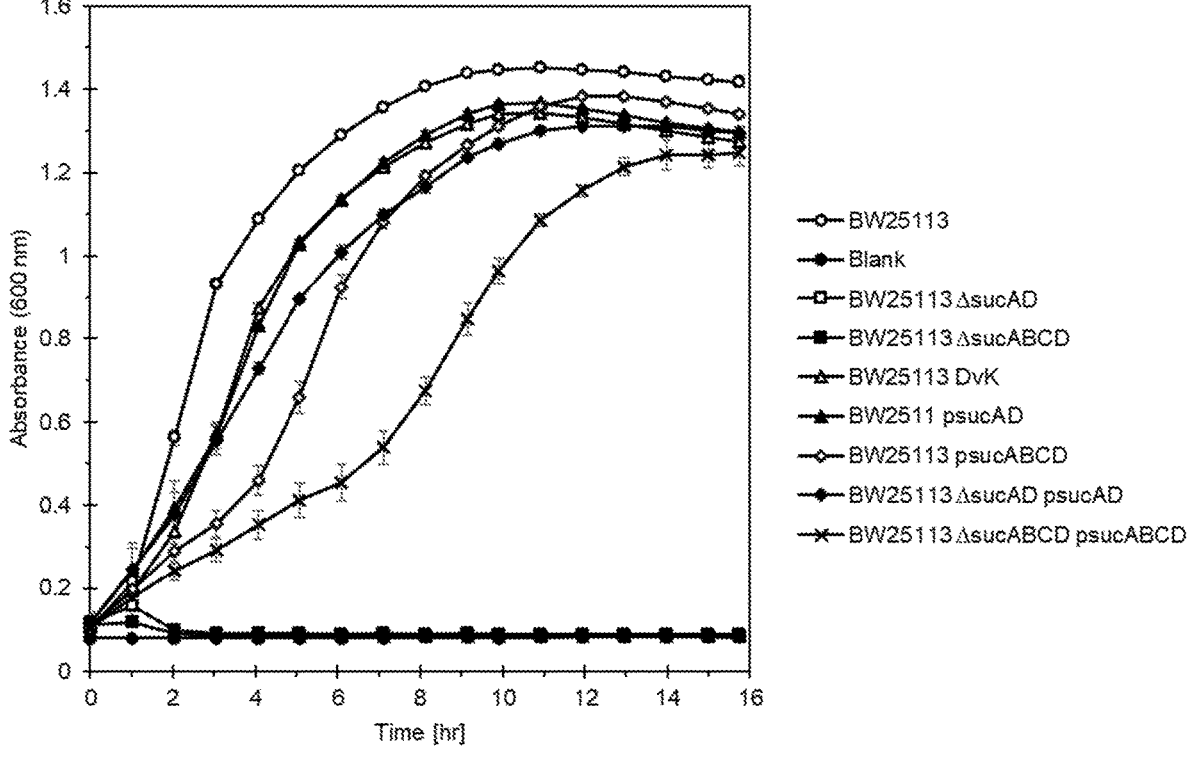
FIG. 5. Growth curves of relevant cells on nonselective media. Shows differences between complementation of double- or quadruple knockouts FIGS. 6A-6B. Plasmid maps of succinate addiction vectors engineered to express GFP. dvp-a8-skb-sfgfp (FIG. 6A); and pDvQ-GFP (FIG. 6B).
Figure 6A:
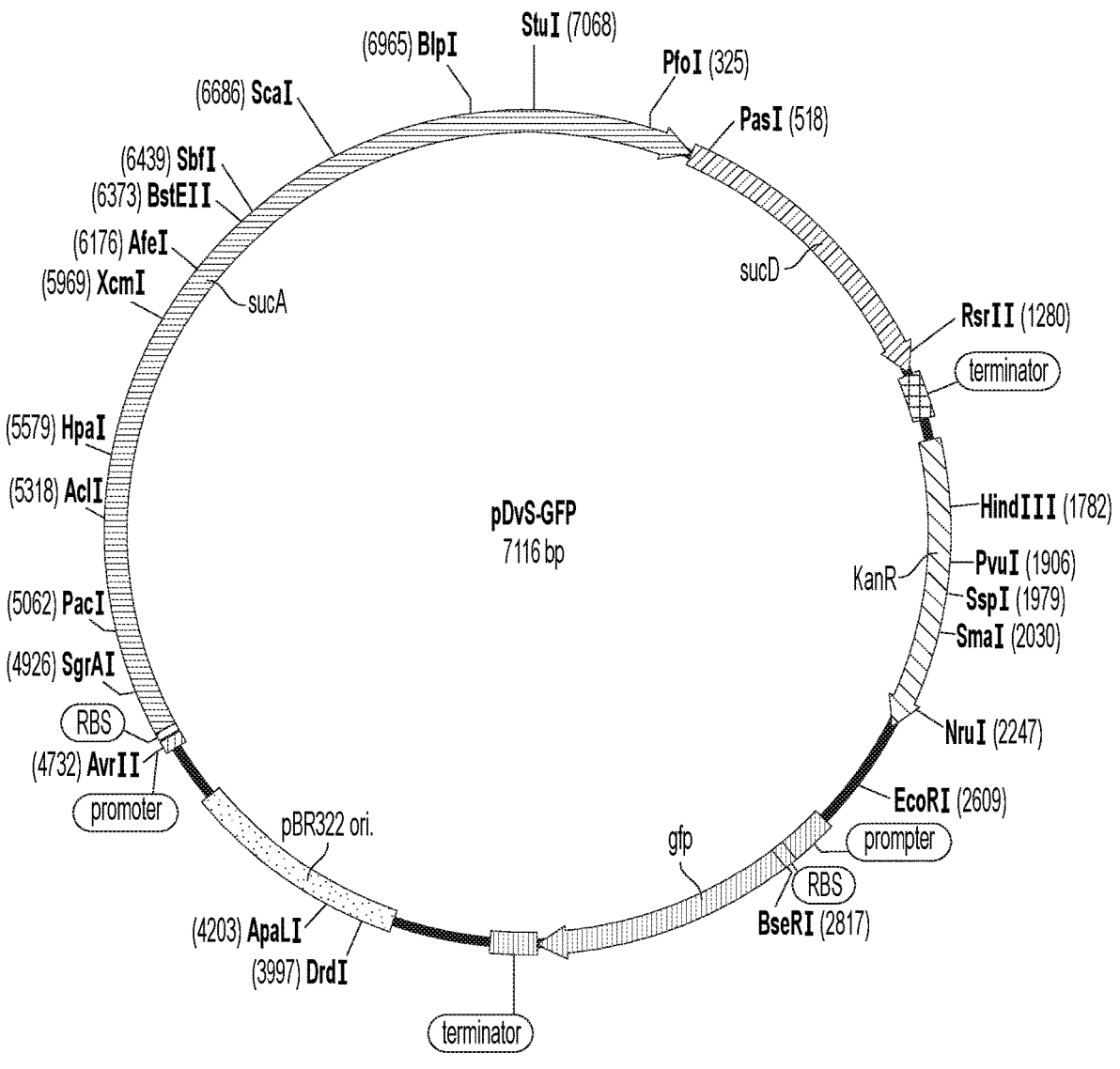
Figure 6B:
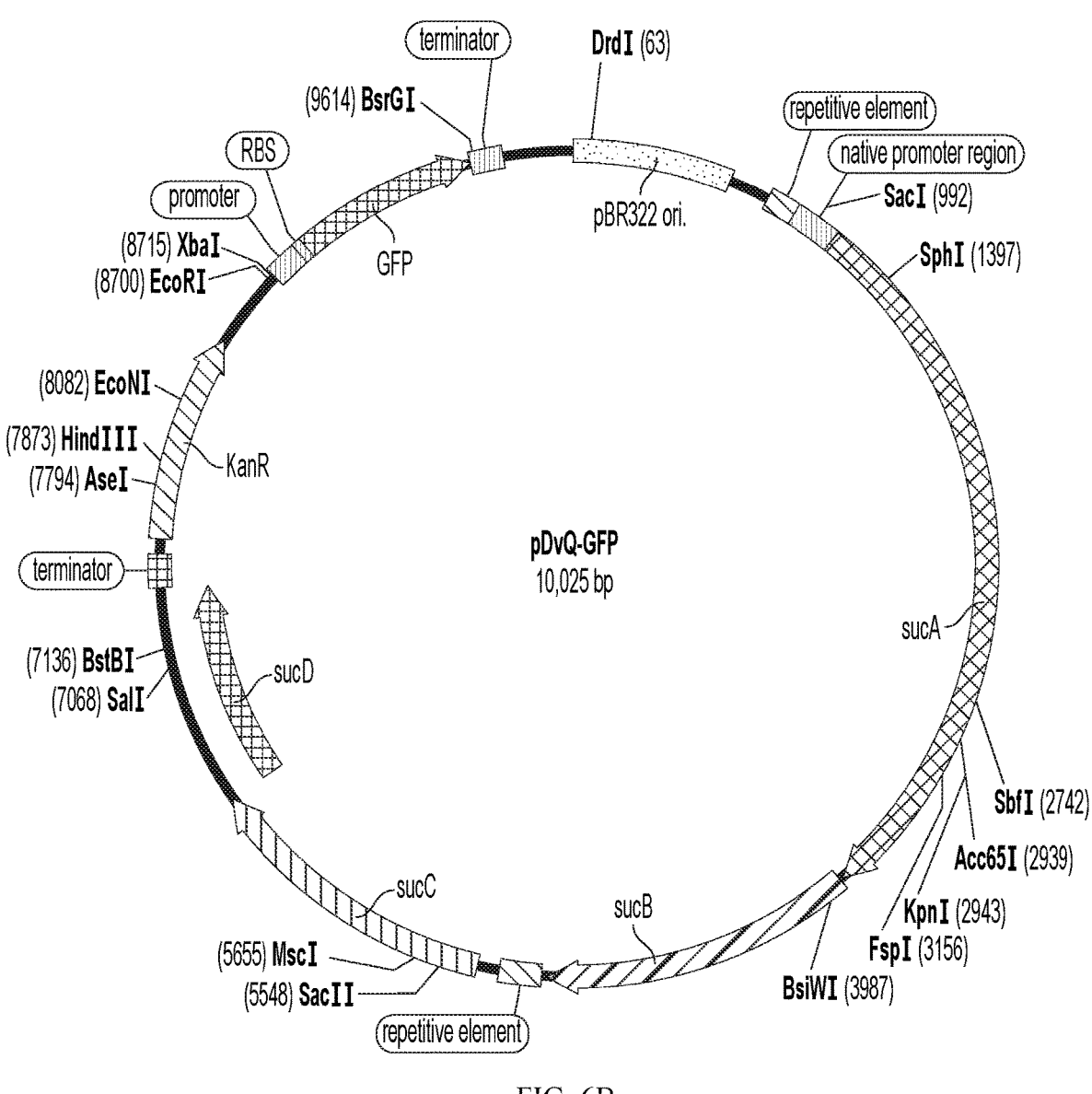
Figure 7:
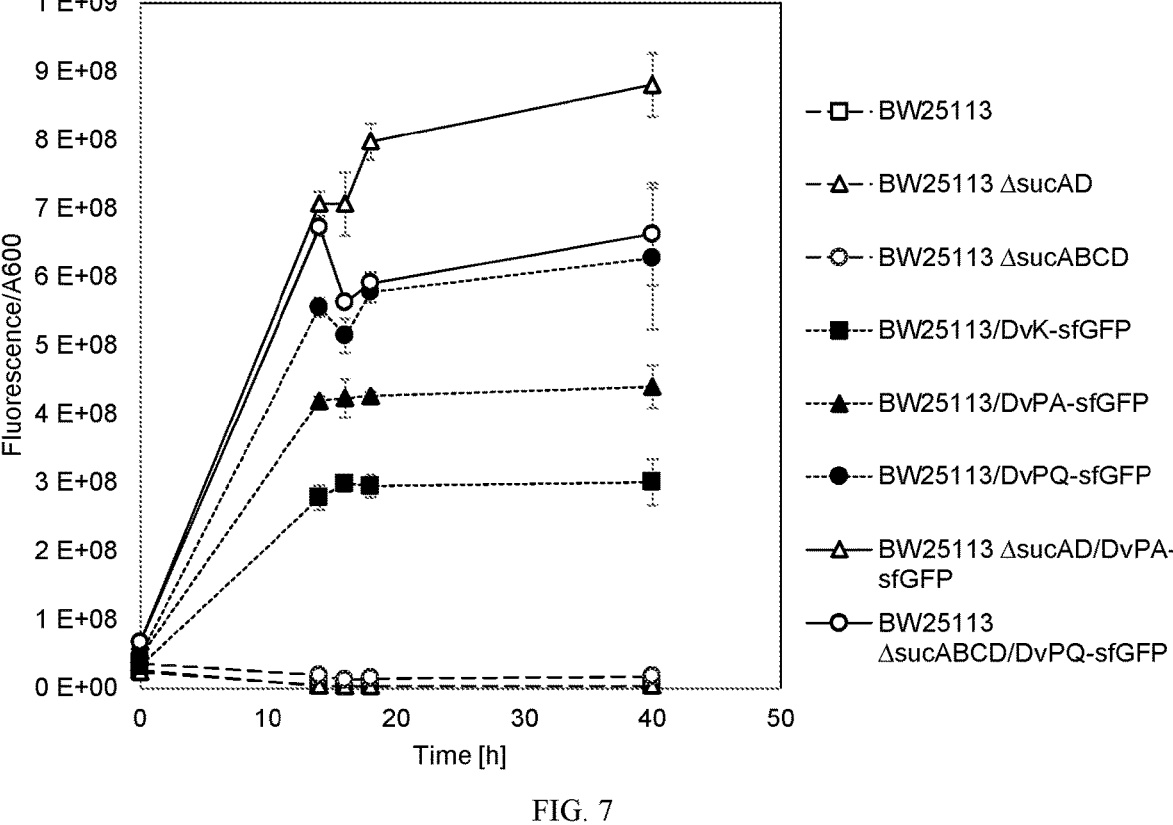
FIG. 7. Shows the production levels of GFP according to the transformed cellular system of the invention.

In FIG. 5, we provide the rescue of growth phenotypes with plasmid-borne sucA(BC)D in artificial operons. Deletions of sucAD and sucABCD from *E. coli* BW25113 do not grow at all on rich fermentation media Luria Broth. However, supplying the cells with plasmids pDvK-SucAD and pDvK-SucABCD, respectively, allows the cells to reach densities of close to that of wild-type BW25113. In FIG. 6A, the plasmid map of pDvS-GFP contains a sequence encoding the green fluorescent protein cloned into the pDvS vector, wherein the kanamycin resistance marker is easily removed by the gene of interest. (SEQ ID NO: 8) is provided. In FIG. 6B, a plasmid map of pDvQ-GFP containing a sequence encoding the green fluorescent protein cloned into the pDvQ vector (SEQ ID NO: 9) is provided. In FIG. 7, we see the production levels of green fluorescent protein (GFP), normalized by cell density according to the transformed cellular system of the invention. The cells containing the deletions and corresponding complements (open symbols, solid lines) exhibit more GFP per unit cell density than those with wild-type backgrounds (filled symbols, dotted lines), or those without plasmids (open symbols, dashed lines). In Table 1 we see that over time in the absence of kanamycin selection, the cells lacking the deletions lose kanamycin resistance (borne on the plasmids) within a few days, whereas the deletion mutants retain their resistance and their plasmids over the entire course of the study.

In addition, in Table 1, Applicants demonstrate that the Fraction of colony forming units (cfu) that retains a KanR plasmid over days. *E. coli* BW25113 was transformed with three Kan resistant plasmids (pDvK-sucAD, pDvK-sucABCD, and pDvK, rows A-D). *E. coli* BW25113 deletions in sucAD and sucABCD were also transformed with complement plasmids (pDvK-sucAD, pDvK-sucABCD, Maintenance of Multiple Plasmids in the System A similar experiment was performed to test the maintenance of multiple plasmids in the system. Cells of BW25113 ΔsucABCD should not be able to grow in LB without supplementation of DAP, unless at least two of the genes sucAB and sucCD are expressed on plasmids. Plasmids pDVK-sucAD and pDVK-sucBC, were constructed. Neither of these plasmids has a sufficient set of genes to allow growth of BW25113 ΔsucABCD without DAP supplementation, but they will in combination. Without supplementation with DAP, the cells retained their kanamycin resistance, and thus their ability to maintain both plasmids (Tables 2, 3).

TABLE 2

Retention of Two-Plasmids. Fraction of cfu that retain kanamycin sensitivity (and thus maintain the plasmids expressing succinate pathway and kanamycin resistance genes) over time.

| Strain | Plasmid(s) | Day 1 |
|---|---|---|
| BW25113 | pDVK | 0.49 ± 0.27 |
| BW25113 ΔsucABCD | pDVK-sucBC and pDVP-sucAD | 0.69 ± 0.37 |

Retention of both plasmids utilized according to the current invention is shown in patch plates, wherein colonies of each strain/plasmid combination were struck on LB agar plates of different media conditions. Only with a complimentary and/or complete set of genes sucAB sucD can *E. coli* BW25113 ΔsucABCD grow without DAP supplementation. Kanamycin resistance shows maintenance of the plasmids, here two, as KanR is linked to the succinate operon genes.

TABLE 3

Retention of Two-Plasmids. Patch growth of plasmids on different media. Cultures of each strain/plasmid were grown in LB + DAP overnight and diluted to $OD_{600}$ = 1.0. Ten µL of this dilution (and serial 50-fold dilutions) were plated onto the media conditions in each column.

| Strain | Plasmid(s) | LB | LB + Kan | LB + DAP | LB + Kan$_{50}$ + DAP |
|---|---|---|---|---|---|
| BW25113 | | ++++ | – | ++++ | – |
| BW25113 ∆sucABCD | | – | – | ++++ | – |
| BW25113 ∆sucABCD | pDVK-sucAD | + | – | ++++ | ++++ |
| BW25113 ∆sucABCD | pDVK-sucBC | – | – | ++++ | ++++ |
| BW25113 ∆sucABCD | pDVK-sucAD and pDVK-sucBC | +++ | +++ | ++++ | +++ |

– = no growth.
+ = growth patch observed with $OD_{600}$ = 1.0 cells.
++ = growth patch observed from 50-fold serial dilution ($OD_{600}$ = 0.02).
+++ = growth patch observed from 2500-fold serial dilution ($OD_{600}$ = 0.0004).
++++ = growth patch observed from 125,000-fold serial dilution ($OD_{600}$ = 0.000008).

Cultivation of Plasmid-Addicted Strains

Plasmid-bearing *E. coli* strains were grown in LB without additional supplementation in 24-well plates and in a Bio-Lector flower plates (Funke et al., 2009).

To achieve tight regulation of toxic gene expression, a tightly regulable promoter like the arabinose-inducible PBAD promoter (Guzman et al., 1995) is preferably used, in particular in the case that the marker protein is per se toxic to the cells.

Another way to control expression of the marker gene is by using constitutive promoters in combination with a gene that is non-toxic (e.g. a reporter gene) or only toxic under defined conditions, e.g. the *Bacillus subtilis* sacB gene, which is only toxic to *E. coli* when sucrose is present.

The promoter is chosen in coordination with the effect of the marker gene product and the required efficiency of down-regulation or silencing effect. For example, for a construct containing a non-toxic or less toxic marker gene, a stronger promoter is desirable.

Additional Embodiments

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials equivalent to or those described herein can be used in the practice or testing of the present disclosure, the preferred methods and materials are described above.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

Accordingly, it is to be understood that the embodiments of the invention herein providing for the production of specific molecules are merely illustrative of the application of the principles of the invention. It will be evident from the foregoing description that changes in the form, methods of use, and applications of the elements of the disclosed production methods and selected microbial strains may be resorted to without departing from the spirit of the invention, or the scope of the appended claims.

STATEMENT OF INDUSTRIAL APPLICABILITY/TECHNICAL FIELD

This disclosure has applicability in the commercial production of food ingredients, fragrances, medicines and pharmaceuticals. This disclosure relates generally to a method for enhanced and more precisely controlled biosynthetic production of desired end products via selected microbial strains.

LITERATURE CITED AND INCORPORATED BY REFERENCE

Baba, T., et al., *Construction of Escherichia coli K*-12 *in-frame, single-gene knockout mutants: the Keio collection*, MOL. SYST. BIOL. 2, 2006.

Balbas, P., et al; *Understanding the Art of Producing Protein and Nonprotein Molecules in Escherichia coli*; MOLECULAR BIOTECHNOLOGY (2001) vol. 19, (3) pp. 251-67.

Balbas, P. et al; *Plasmid vector pBR322 and its special purpose derivatives*—a review; GENE (1986) vol. 50 pp. 3-40.

Beck, C. F. et al; *A Multifunctional Gene (tetR) Controls Tn*10-*encoded Tetracycline Resistance*; JOURNAL OF BACTERIOLOGY (1982) vol. 150 No. 2 pp. 633-42.

Brantl, S., *Antisense RNAs in plasmids: control of replication and maintenance*, Academic Press, PLASMID 48 (2002) pp. 165-173.

Brosius, J., et al, *Construction and Fine Mapping of Recombinant Plasmids Containing the rrnB Ribosomal RNA Operon of E. coli*; PLASMID (1981) vol. 6 No. 1 pp. 112-18.

Chang, A. C. Y., et al., *Construction and Characterization of Amplifiable Multicopy DNA Cloning Vehicles Derived for the P15A Cryptic Miniplasmid*; J. BACTERIOLOGY (1978) vol. 134 No. 3 pp. 1141-56.

Choi Y. J., et al; *Novel, Versatile, and Tightly Regulated Expression System for Escherichia coli Strains.* APPLIED AND ENVIRONMENTAL MICROBIOLOGY (2010) vol 76, No. 15, pp. 5058-66.

Cranenburgh, R. M. et al., *Escherichia coli* strains *that allow antibiotic-free plasmid selection* and *maintenance by repressor titration*, NUCLEIC ACIDS RESEARCH, 2001 vol. 29, No. 5, 1-6.

Datsenko, K. A., and Wanner, B. L., *One-step inactivation of chromosomal genes in Escherichia coii K-12 using PCR products*, Proc. Natl. Acad. Sci. U.S.A 97, 6640-5. (2000)

Deboy, R. T., et al; *Target Site Selection by Tn7: attTn7 Transcription and Target Activity;* Journal of Bacteriology (2000) vol. 182 No. 11 pp. 3310-3313.

Del Solar, Gloria et al., *Replication and Control of Circular Bacterial Plasmids,* Microbiolology and Molecular Biology Reviews (1998) vol. 62, No. 2, pp. 434-64.

Eguchi, Yutaka., et al., *Complexes Formed by Complementary RNA Stem-loops. Their Formation, Structure and Interaction with ColE1 Rom Protein,* Journal Molecular BIOLOGY (1991) vol. 220 pp. 831-842.

Fu X., et al., *Development of a Chromosome-Plasmid Balanced Lethal System of Lactobacillus Acidophilus with thyA Gene as Selective Marker,* Microbiol. Immunol., 44(7) p551-56 (2000).

Funke, M. et al., *The baffled microtiter plate: Increased oxygen transfer and improved online monitoring in small scale fermentations,* Biotechnol. Bioeng. (2009) 103, 1118-28.

Furste, J. P., et al., *Molecular Cloning of the Plasmid RP4 Primase Region in a Multi-Host-Range tacP Expression Vector,* Gene (1986) vol. 48 pp. 119-131.

Gerdes K., et al., *Mechanism of post-segregational killing by the hok/sok system of plasmid R1: sok antisense RNA regulates formation of a hok mRNA species correlated with killing of plasmid-free cells,* Mol. Microbiol. (1990) 4(11): 1807-18.

Gerdes, S. Y., et al., *Experimental Determination and System Level Analysis of Essential Genes in Escherichia coli MG1655,* Journal of Bacteriology (2003) vol. 185 No. 19 pp. 5673-5684.

Haegg, P., et al., A *Host/Plasmid System that is not Dependent on Antibiotics and Antibiotic Genes for Stable Plasmid Maintenance in Escherichia coli.,* JOURNAL OF BIOTECHNOLOGY (2004) vol. 111 pp. 17-30.

Helinski, D. R., et al; *Replication Control and Other Stable Maintenance Mechanisms of Plasmids* (1996) American Society for Microbiology Press, Washington, D.C., pp. 2295-2324.

Hiszczynska-Sawicka, Elzbieta, et al., *Effect of Integration Host Factor on RNA II Synthesis in Replication of Plasmid Containing orip15A,* Plasmid (1998) vol. 40 pp. 150-157.

Herring, Christopher D., et al., *Conditional Lethal Amber Mutations in Essential Escherichia coli Genes,* Journal of Bacteriology (2004) vol. 186, No. 9 pp. 2673-2681.

Jensen, L. Bogo., et al., A *Substrate-Dependent Biological Containment System for Pseudonomas Putida Based on the Escherichia coli gef Gene,* Applied and Environmental Microbiology (1993) vol. 59, No. 11 pp. 3713-3717.

Knudsen, Steen., et al., *Development and Testing of Improved Suicide Functions for Biological Containment of Bacteria,* Applied and Environmental Microbiology (1995) vol. 61, No. 3 pp. 985-991.

Kroll, J., et al., *Plasmid Addiction Systems: Perspectives and Applications in Biotechnology,* Microb. Biotechnol., 3(6) pp 634-57 (2010).

Kues, U., et al., *Replication of Plasmids in Gram-Negative Bacteria,* Microbiological Reviews (1989) vol. 53, No. 4 pp. 491-516.

Mairhofer, Jurgen et al.; A *novel antibiotic free plasmid selection system: Advances in safe and efficient DNA therapy,* Biotechnology Journal (2008) 3, pp. 83-89.

Mattozzi, M. D. et al., *Expression of the sub-pathways of the Chloroflexus aurantiacus 3-hydroxypropionate carbon fixation bicycle in E. coli: Toward horizontal transfer of autotrophic growth,* Metab. Eng. 16, 130-139. (2013).

Merlin, S., et al., *Assessment of Quantitative Models for Plasmid ColE1 Copy Number Control,* J. Mol. Biol. (1995) vol. 248 pp. 211-19.

Michel, Gerhard and Dietmar Schomberg; Metabolic Pathways. (2012) John Wiley and Sons, New York O'Kennedy, R. D., et al., *Effects of Fermentation Strategy on the Characteristics of Plasmid DNA Production,* Biotechnology Appl. Biochem (2003) vol. 37 pp. 83-90.

O'Kennedy, R. D., et al., *Effects of Growth Medium Selection on Plasmid DNA Production and Initial Processing Steps,* Journal of Biotechnology (2000) vol. 76 pp. 175-183.

Postle, K., et al; *Nucleotide Sequence of the Repressor Gene of the TN10 Tetracycline Resistance Determinant;* Nucleic Acids Research (1984) vol. 12, No. 12 pp. 4849-4863.

Pfaffenzeller, I., *Using ColE1-derived RNA I for suppression of a bacterially encoded gene: implication for a novel plasmid addiction system,* Biotech. J. (2006), pp. 1-7.

Rawlings, D. E.; *Protein* Toxin-*Antitoxin, Bacterial Plasmid Addiction Systems* and *their evolution with Special reference to the pas System of pTF-FC2;* FEMS Microbiology Letters (1999) vol. 176 pp. 269-77.

Reinikainen, P., et al; *Escherichia coli Plasmid Production in Fermenter;* Biotechnology Bioengineering (1988) vol. 33 pp. 386-93.

Ronchel, M. Carmen., et al; *Characterization of Cell Lysis in Pseudomonas putida induced Upon Expression of Heterologous Killing Genes,* Applied and Environmental Microbiology, (1998) vol. 64, No. 12 pp. 4904-11.

German L. Rosano and Eduardo A. Ceccarelli, *Recombinant protein expression in Escherichia coli: advances and challenges,* Microbiol. (2014); 5:172.

Schumacher M. A., *Bacterial plasmid partition machinery: a minimalist approach to survival,* Curr Opin Struct Biol., (2012) February; 22(1):72-9

Tomizawa, Jun-Ichi., et al; *Plasmid ColE1 Incompatibility Determined by Interaction of RNA I with Primer Transcript;* Proc. Natl. Acad. Sci. USA (1981) vol. 78, No. 10 pp. 6096-6100.

Tomizawa, Jun-Ichi, *Control of ColE1 Plasmid replication: The Process of Binding of RNA I to the Primer Transcript,* Cell (1984) vol. 38 pp. 861-870.

Tomizawa, Jun-Ichi; *Control of ColE1 Plasmid Replication: Binding of RNA I to RNA II and Inhibition of Primer Formation,* Cell (1986) vol. 47 pp. 89-97.

Torres, B., et al., *As Gene Containment Strategy Based on a Restriction-Modification System,* Environmental Microbiology (2000) vol. 2, No. 5 pp. 555-63.

Vieira, J., et at; *The pUC Plasmids, an M13mp7-Derived System for Insertion Mutagenesis and Sequencing with Synthetic Universal Primers;* Gene (1982) vol. 19 pp. 259-68.

Williams, S. G., et al., *Repressor Titration: A Novel System for Selection and Stable Maintenance of Recombinant Plasmids,* Nucleic Acids Research (1998) vol. 26, No. 9 pp. 2120-24.

Yu., B. J., et al., *sucAB and sucCD are mutually essential genes in Escherichia coli.*, FEMS MICROBIOL. LETT. (2005) 254, 245-50.

Yu, D., et al; *An Efficient Recombination System for Chromosome Engineering in Escherichia coli*; PNAS (2000) vol. 97, No. 11 pp. 5978-83.

What is claimed is:

1. A process for producing a recombinant protein of interest in a transformed bacterial host, comprising:
   a) introducing one or more recombinant plasmids into said bacterial host cell, wherein said one or more recombinant plasmids comprise a cloned DNA sequence comprising all or part of at least two genes each encoding a functional essential succinate pathway enzyme that is integral to the survival of the host cell and the one or more recombinant plasmids also encode at least one gene of interest coding for a protein product, and wherein the one or more recombinant plasmids are devoid of an antibiotic resistance gene;
   b) selecting surviving colonies of the transformed host containing the one or more recombinant plasmids; and,
   c) using the surviving colonies for fermenting bacterial colonies to allow the expression of said protein product; and
   wherein the at least two genes are sucAB and sucCD, and wherein the bacterial host is a mutant with eliminated activity of sucAD or sucABCD.

2. The process of claim 1, wherein the recombinant protein product additionally comprises an amino acid sequence that will optimize purification, isolation or tagging.

3. The process of claim 1, wherein said essential genes are operably linked to a promoter.

4. The process of claim 3, wherein said promoter linked to said essential gene is inducible.

5. The process of claim 4, wherein said inducible promoter is independent of any other inducible promoter controlling a foreign DNA sequence.

6. The process of claim 1, wherein said cell is selected from the group comprising: a *Escherichia coli* cell; *Corynebacterium* spp., *Vibrio* spp.; *Escherichia* spp.; *Enterobacter* spp.; *Citrobacter* spp.; *Erwinia* 0spp.; *Bacillus* spp.; *Pseudomonas* spp.; *Cyanobacteria* spp.; *Salmonella* spp. and *Klebsiella* spp.

7. The process of claim 6, wherein said one or more recombinant plasmids additionally contain a second gene of interest coding for a protein product.

8. The process of claim 1, wherein the one or more recombinant plasmids are two recombinant plasmids.

9. The process of claim 1, wherein the one or more recombinant plasmids are up to four recombinant plasmids.

10. The process of claim 9, wherein the one or more recombinant plasmids are four recombinant plasmids.

*     *     *     *     *

SEQUENCE LISTING

```
Sequence total quantity: 10
SEQ ID NO: 1           moltype = DNA  length = 9001
FEATURE                Location/Qualifiers
source                 1..9001
                       mol_type = genomic DNA
                       organism = Escherichia coli
SEQUENCE: 1
ccggtcaggc actgactgtg aatgagaaag gcgaagatgt ggttgttccg ggactgtttg   60
ccgttggtga aatcgcttgt gtatcggtac acggcgctaa ccgtctgggc ggcaactcgc   120
tgctggacct ggtggtcttt ggtcgcgcgg caggtctgca tctgcaagag tctatcgccg   180
agcagggcgc actgcgcgat gccagcgagt ctgatgttga agcgtctctg gatcgcctga   240
accgctggaa caataatcgt aacggtgaag atccggtggc gatccgtaaa gcgctgcaag   300
aatgtatgca gcataacttc tcggtcttcc gtgaaggtga tgcgatggcg aaagggcttg   360
agcagttgaa agtgatccgc gagcgtctga aaaatgcccg tctggatgac acttccagcg   420
agttcaacac ccagcgcgtt gagtgcctgg aactggataa cctgatggaa acggcgtatg   480
caacggctgt ttctgccaac ttccgtaccg aaagccgtga cgcgcatagc cgcttcgact   540
tcccggatcg tgatgatgaa aactggctgt gccactccct gtatctgcca gagtcggaat   600
ccatgacgcg ccgaagcgtc aacatggaac cgaaactgcg cccggcattc ccgccgaaga   660
ttcgtactta ctaatgcgga gacaggaaaa tgagactcga gttttcaatt tatcgctata   720
acccggatgt tgatgatgct ccgcgtatgc aggattacac cctggaagcg gatgaaggtc   780
gcgacatgat gctgctggat gcgcttatcc agctaaaaga gaaagatccc agcctgtcgt   840
tccgccgctc ctgccgtgaa ggtgtgtgcg gttccgacgg tctgaacatg aacggcaaga   900
atggtctggc ctgtattacc ccgatttcgg cactcaacca gccgggcaag aagattgtga   960
ttcgcccgct gccaggttta ccggtgatcc gcgatttggt ggtagacatg ggacaattct   1020
atgcgcaata tgagaaaatt aagccttacc tgttgaataa tggacaaaat ccgccagctc   1080
gcgagcattt acagatgcca gagcagcgcg aaaaactcga cgggctgtat gaatgtattc   1140
tctgcgcatg ttgttcaacc tcttgtccgt ctttctggtg gaatcccgat aagtttatcg   1200
gcccggcagg cttgttagcg gcatatcgtt tcctgattga tagccgtgat accgagactg   1260
acagccgcct cgacggtttg agtgatgcat tcagcgtatt ccgctgtcac agcatcatga   1320
actgcgtcag tgtatgtccg aaggggctga acccgacgcg cgccatcggc catatcaagt   1380
cgatgttgtt gcaacgtaat gcgtaaaccg taggcctgat aagacgcgca agcgtcgcat   1440
caggcaacca gtgccggatg cggcgtgaac gccttatccg gcctacaagt cattacccgt   1500
aggcctgata agcgcagcgc atcaggcgta acaaagaaact gcaggaaatc tttaaaaact   1560
gcccctgaca ctaagacagt tttttaaaggt tccttcgcga gccactacgt agacaagagc   1620
tcgcaagtga accccggcac gcacatcact gtgcgtggta gtatccacgg cgaagtaagc   1680
ataaaaaaga tgcttaaggg atcacgatgc agaacagcgc tttgaaagcc tggttggact   1740
cttcttacct ctctggcgca aaccagagct ggatagaaca gctctatgaa gacttcttaa   1800
ccgatcctga ctcggttgac gctaactggc gttcgacgtt ccagcagtta cctggtacgg   1860
gagtcaaacc ggatcaattc cactctcaaa cgcgtgaata tttccgccgc ctggcgaaag   1920
acgcttcacg ttactcttca acgatctccg accctgacac caatgtgaag caggttaaag   1980
tcctgcagct cattaacgca taccgcttcc gtggtcacca gcatgcgaat ctcgatccgc   2040
tgggactgtg gcagcaagat aaagtggccg atctggatcc gtctttccac gatctgaccg   2100
aagcagactt ccaggagacc ttcaacgtcg gttcatttgc cagcggcaaa gaaaccatga   2160
aactcggcga gctgctggaa gccctcaagc aaacctactg cggcccgatt ggtgccgagt   2220
atatgcacat taccagcacc gaagaaaaac gctggatcca acagcgtatc gagtctggtc   2280
gcgcgacttt caatagcgaa gagaaaaaac gcttcttaag cgaactgacc gccgctgaag   2340
gtcttgaacg ttacctcggc gcaaaattcc ctggcgcaaa acgcttctcg ctggaaggcg   2400
gtgacgcgtt aatcccgatg cttaaagaga tgatccgcca cgctggcaac agcggcaccc   2460
gcgaagtggt tctcgggatg gcgcaccgtg gtcgtctgaa cgtgctggtg aacgtgctgg   2520
gtaaaaaacc gcaagacttg ttcgacgagt tcgccggtaa acatcaaagaa cacctcggca   2580
cgggtgacgt gaaataccac atgggcttct cgtctgactt ccagaccgat ggcggcctgg   2640
tgcacctggc gctggcgttt aacccgtctc accttgagat tgtaagcccg gtagttatcg   2700
gttctgttcg tgcccgtctg gacagacttg atgagccgag cagcaacaaa gtgctgccaa   2760
tcaccatcca cggtgacgcc gcagtgaccg ggcagggcgt ggttcaggaa accctgaaca   2820
tgtcgaaagc gcgtggttat gaagttggcg gtacggtacg tatcgttatc aacaaccagg   2880
ttggtttcac cacctctaat ccgctggatg cccgttctac gccgtactgt actgatatcg   2940
gtaagatggt tcaggccccg attttccacg ttaacgcgga cgatccggaa gccgttgcct   3000
ttgtgacccg tctggcgctc gatttccgta cacctttaa acgtgatgtc ttcatcgacc   3060
tggtgtgcta ccgccgtcac ggccacaacg aagccgacga gccgagcgca acccagccgc   3120
tgatgtatca gaaaatcaaa aaacatccga caccgcgcaa aatctacgct gacaagctgg   3180
agcaggaaaa agtggcgacg ctggaagatg ccaccgagat ggttaacctg taccgcgatg   3240
cgctggatgc tggcgattgc gtagtggcag agtggcgtcc gatgaacatg cactctttca   3300
cctggtcgcc gtacctcaac cacgaatggg acgaagagta cccgaacaaa gttgagatga   3360
agcgcctgca ggagctggcg aaacgcatca gcacggtgcc ggaagcagtt gaaatgcagt   3420
ctcgcgttgc caagatttat ggcgatcgcc aggcgatggc tgccggtgag aaaactgttcg   3480
actggggcgg tgcggaaaac ctcgcttacg ccacgctggt tgatgaaggc attccggttc   3540
gcctgtcggg tgaagactcc ggtcgcggta ccttcttcca ccgccacgcg gtgatccaca   3600
accagtctaa cggttccact tacacgccgc tgcaacatat ccataaccggg cagggcgcgt   3660
tccgtgtctg ggactccgta ctgtctgaag aagcagtcgt ggcgtttgaa tatggcgtat   3720
ccaccgcaga accacgcact ctgaccatct gggaagcgca gttcggtgac ttcgccaacg   3780
gtgcgcaggt ggttatcgac cagttcatct cctctggcga acagaaatgg ggccggatgt   3840
gtggtctggt gatgttgctg ccgcacggtt acgaagggca ggggccggag cactcctccg   3900
cgcgtctgga acgttatctg caactttgtg ctgagcaaaa catgcaggtt tgcgtaccgt   3960
```

```
ctaccccggc acaggtttac cacatgctgc gtcgtcaggc gctgcgcggg atgcgtcgtc 4020
cgctggtcgt gatgtcgccg aaatccctgc tgcgtcatcc gctggcggtt tccagcctcg 4080
aagaactggc gaacggcacc ttcctgccag ccatcggtga aatcgacgag cttgatccga 4140
agggcgtgaa gcgcgtagtg atgtgttctg gtaaggttta ttacgacctg ctggaacagc 4200
gtcgtaagaa caatcaacac gatgtcgcca ttgtgcgtat cgagcaactc tacccgttcc 4260
cgcataaagc gatgcaggaa gtgttgcagc agtttgctca cgtcaaggat tttgtctggt 4320
gccaggaaga gccgctcaac cagggcgcat ggtactgcag ccagcatcat ttccgtgaag 4380
tgattccgtt tggggcttct ctgcgttatg caggccgccc ggcctccgcc tctccggcgg 4440
tagggtatat gtccgttcac cagaaacagc aacaagatct ggttaatgac gcgctgaacg 4500
tcgaataaat aaaggataca caatgagtag cgtagatatt ctggtccctg acctgcctga 4560
atccgtagcc gatgccaccg tcgcaacctg gcataaaaaa cccggcgacg cagtcgtacg 4620
tgatgaagtg ctggtagaaa tcgaaactga caaagtggta ctggaagtac cggcatcagc 4680
agacggcatt ctggatgcgg ttctggaaga tgaaggtaca acggtaacgt ctcgtcagat 4740
ccttggtcgc ctgcgtgaag gcaacagcgc cggtaaagaa accagcgcca aatctgaaga 4800
gaaagcgtcc actccggcgc aacgccagca ggcgtctctg gaagagcaaa acaacgatgc 4860
gttaagcccg gcgatccgtc gcctgctggc tgaacacaat ctcgacgcca gcgccattaa 4920
aggcaccggt gtgggtggtc gtctgactcg tgaagatgtg gaaaaacatc tggcgaaagc 4980
cccggcgaaa gagtctgctc cggcagcggc tgctccggcg gcgcaaccgg ctctggctgc 5040
acgtagtgaa aaacgtgtcc cgatgactcg cctgcgtaag cgtgtggcag agcgtctgct 5100
ggaagcgaaa aactccaccg ccatgctgac cacgttcaac gaagtcaaca tgaagccgat 5160
tatggatctg cgtaagcagt acggtgaagc gtttgaaaaa cgccacggca tccgtctggg 5220
ctttatgtcc ttctacgtga aagcgtggt tgaagcccta aaacgttacc cggaagtgaa 5280
cgcttctatc gacggcgatg acgtggttta ccacaactat ttcgacgtca gcatggcggt 5340
ttctacgccg cgcggcctgg tgacgccggt tctgcgtgat gtcgatacct cggcatggc 5400
agacatcgag aagaaaatca aagagctggc agtcaaaggc cgtgacggca agctgaccgt 5460
tgaagatctg accggtggta acttcaccat caccaacggt ggtgtgttcg gttccctgat 5520
gtctacgccg atcatcaacc cgccgcagag cgcaattctg ggtatgcacg ctatcaaaga 5580
tcgtccgatg gcggtgaatg gtcaggttga gatcctgccg atgatgtacc tggcgctgtc 5640
ctacgatcac cgtctgatcg atggtcgcga atccgtgggc ttcctggtaa cgatcaaaga 5700
gttgctggaa gatccgacgc gtctgctgct ggacgtgtag tagtttaagt ttcacctgca 5760
ctgtagaccg gataaggcat tatcgccttc tccggcaatt gaagcctgat gcgacgctga 5820
cgcgtcttat caggcctacg ggaccaccaa tgtaggtcgg ataaggcgca agcgccgcat 5880
ccgacaagcg atgcctgatg tgacgtttaa cgtgtcttat caggcctacg ggtgaccgac 5940
aatgcccgga agcgatacga aatattcggt ctacggttta aaagataacg attactgaag 6000
gatggacaga acacatgaac ttacatgaat atcaggcaaa acaactttt gcccgctatg 6060
gcttaccagc accggtgggt tatgcctgta ctactccgcg cgaagcagaa gaagccgctt 6120
caaaaatcgg tgccggtccg tgggtagtga aatgtcaggt tcacgctggt ggccgcggta 6180
aagcgggcgg tgtgaaagtt gtaaacagca aagaagacat ccgtgctttt gcagaaaact 6240
ggctggcgcaa gcgtctggta acgtatcaaa cagatgccaa tggccaaccg gttaaccaga 6300
ttctggttga agcagcgacc gatatcgcta aagagctgta tctcggtgcc gttgttgacc 6360
gtagttcccg tcgtgtggtc tttatggcct ccaccgaagg cggcgtggaa atcgaaaaag 6420
tggcggaaga aactccgcac ctgatccata aagttgcgct tgatccgctg actggcccga 6480
tgccgtatca gggacgcgag ctggcgttca aactgggtct ggaaggtaac ctggttcagc 6540
agttcaccaa aatcttcatg ggcctggcga ccatttttcct ggagcgcgac ctggcgttga 6600
tcgaaatcaa cccgctggtc atcaccaaac agggcgatct gatttgcctc gacggcaaac 6660
tgggcgctga cggcaacgca ctgttccgcc agcctgatct gcgcgaaatg cgtgaccagt 6720
cgcaggaaga tccgcgtgaa gcacaggctg cacgtgagaa actgaactac gttgcgctgg 6780
acggtaacat cggttgtatg gttaacggcg caggtctggc gatgggtacg atggacatcg 6840
ttaaactgca cggcggcgaa ccggctaact tccttgacgt tggcggcggc gcaaccaaag 6900
aacgtgtaac cgaagcgttc aaaatcatcc tctctgacga caaagtgaaa gccgttctgg 6960
ttaacatctt cggcggtatc gttcgttgcg acctgatcgc tgaccgtatc atcggcgagt 7020
tagcagaagt gggtgttaac gtaccggtcg tggtacgtct ggaaggtaac aacgccgaac 7080
tcggcgcgaa gaaactggct gacagcggcc tgaatattat tgcagcaaaa ggtctgacgg 7140
atgcagctca gcaggttgtt gccgcagtgg aggggaaata atgtccattt taatcgataa 7200
aaacaccaag gttatctgcc agggcttac cggtagccag gggactttcc actcagaaca 7260
ggccattgca tacggcacta aaatggttgg cggcgtaacc ccaggtaaag gcggcaccac 7320
ccacctcggc ctgccggtgt tcaacaccgt gcgtgaagcc gttgctgcca ctggcgctac 7380
cgcttctgtt atctacgtac cagcaccgtt ctgcaaagac tccattctgg aagccatcga 7440
cgcaggcatc aaactgatta tcaccatcac tgaaggcatc ccgacgctgg atatgctgac 7500
cgtgaaagtg aagctggatg aagcaggcgt tcgtatgatc ggcccgaact gcccaggcgt 7560
tatcactccg ggtgaatgca aaatcggtat ccagcctggt cacattcaca aaccgggtaa 7620
agtgggtatc gtttcccgtt ccggtacact gacctatgaa gcggttaaac agaccacgga 7680
ttacggtttc ggtcagtcga cctgtgtcgg tatcggcggg gacccgatcc cgggctctaa 7740
ctttatcgac attctcgaaa tgttcgaaaa agatccgcag accgaagcga tcgtgatgat 7800
cggtgagatc ggcggtagcg ctgaagaaga agcagctgcg tacatcaaag agcacgttac 7860
caagccagtt gtgggttaca tcgctggtgt gactgcgccg aaaggcaaac gtatgggcca 7920
cgcgggtgcc atcattgccg gtgggaaagg gactgcggat gagaaattcg ctgctctgga 7980
agccgcaggc gtgaaaaccg ttcgcagcct ggcggatatc ggtgaagcac tgaaaactgt 8040
tctgaaataa atatctgtaa taagaaatag ccctcgccgc ttccctctac aggaatgcgg 8100
aagggctgtc ggtttcgaca tggttggcca tcgtatgatg gcctttttg tgcttatcgc 8160
gatgattttc gctgcgctat cagggtaaat ttatagtcat cggtattaaa agcgttgcgg 8220
ctatattcaa acacccgacc atcaactaaa tatccacgcg atactttttc aagaatcggc 8280
tttgtctggc tgatattaag cagacggctc atctcttcgg ttggcatcag aggaatgatt 8340
tcctgttcgc tacgatcgat aaccattttc ttcacttctt cgataaagtg atatttcgaa 8400
ttttccatga cctgccaggt gagatccggg aacaacgcaa gcggcatcca ggtttcttcc 8460
agcgccattg gcttttgctt gcgatagcgc acgcgcttca catgccacac acgatcctgc 8520
ggggtgattt gtagctgttg ctgaagaaaa tcgtcagccg gaatcacttc gaatatcaga 8580
acttcactgt gtgtatcgac gtgacggtcc gacagttttt catcaaaact ggttaactga 8640
aaaatatcgt aattgacccg ctcttctttg acgtaagtcc cgctgccctg aatgctttcg 8700
```

```
aggatctgct gctcgactag ctggcgcaaa gcctgacgca ccgtaacccg gctgacgcca    8760
aactctgttt gtagcgctga ttcagtgggg aacgcatcgc caggtttaag ctcgccacgc    8820
gcaatttgtt cacgaatgcg atcggcaatc tgccggtata agggcttgtg tcccattttt    8880
agtatctcat taatacgaat ttaaccatta tgcccgataa attcatcctg taaataatac    8940
aaatacaata caaataattt caatcaagtg aaattgatca cataatggta ttgttttatc    9000
g                                                                     9001
```

```
SEQ ID NO: 2              moltype = DNA   length = 6753
FEATURE                   Location/Qualifiers
source                    1..6753
                          mol_type = genomic DNA
                          organism = Escherichia coli
SEQUENCE: 2
ccggtcaggc actgactgtg aatgagaaag gcgaagatgt ggttgttccg ggactgtttg    60
ccgttggtga aatcgcttgt gtatcggtac acggcgctaa ccgtctgggc ggcaactcgc    120
tgctggacct ggtggtcttt ggtcgcgcgg caggtctgca tctgcaagag tctatcgccg    180
agcagggcgc actgcgcgat gccagcgagt ctgatgttga agcgtctctg gatcgcctga    240
accgctggaa caataatcgt aacggtgaag atccggtggc gatccgtaaa gcgctgcaag    300
aatgtatgca gcataacttc tcggtcttcc gtgaaggtga tgccgatggcg aaagggcttg    360
agcagttgaa agtgatccgc gagcgtctga aaaatgcccg tctggatgac acttccagcg    420
agttcaacac ccagcgcgtt gagtgcctgg aactggataa cctgatggaa acggcgtatg    480
caacggctgt ttctgccaac ttccgtaccg aaagccgtgg cgcgcatagc cgcttcgact    540
tcccggatcg tgatgatgaa aactggctgt gccactccct gtatctgcca gagtcggaat    600
ccatgacgcg ccgaagcgtc aacatggaac cgaaactgcg cccggcattc ccgccgaaga    660
ttcgtactta ctaatgcgga gacaggaaaa tgagactcga gttttcaatt tatcgctata    720
acccggatgt tgatgatgcc ccgcgtatgc aggattacac cctggaagcg gatgaaggtc    780
gcgacatgat gctgctggat gcgcttatcc agctaaaaga gaaagatccc agcctgtcgt    840
tccgccgctc ctgccgtgaa ggtgtgtgcg gttccgacgg tctgaacatg aacggcaaga    900
atggtctggc ctgtattacc ccgatttcgg cactcaacca gccgggcaag aagattgtga    960
ttcgccgct gccaggttta ccggtgatcc gcgatttggt ggtagacatg ggacaattct    1020
atgcgcaata tgagaaaatt aagccttacc tgttgaataa tggacaaaat ccgccagctc    1080
gcgagcattt acagatgcca gagcagcgcg aaaaactcga cgggctgtat gaatgtattc    1140
tctgcgcatg ttgttcaacc tcttgtccgt cttttctggtg gaatcccgat aagtttatcg    1200
gcccggcagg cttgttagcg gcatatcgtt tcctgattga tagccgtgat accgagactg    1260
acagccgcct cgacggtttg agtgatgcat tcagcgtatt ccgctgtcac agcatcatga    1320
actgcgtcag tgtatgtccg aaggggctga acccgacgcg cgccatcggc catatcaagt    1380
cgatgttgtt gcaacgtaat gcgtaaaccg taggcctgat aagacgcgca agcgtcgcat    1440
caggcaacca gtgccggatg cggcgtgaac gccttatccg gcctacaagt cattacccgt    1500
aggcctgata agcgcagcgc atcaggcgta acaaagaaat gcaggaaatc tttaaaaact    1560
gcccctgaca ctaagacagt ttttaaaggt tccttcgcga gccactacgt agacaagagc    1620
tcgcaagtga accccggcac gcacatcact gtgcgtggta gtatccacgg cgaagtaagc    1680
ataaaaaga tgcttaaggg atcacgagtg taggctggag ctgcttcgaa gttcctatac    1740
tttctagaga ataggaactt cggaatagga acttcaagat ccccttatta gaagaactcg    1800
tcaagaaggc gatagaaggc gatgcgctgc gaatcgggag cggcgatacc gtaaagcacg    1860
aggaagcggt cagcccattc gccgccaagc tcttcagcaa tatcacgggt agccaacgct    1920
atgtcctgat agcggtccgc cacacccagc cggccacagt cgatgaatcc agaaaagcgg    1980
ccattttcca ccatgatatt cggcaagcag gcatcgccat gggtcacgac gagatcctcg    2040
ccgtcgggca tgcgcgcctt gagcctggcg aacagttcgg ctggcgcgag cccctgatgc    2100
tcttcgtcca gatcatcctg atcgacaaga ccggcttcca tccgagtacg tgctcgctcg    2160
atgcgatgtt tcgcttggtg gtcgaatggg caggtagccg gatcaagcgt atgcagccgc    2220
cgcattgcat cagccatgat ggatactttc tcggcaggag caaggtgaga tgacaggaga    2280
tcctgccccg gcacttcgcc caatagcagc cagtcccttc ccgcttcagt gacaacgtcg    2340
agcacagctg cgcaaggaac gcccgtcgtg gccagccacg atagccgcgc tgcctcgtcc    2400
tgcagttcat tcagggcacc ggacaggtcg gtcttgacaa aaagaaccgg gcgcccctgc    2460
gctgacagcc ggaacacggc ggcatcagag cagccgattg tctgttgtgc ccagtcatag    2520
ccgaatagcc tctccaccca gcgggccgga gaacctgcgt gcaatccatc ttgttcaatc    2580
atgcgaaacg atcctcatcc tgtctcttga tcagatcttg atccctgcg ccatcagatc    2640
cttggcggca agaaagccat ccagtttact ttgcagggct tcccaacctt accagagggc    2700
gccccagctg gcaattccgg ttcgcttgct gtccataaaa ccgcccagtc tagctatcgc    2760
catgtaagcc cactgcaagc tacctgcttt ctctttgcgc ttgcgttttc ccttgtccag    2820
atagcccagt agctgacatt catccggggt cagcaccgtt tctgcggact ggctttctac    2880
gtgttccgct tcctttagca gcccttgcgc cctgagtgct tgcggcagcg tgagcttcaa    2940
aagcgctctg aagttcctat actttctaga aataggaac ttcgaactgc aggtcgacgg    3000
atcccggaa ttaattctca tgtttgacag aaaggatacc caatgagtag cgtagatatt    3060
ctggtccctg acctgcctga atccgtagcc gatgccaccg tcgcaacctg gcataaaaaa    3120
cccggcgacg cagtcgtacg tgatgaagtg ctggtagaaa tcgaaactga caaagtggta    3180
ctggaagtac cggcatcagc agacggcatt ctggatgcgg ttctggaaga tgaaggtaca    3240
acggtaacgt ctcgtcagat ccttggtcgc ctgcgtgaag caacagcgc cggtaaagaa    3300
accagcgcca aatctgaaga gaaagcgtcc actccggcgc aacgccagca ggcgtctctg    3360
gaagagcaaa acaacgatgc gttaagcccg cgatccgtc gcctgctggc tgaacacaat    3420
ctcgacgcca cgcccattaa aggcaccggt gtgggtggtc gtctgactcg tgaagatgtg    3480
gaaaacatc tggcgaaagc cccggcgaaa gagtctgctc cggcagcggc tgctccggcg    3540
gcgcaaccgg ctctggctgc acgtagtgaa aaacgtgtcc cgatgactcg cctgcgtaag    3600
cgtgtggcag agcgtctgct ggaagcgaaa aactccaccg ccatgctgac cacgttcaac    3660
gaagtcaaca tgaagccgat tatggatctg cgtaagcagt acggtgaagc gtttgaaaaa    3720
cgccacggca tccgtctggg cttttatgtc ttctacgtga agcggtggt tgaagccctg    3780
aaacgttacc cggaagtgaa cgcttctatc gacggcgatg acgtggttta ccacaactat    3840
ttcgacgtca gcatggcggt ttctacgccg cgcggctgg tgacgccggt tctgcgtgat    3900
gtcgataccc tcggcatggc agacatcgag aagaaaatca agagctggc agtcaaaggc    3960
```

-continued

```
cgtgacggca agctgaccgt tgaagatctg accggtggta acttcaccat caccaacggt  4020
ggtgtgttcg gttccctgat gtctacgccg atcatcaacc cgccgcagag cgcaattctg  4080
ggtatgcacg ctatcaaaga tcgtccgatg gcggtgaatg gtcaggttga gatcctgccg  4140
atgatgtacc tggcgctgtc ctacgatcac cgtctgatcg atggtcgcga atccgtgggc  4200
ttcctggtaa cgatcaaaga gttgctggaa gatccgaccg gtctgctgct ggacgtgtag  4260
tagtttaagt ttcacctgca ctgtagaccg gataaggcat tatcgccttc tccggcaatt  4320
gaagcctgat gcgacgctga cgcgtcttat caggcctacg ggaccaccaa tgtaggtcgg  4380
ataaggcgca agcgccgcat ccgacaagcg atgcctgatg tgacgtttaa cgtgtcttat  4440
caggcctacg ggtgaccgac aatgcccgga agcgatacga aatattcggt ctacggttta  4500
aaagataacg attactgaag gatggacaga acacatgaac ttacatgaat atcaggcaaa  4560
acaactttttt gcccgctatg gcttaccagc accggtgggt tatgcctgta ctactccgcg  4620
cgaagcagaa gaagccgctt caaaaatcgg tgccggtccg tgggtagtga aatgtcaggt  4680
tcacgctggt ggccgcggta aagcgggcgg tgtgaaagtt gtaaacagca aagaagacat  4740
ccgtgctttt gcagaaaact ggctgggcaa gcgtctggta acgtatcaaa cagatgccaa  4800
tggccaaccg gttaaccaga ttctggttga agcagcgacc gatatcgcta aagagctgta  4860
tctcggtgcc gttgttgacc gtagttcccg tcgtgtggtc tttatggcct ccaccgaagg  4920
cggcgtggaa atcgaaaaag tggcggaaga aactccgcac ctgatccata aagttgcgct  4980
tgatccgctg actggcccga tgccgtatca gggacgcgag ctggcgttca aactgggtct  5040
ggaaggtaaa ctggttcagc agttcaccaa aatcttcatg ggcctggcga ccattttcct  5100
ggagcgcgac ctggcgttga tcgaaatcaa cccgctggtc atcaccaaac agggcgatct  5160
gatttgcctc gacggcaaac tgggcgctga cggcaacgca ctgttccgcc agcctgatct  5220
gcgcgaaatg cgtgaccagt cgcaggaaga tccgcgtgaa gcacaggctg cacagtggga  5280
actgaactac gttgcgctgg acggtaacat cggttgtatg gttaacggcg caggtctggc  5340
gatgggtacg atggacatcg ttaaaactgca cggcggcgaa ccggctaact tccttgacgt  5400
tggcggcggc gcaaccaaag aacgtgtaac cgaagcgttc aaaatcatcc tctctgacga  5460
caaagtgaaa gccgttctgg ttaacatctt cggcggtatc gttcgttgcg acctgatcgc  5520
tgacggtatc atcggcgcgg tagcagaagt gggtgttaac gtaccggtcg tggtacgtct  5580
ggaaggtaac aacgccgaac tcggcgcgaa gaaactggct gacagcggcc tgaatattat  5640
tgcagcaaaa ggtctgacgg atgcagctca gcaggttgtt gccgcagtgg aggggaaata  5700
atgattccgg ggatccgtcg acctgcagtt cgaagttcct atctagaaag tataggaact  5760
tcgaagcagc tccagcctac actgaaaact gttctgaaat aaatatctgt aataagaaat  5820
agccctcgcc gcttccctct acaggaatgg cgaagggctg tcggtttcga catggttggc  5880
catcgtatga tggcctttt tgtgcttatc gcgatgattt tcgctgcgct atcagggtaa  5940
atttatagtc atcggtatta aaagcgttgc ggctatattc aaacacccga ccatcaacta  6000
aatatccacg cgatacttt tcaagaatcg gctttgtctg gctgatatta agcagacggc  6060
tcatctcttc ggttggcatc agaggaatga tttcctgttc gctacgatcg ataaccattt  6120
tcttcacttc ttcgataaag tgatatttcg aattttccat gacctgccag gtgagatccg  6180
ggaacaacgc aagcggcatc caggtttctt ccagcgccat tggcttttgc ttgcgatagc  6240
gcacgcgctt cacatgccac acacgatcct gcggggtgat ttgtagctgt tgctgaagaa  6300
aatcgtcagc cggaatcact tcgaatatca gaacttcact gtgtgtatcg acgtgacggt  6360
ccgacagttt ttcatcaaaa ctggttaact gaaaaatatc gtaattgacc cgctcttctt  6420
tgacgtaagt cccgctgccc tgaatgcttt cgaggatctg ctgctcgact agctggcgca  6480
aagcctgacg caccgtaacc cggctgacgc caaactctgt ttgtagcgt tgctgaagaa  6540
gtaacgcatc gccaggttta agctcgccac gcgcaatttg ttcacgaatg cgatcggcaa  6600
tctgccggta taagggcttg tgtcccattt ttagtatctc attaatacga atttaaccat  6660
tatgcccgat aaattcatcc tgtaaataat acaaatacaa tacaaataat ttcaatcaag  6720
tgaaattgat cacataatgg tattgtttta tcg                                6753
```

```
SEQ ID NO: 3          moltype = DNA  length = 2742
FEATURE               Location/Qualifiers
source                1..2742
                      mol_type = genomic DNA
                      organism = Escherichia coli
SEQUENCE: 3
ccggtcaggc actgactgtg aatgagaaag gcgaagatgt ggttgttccg ggactgtttg   60
ccgttggtga aatcgcttgt gtatcggtac acggcgctaa ccgtctgggc ggcaactcgc  120
tgctggacct ggtggtcttt ggtcgcgcgg caggtctgca tctgcaagag tctatcgccg  180
agcagggcgc actgcgcgat gccagcgagt ctgatgttga agcgtctctg gatcgcctga  240
accgctggaa caataatcgt aacggtgaag atccggtggc gatccgtaaa gcgctgcaag  300
aatgtatgca gcataacttc tcggtcttcc gtgaaggtga tgcgatggcg aaagggcttg  360
agcagttgaa agtgatccgc gagcgtctga aaaatgcccg tctggatgac acttccagcg  420
agttcaacac ccagcgcgtt gagtgcctgg aactggataa cctgatggaa acggcgtatg  480
caacggctgt ttctgccaac ttccgtaccg aaagccgtgg cgcgcatagc cgcttcgact  540
tcccggatcg tgatgatgaa aactggctgt gccactccct gtatctgtca gagtcggaat  600
ccatgacgcg ccgaagcgtc aacatggaac cgaaactgcg cccggcattc cgccgaagaa  660
ttcgtactta ctaatgcgga gacaggaaaa tgagactcga gttttcaatt tatcgctata  720
acccggatgt tgatgatgct ccgcgtatgc aggattacac cctggaagcg gatgaaggtc  780
gcgacatgat gctgctggat gcgcttatcc agctaaaaga gaaagatccc agcctgtcgt  840
tccgccgctc ctgccgtgaa ggtgtgtgcg gttccgacgg tctgaacatg aacggcaaga  900
atggtctggc ctgtattacc ccgatttcgg cactcaacca gccgggcaag aagattgtga  960
ttcgcccgct gccaggttta ccggtgatcc gcgatttggt ggtagacatg ggacaattct  1020
atgcgcaata tgagaaaatt aagccttacc tgttgaataa tggacaaaat ccgccagctc  1080
gcgagcattt acagatgcca gagcagcgcg aaaaactcga cgggctgtat gaatgtattc  1140
tctgcggcag ttgttcaacc tcttgtccgt ctttctggtg gaatcccgat aagtttatcg  1200
gcccggcagg cttgttagcg gcatatcgtt tcctgattga tagccgtgat accgagactg  1260
acagccgcct cgacggtttg agtgatgcat tcagcgtatt ccgctgtcac agcatcatga  1320
actgcgtcag tgtatgtccg aaggggctga acccgacgcg cgccatcggc catatcaagt  1380
cgatgttgtt gcaacgtaat gcgtaaaccg taggcctgat aagacgcgca agcgtcgcat  1440
caggcaacca gtgccggatg cggcgtgaac gccttatccg gcctacaagt cattacccgt  1500
```

-continued

```
aggcctgata agcgcagcgc atcaggcgta acaaagaaat gcaggaaatc tttaaaaact    1560
gcccctgaca ctaagacagt tttaaaggt tccttcgcga gccactacgt agacaagagc     1620
tcgcaagtga accccggcac gcacatcact gtgcgtggta gtatccacgg cgaagtaagc    1680
ataaaaaga tgattccggg gatccgtcga cctgcagttc gaagttccta tctagaaagt    1740
ataggaactt cgaagcagct ccagcctaca ctgaaaactg ttctgaaata aatatctgta    1800
ataagaaata gccctcgccg cttccctcta caggaatggc gaagggctgt cggtttcgac    1860
atggttggcc atcgtatgat ggcctttttt gtgcttatcg cgatgatttt cgctgcgcta    1920
tcagggtaaa tttatagtca tcggtattaa aagcgttgcg gctatattca aacacccgac    1980
catcaactaa atatccacgc gatacttttt caagaatcgg ctttgtctgg ctgatattaa    2040
gcagacggct catctcttcg gttggcatca gaggaatgat ttcctgttcg ctacgatcga    2100
taaccatttt cttcacttct tcgataaagt gatatttcga attttccatg acctgccagg    2160
tgagatccgg gaacaacgca agcggcatcc aggtttcttc cagcgccatt ggcttttgct    2220
tgcgatagcg cacgcgcttc acatgccaca cacgatcctg cggggtgatt tgtagctgtt    2280
gctgaagaaa atcgtcagcc ggaatcactt cgaatatcag aacttcactg tgtgtatcga    2340
cgtgacggtc cgacagtttt tcatcaaaac tggttaactg aaaaatatcg taattgaccc    2400
gctcttcttt gacgtaagtc ccgctgccct gaatgctttc gaggatctgc tgctcgacta    2460
gctggcgcaa agcctgacgc accgtaaccc ggctgacgcc aaactctgtt tgtagcgctg    2520
attcagtggg taacgcatcg ccaggtttaa gctcgccacg cgcaatttgt tcacgaatgc    2580
gatcggcaat ctgccggtat aagggcttgt gtcccatttt tagtatctca ttaatacgaa    2640
tttaaccatt atgcccgata aattcatcct gtaaataata caaatacaat acaaataatt    2700
tcaatcaagt gaaattgatc acataatggt attgtttat cg                         2742
```

```
SEQ ID NO: 4          moltype = DNA   length = 6101
FEATURE               Location/Qualifiers
source                1..6101
                      mol_type = genomic DNA
                      organism = Escherichia coli
SEQUENCE: 4
ccacccatct gggtttgccg gtatttaata ccgtgcgtga ggcggttgcc gcaaccggtg    60
ccacggcttc agttatctat gttcctgccc cattttgtaa agattcaatt ctggaagcta    120
ttgatgcggg catcaaattg attattacga ttaccgaagg tatccctacg ctggatatgt    180
tgacggttaa agtgaaactt gatgaagcg gggtacgcat gattggtccg aattgtccgg     240
gcgttattac tccaggtgag tgcaaaattg gtattcagcc gggtcatatt cacaaacctg    300
ggaaagtcgg aattgtgtct cgttctggca ctctgacgta tgaggcagtt aaacagacca    360
cagattatgg ctttgggcag agtacctgtg tcggcatcgg agcgatcct attccggggga   420
gtaattttat cgatattctg gaaatgtttg agaaagatcc gcagaccgag gcaatcgtca    480
tgattggcga gattggcggt tccgcggaag aagaagctgc agcctatatc aaagaacatg    540
tcacaaaacc ggtagtgggc tatatcgcgg gagtcacggc cccaaaaggt aaacgtatgg    600
gccatgccga agcgatcatc gcgggcggca aaggcactgc agatgaaaaa tttgcagccc    660
ttgaggccgc tggcgtaaaa acggtccgtt cccttgctga tattggtgaa gcactgaaaa    720
ccgtgttgaa ataaaggtcc aggcatcaaa taaaacgaaa ggctcagtcg aaagactggg    780
cctttcgttt tatctgttgt ttgtcggtga acgctctcta ctagagtcac actggctcac    840
cttcggtggg gcctttctgc gtttatatgc catgtcttct actagtagcg gccgctgcag    900
tccggcaaaa aagggcaagg tgtcaccacc ctgcccttt tctttaaaac cgaaaagatt      960
acttcgcgtt atgcaggctt cctcgctcac tgactcgctg cgctcggtcg ttcggctgcg   1020
gcgagcggta tcagctcact caaaggcggt aatacggtta tccacagaat cagggggtaaa  1080
cgcaggaaag aacatgtgag caaaaggcca gcaaaaggcc aggaaccgta aaaaggccgc    1140
gttgctggcg tttttccaca ggctccgccc ccctgacgag catcacaaaa atcgacgctc    1200
aagtcagagg tggcgaaacc cgacaggact ataaagatac caggcgtttc ccctggaag     1260
ctccctcgtg cgctctcctg ttccgaccct gccgcttacc ggatacctgt ccgcctttct    1320
ccttcgggga agcgtggcgc tttctcatag ctcacgctgt aggtatctca gttcggtgta    1380
ggtcgttcgc tccaagctgg gctgtgtgca cgaaccccc gttcagcccg accgctgcgc     1440
cttatccggt aactatcgtc ttgagtccaa cccggtaaga cacgacttat cgccactggc    1500
agcagccact ggtaacagga ttagcagagc gaggtatgta ggcggtgcta cagagttctt    1560
gaagtggtgg cctaactacg gctacactag aagaacagta tttggtatct gcgctctgct    1620
gaagccagtt accttcggaa aaagagttgg tagctcttga tccggcaaac aaaccaccgc    1680
tggtagcggt ggtttttttg tttgcaagca gcagattacg cgcagaaaaa aaggatctca    1740
agaagatcct ttgatctttt ctacggggtc tgacgctcag tggaacgaaa actcacgtta    1800
agggattttg gtcatgagat tatcaaaaag gatcttcacc tagatccttt taaattaaaa    1860
atgaagtttt aaatcaatct aaagtatata tgagtaaact tggtctgaca gctcgagtcc    1920
cgtcaagtca gcgtaatgct ctgccagtgt tacaaccaat taaccaattc tgattagaaa    1980
aactcatcga gcatcaaatg aaactgcaat ttattcatat caggattatc aataccatat    2040
ttttgaaaaa gccgtttctg taatgaagga gaaaactcac cgaggcagtt ccataggatg    2100
gcaagatcct ggtatcggtc tgcgattccg actcgtccaa catcaataca acctattaat    2160
ttcccctcgt caaaaataag gttatcaagt gagaaatcaa catgagtgac gactgaatcc    2220
ggtgagaatg gcaaaagctt atgcatttct ttccagactt gttcaacagg ccagccatta    2280
cgctcgtcat caaaatcact cgcatcaacc aaaccgttat tcattcgtga ttgcgcctga    2340
gcgagacgaa atacgcgatc gctgttaaaa ggacaattac aaacaggaat cgaatgcaac    2400
cggcgcagga acactgccag cgcatcaaca atattttcac ctgaatcagg atattcttct    2460
aatacctgga atgctgtttt cccggggatc gcagtggtga gtaaccatgc atcatcagga    2520
gtacggataa aatgcttgat ggtcggaaga ggcataaatt ccgtcagcca gtttagtctg    2580
accatctcat ctgtaacatc attggcaacg ctacctttgc catgtttcag aaacaactct    2640
ggcgcatcgg gcttcccata caatcgatag attgtcgcac ctgattgccc gacattatcg    2700
cgagcccatt tatacccata taaatcagca tccatgttgg aatttaatcg cggcctggag    2760
caagacgttt cccgttgaat atggctcata cacccttg tattactgtt tatgtaagca     2820
gacagtttta ttgttcatga tgatatattt ttatcttgtg caatgtaaca tcagagattt    2880
tgagacacaa cgtggctttg ttgaataaat cgaactttg ctgagttgaa ggatcagctc     2940
gagtgccacc tgacgtctaa gaaaccatta ttatcatgac attaacctat aaaaataggc    3000
gtatcacgag gcagaatttc agataaaaaa aatccttagc tttcgctaag gatgatttct    3060
```

-continued

```
ggaattcgcg gccgcttcta gagactagtg gaagacatcg ctttgacagc tagctcagtc   3120
ctaggtactg tgctagctac tttaaactcc ccgagcaata gtaatgcaga actcagcatt   3180
gaaagcatgg cttgatagct cctatttatc aggtgctaac cagagctgga ttgaacagct   3240
gtatgaagat tttctgacag atccggattc agtggatgcg aattggcgca gcacttttca   3300
gcagttgcct ggcaccggtg taaaaccgga tcagtttcat tcccagacgc gggagtattt   3360
tcgtcgtctg gcgaaagatg cgagccggta ttcaagtaca atttctgatc cggatacgaa   3420
tgtaaaacag gtgaaagtgc ttcagttaat taatgcgtat cgctttagag gccatcagca   3480
tgcgaatctg gatccgctgg gcttatggca gcaggataaa gtcgcggatc tggatccaag   3540
ttttcacgat ttaacggaag ctgattttca ggaaaacttt aacgtcggct cattcgcaag   3600
tgggaaagaa acaatgaaac tgggcgaact tcttgaggcg ctgaaacaga cttattgtgg   3660
ccctattggt gcggaatata tgcatattac ctcaactgaa gagaaacgtt ggattcagca   3720
gagaatcgag agtggccgcg cgacttttaa ctccgaagaa aaaaaagat tcctgtcaga   3780
actgacagcc gcggaaggct tagagcggta tttgggtgcc aaattcccag gagcaaaacg   3840
gttcagcctg gagggcggtg atgcgctgat cccgatgctg aaagaaatga ttcggcatgc   3900
gggaaatagc ggaactcggg aagtggtgtt aggaatggca caccgcggcc gtttgaatgt   3960
actggttaac gtattaggaa aaaaacctca ggatttattt gatgagttcg cgggaaaaca   4020
taaagaacat ctgggcactg gtgatgtcaa atatcacatg ggcttctcaa gtgattttca   4080
gacggatgga ggtctggttc acctggcact ggcatttaat ccttctcatc tggaaatcgt   4140
aagtccggtc gttattggtt ccgtgcgcgc tcgcttagat cggttagatg aacctagctc   4200
aaacaaagtt ttaccaatca cgatccatgg ggatgcagct gttaccggac agggtgttgt   4260
gcaggagact ttgaatatgt ccaaagcgcg cgggtatgag gtgggtggta cggtgcgtat   4320
tgttatcaat aatcaggtgg gttttacaac cagtaaccct ctggatgctc gctctacgcc   4380
gtattgcact gatattggta aaatggtgca ggcaccaatt tttcacgtca atgccgatga   4440
tccggaagct gttgcctttg ttacgcgcct ggctctggat tttcgtaaca cttttcaaacg  4500
tgatgtattt atcgatttag tatgctatcg tcgtcatggt cataatgagg ctgatgaacc   4560
tagcgctacc cagccactga tgtatcagaa aattaaaaaa catcctaccc ctcgtaaaat   4620
ttatgcggat aaaactggagc aggaaaaagt ggctactctt gaagatgcta ctgaaatggt   4680
caatctttat cgggatgcat tggatgcggg tgattgcgtg gtcgcggaat ggcgcgccgat  4740
gaatatgcat tcatttactt ggtcaccgta tttaaatcat gagtgggatg aggaatatcc   4800
gaataaagtg gagatgaaac gcctgcagga attagcaaaa cgtattagca cagtacctga   4860
agcggttgag atgcagtcta gagttgccaa aatctatgga gatcgccagg ccatggcagc   4920
aggggaaaaa cttttttgatt ggggggggagc cgaaaacctg gcatatgcga cgctggtaga   4980
tgagggcatt ccggtgcgcc tttctggtga agattctggg cgcggtactt tttttcatcg   5040
gcacgctgtt attcataacc agtctaacgg tagtactat actccgctgc agcacatcca   5100
caatggtcag ggtgcgttcc gtgtatggga ttccgtgctg agtgagaag cggttcttgc   5160
gtttgagtat gggtatgcaa ctgccgagcc acgcacgctg acgatctggg aagcccagtt   5220
tggcgatttt gcaaatggtg cccaggtggt aatcgatcag tttattagct ccggcgaaca   5280
gaaatggggg cggatgtgtg gtttagttat gttgttaccg catggctatg aaggtcaggg   5340
acctgagcac agctcagcgc gcctggaacg ctatcttcag ctgtgtgcgg aacagaacat   5400
gcaggtatgc gttccttcca cgccggctca ggtttatcat atgttaagac gtcaggcctt   5460
gcgcggtatg cggcgcccgt tggtcgtgat gtccccgaaa agtttactgc gccatccgtt   5520
agcagttagc agcctggagg aactggcaaa cggtacgttc ttgccagcta tcggcgaaat   5580
cgatgaactg gatcctaaag gggtgaaacg cgttgttatg tgttctggta aagtgtatta   5640
tgatcttttg gaacagcgtc gcaaaaataa tcagcacgat gtagctattg tgcggatcga   5700
gcagctgtat ccgttcccgc acaaagcaat gcaggaagtg ctgcagcagt tcgcacatgt   5760
caaagatttt gtctggtgtc aggaggaacc gcttaatcag ggggcctggt attgtagtca   5820
gcaccatttc cgggaggtga tcccgtttgg ggcgtcctta cggtatgctg gtcgccctgc   5880
ctccgcaagt ccggccgtgg gatatatgag cgttcaccag aaacagcagc aggatttggt   5940
gaatgatgct ttgaatgtgg aatgaatgtc catcctgatc gacaaaaaca ctaaagtaat   6000
ttgtcagggc tttaccggtt cccagggcac atttcactca gagcaggcca tcgcttatgg   6060
gaccaaaatg gtgggtggtg taacgcctgg taaaggaggc a                        6101
```

```
SEQ ID NO: 5                moltype = DNA   length = 9013
FEATURE                     Location/Qualifiers
source                      1..9013
                            mol_type = genomic DNA
                            organism = Escherichia coli
SEQUENCE: 5
ccggcgaaag agtctgctcc ggcagcggct gctccggcgg cgcaaccggc tctggctgca   60
cgtagtgaaa aacgtgtccc gatgactcgc ctgcgtaagc gtgtggcaga gcgtctgctg   120
gaagcgaaaa actccaccgc catgctgacc acgttcaacg aagtcaacat gaagccgatt   180
atggatctgc gtaagcagta cggtgaagcg tttgaaaaac gccacggcat ccgtctgggc   240
tttatgtcct tctacgtgaa agcggtggtt gaagccctga acgttaccc ggaagtgaac   300
gcttctatcg acggcgatga cgtggtttac cacaactatt cgtagtcag catggcggtt   360
tctacgccgc gcggcctggt gacgccggtt ctgcgtgatg tcgataccct cggcatggca   420
gacatcgaga agaaaatcaa agagctggca gtcaaaggcc gtgacggcaa gctgaccgtt   480
gaagatctga ccggtggtaa cttcaccatc accaacggtg gtgtgttcgg ttccctgatg   540
tctacgccga tcatcaaccc gccgcagagc gcaattctgg gtatgcacgc tatcaaagat   600
cgtccgatgg cggtgaatgg tcaggttgag atcctgccga tgatgtacct ggcgctgtcc   660
tacgatcacc gtctgatcga tggtcgcgaa tccgtgggct tcctggtaac gatcaaaagc   720
ttgctgaag atccgacgcg tctgctgctg gacgtgagt agtttaagtt tcacctgcac   780
tgtagaccga ataaggcatt atcgccttct ccggcaattg aagcctgatg cgacgctgac   840
gcgtcttatc aggcctacgg gaccaccaat gtaggtcgga taaggcgcaa cgcgccgatc   900
cgacaagcga tgcctgatgt gacgtttaac gtgtcttatc aggcctacgg gtgaccgaca   960
atgcccggaa gcgatacgaa atattcggtc tacggtttaa aagataacga ttactgaagg   1020
atggacagaa cacatgaact tacatgaata tcagcaaaa caacttttg cccgctatgg   1080
cttaccagca ccggtgggtt atgcctgtac tactccgcgc gaagcagaag aagccgcttc   1140
aaaaatcggt gccggtccgt gggtagtgaa atgtcaggtt cacgctggtg gccgcggtaa   1200
agcgggcggt gtgaaagttg taaacagcaa agaggacatc cgtgcttttg cagaaaactg   1260
```

-continued

```
gctgggcaag cgtctggtaa cgtatcaaac agatgccaat ggccaaccgg ttaaccagat    1320
tctggttgaa gcagcgaccg atatcgctaa agagctgtat ctcggtgccg ttgttgaccg    1380
tagttcccgt cgtgtggtct ttatggcctc caccgaaggc ggcgtggaaa tcgaaaaagt    1440
ggcggaagaa actccgcacc tgatccataa agttgcgctt gatccgctga ctggcccgat    1500
gccgtatcag ggacgcgagc tggcgttcaa actgggtctg gaaggtaaac tggttcagca    1560
gttcaccaaa atcttcatgg gcctggcgac cattttcctg gagcgcgacc tggccgttgat    1620
cgaaatcaac ccgctggtca tcaccaaaca gggcgatctg atttgcctcg acggcaaact    1680
gggcgctgac ggcaacgcac tgttccgcca gcctgatctg cgcgaaatgc gtgaccagtc    1740
gcaggaagat ccgcgtgaag cacaggctgc acagtgggaa ctgaactacg ttgcgctgga    1800
cggtaacatc ggttgtatgg ttaacggcgc aggtctggcg atgggtacga tggacatcgt    1860
taaactgcac ggcggcgaac cggctaactt ccttgacgtt ggcggcggcg caaccaaaga    1920
acgtgtaacc gaagcgttca aaatcatcct ctctgacgac aaagtgaaag ccgttctggt    1980
taacatcttc ggcggtatcg ttcgttgcga cctgatcgct gacggtatca tcggcgcggt    2040
agcagaagtg ggtgttaacg taccggtcgt ggtacgtccg gaaggtaaca acgccgaact    2100
cggcgcgaag aaactggctg acagcggcct gaatattatt gcagcaaaag gtctgacgga    2160
tgcagctcag caggttgttg ccgcagtgga ggggaaataa tgtccatttt aatcgataaa    2220
aacaccaagg ttatctgcca gggctttacc ggtagccagg ggactttcca ctcagaacag    2280
gccattgcat acggcactaa aatggttggc ggcgtaaccc caggtaaagg cggcaccacc    2340
cacctcggcc tgccggtgtt caacaccgtg cgtgaagccg ttgctgccac tggcgctacc    2400
gcttctgtta tctacgtacc agcaccgttc tgcaaagact ccattctgga agccatcgac    2460
gcaggcatca aactgattat caccatcact gaaggcatcc cgacgctgga tatgctgacc    2520
gtgaaagtga agctggatga agcaggcgtt cgtatgatcg gcccgaactg cccaggcgtt    2580
atcactccgg gtgaatgcaa aatcggtatc cagcctggtc acattcacaa accgggtaaa    2640
gtgggtatcg tttcccgttc cggtacactg acctatgaag cggttaaaca gaccacggat    2700
tacggtttcg gtcagtcgac ctgtgtcggt atcggcggtg acccgatccc gggctctaac    2760
tttatcgaca ttctcgaaat gttcgaaaaa gatccgcaga ccgaagcgat cgttgatgatc    2820
ggtgagatcg gcggtagcgc tgaagaagaa gcagctgcgt acatcaaaga gcacgttacc    2880
aagccagttg tgggttacat cgctggtgtg actcgcgcga aaggcaaacg tatgggccac    2940
gcgggtgcca tcattgccgg tgggaaaggg actgcggatg agaaattcgc tgctctggaa    3000
gccgcaggcg tgaaaaccgt tcgcagcctg ggcgatatcg gtgaagcact gaaaactgtt    3060
ctgaaataaa ggtccaggca tcaaataaaa cgaaaggctc agtcgaaaga ctgggccttt    3120
cgttttatct gttgtttgtc ggtgaacgct ctctactaga gtcacactgg ctcaccttcg    3180
ggtgggcctt tctgcgttta tatgccatgt cttctactag tagcggccgc tgcagtccgg    3240
caaaaaaggg caaggtgtca ccaccctgcc ctttttcttt aaaaccgaaa agattacttc    3300
gcgttatgca ggcttcctcg ctcactgact cgctgcgctc ggtcgttcgg ctgcggcgag    3360
cggtatcagc tcactcaaag gcggtaatac ggttatccac agaatcaggg gataacgcag    3420
gaaagaacat gtgagcaaaa ggccagcaaa aggccaggaa ccgtaaaaag gccgcgttgc    3480
tggcgttttt ccacaggctc cgcccccctg acgagcatca caaaaatcga cgctcaagtc    3540
agaggtggcg aaacccgaca ggactataaa gataccaggc gtttccccct ggaagctccc    3600
tcgtgcgctc tcctgttccg acctgccgc ttaccggata cctgtccgcc tttctcccctt    3660
cgggaagcgt ggcgctttct catagctcac gctgtaggta tctcagttcg gtgtaggtcg    3720
ttcgctccaa gctgggctgt gtgcacgaac cccccgttca gcccgaccgc tgcgccttat    3780
ccggtaacta tcgtcttgag tccaacccgg taagacacga cttatcgcca ctggcagcag    3840
ccactggtaa caggattagc agagcgaggt atgtaggcgg tgctacagag ttcttgaagt    3900
ggtggcctaa ctacggctac actagaagaa cagtatttgg tatctgcgct ctgctgaagc    3960
cagttacctt cggaaaaaga gttggtagct cttgatccgg caaacaaacc accgctggta    4020
gcggtggttt ttttgtttgc aagcagcaga ttacgcgcag aaaaaaagga tctcaagaag    4080
atcctttgat cttttctacg gggtctgacg ctcagtggaa cgaaaactca cgttaaggga    4140
ttttggtcat gagattatca aaaaggatct tcacctagat cctttttaaat taaaaatgaa    4200
gttttaaatc aatctaaagt atatatgagt aaacttggtc tgacagctcg agtcccgtca    4260
agtcagcgta atgctctgcc agtgttacaa ccaattaacc aattctgatt agaaaaactc    4320
atcgagcatc aaatgaaact gcaatttatt catatcagga ttatcaatac catattttttg    4380
aaaaagccgt ttctgtaatg aaggagaaaa ctcaccgagg cagttccata ggatggcaag    4440
atcctggtat cggtctgcga ttccgactcg tccaacatca atacaaccta ttaatttccc    4500
ctcgtcaaaa ataaggttat caagtgagaa atcaccatga gtgacgactg aatccggtga    4560
gaatggcaaa agcttatgca tttctttcca gacttgttca acaggccagc cattacgctc    4620
gtcatcaaaa tcactcgcat caaccaaacc gttattcatt cgtgattgcg cctgagcgag    4680
acgaaatacg cgatcgctgt taaaaggaca attacaaaca ggaatcgaat gcaaccggcg    4740
caggaacact gccagcgcat caacaatatt ttcacctgaa tcaggatatt cttctaatac    4800
ctggaatgct gtttttcccg ggatcgcagt ggtgagtaac catgcatcat caggagtacg    4860
gataaaatgc ttgatggtcg gaagaggcat aaattccgtc agccagttta gtctgaccat    4920
ctcatctgta acatcattgg caacgctacc tttgccatgt ttcagaaaca actctggcgc    4980
atcgggcttc ccatacaatc gatagattgt cgcacctgat tgcccgacat tatcgcgagc    5040
ccatttatac ccatataaat cagcatccat gttggaattt aatcgcggcc tggagcaaga    5100
cgtttcccgt tgaatatggc tcataacacc ccttgtatta ctgtttatgt aagcagacag    5160
ttttattgtt catgatgata tttttttatc ttgtgcaatg taacatcaga gattttgaga    5220
cacaacgtgg ctttgttgaa taaatcgaac ttttgctgag ttgaaggatc agctcgagtg    5280
ccacctgacg tctaagaaac cattattatc atgacattaa cctataaaaa taggcgtatc    5340
acgaggcaga atttcagata aaaaaaatcc ttagctttcg ctaaggatga tttctggaat    5400
tcgcggccgc ttctagagac tagtggaaga catcgctacc gtaggcctga taagacgcgc    5460
aagcgtcgca tcaggcaacc agtgccggat cggcgtgaa cgccttatcc ggcctacaag    5520
tcattacccg taggcctgat aagcgcagcg catcaggcgt aacaaagaaa tgcaggaaat    5580
ctttaaaaac tgcccctgac actaagacag ttttttaaagg ttccttcgcg agccactacg    5640
tagacaagag ctcgcaagtg aaccccggca cgcacataac tgtgcgtggt agtatccacg    5700
gcgaagtaag cataaaaaag atgcttaagg gatcacgaat gcagaacagc gctttgaaag    5760
cctggttgga ctcttcttac ctctctggcg caaaccagag ctggatagaa cagctctatg    5820
aagatttctt aaccgatcct gactcggttg acgctaactg gcgttcgacg ttccagcagt    5880
tacctggtac gggagtcaaa ccggatcaat tccactctca aacgcgtgaa tatttccgcc    5940
gcctggcgaa agacgcttca cgttactctt caacgatctc cgaccctgac accaatgtga    6000
```

```
agcaggttaa agtcctgcag ctcattaacg cataccgctt ccgtggtcac cagcatgcga  6060
atctcgatcc gctgggactg tggcagcaag ataaagtggc cgatctggat ccgtctttcc  6120
acgatctgac cgaagcagac ttccaggaga ctttcaacgt cggttcattt gccagcggca  6180
aagaaaccat gaaactcggc gagctgctgg aagccctcaa gcaaacctac tgcggcccga  6240
ttggtgccga gtatatgcac attaccagca ccgaagaaaa acgctggatc caacagcgta  6300
tcgagtctgg tcgcgcgact ttcaatagcg aagagaaaaa acgcttctta agcgaactga  6360
ccgccgctga aggtcttgaa cgttacctcg gcgcaaaatt ccctggcgca aaacgcttct  6420
cgctggaagg cggtgacgcg ttaatcccga tgcttaaaga gatgatccgc cacgctggca  6480
acagcggcac ccgcgaagtg gttctcggga tggcgcaccg tggtcgtctg aacgtgctga  6540
tgaacgtgct gggtaaaaaa ccgcaagact tgttcgacga gttcgccggt aaacataaag  6600
aacacctcgg cacgggtgac gtgaaatacc acatgggctt ctcgtctgac ttccagaccg  6660
atggcggcct ggtgcacctg gcgctggcgt ttaacccgtc tcaccttgag attgtaagcc  6720
cggtagttat cggttctgtt cgtgcccgtc tggacagact tgatgagccg agcagcaaca  6780
aagtgctgcc aatcaccatc cacggtgacg ccgcagtgac cgggcagggc gtggttcagg  6840
aaaccctgaa catgtcgaaa gcgcgtggtt atgaagttgg cggtacggta cgtatcgtta  6900
tcaacaacca ggttggtttc accacctcta atccgctgga tgcccgttct acgccgtact  6960
gtactgatat cggtaagatg gttcaggccc cgatttccca cgttaacgcg gacgatccgg  7020
aagccgttgc ctttgtgacc cgtctggccg tcgatttccg taacaccttt aaacgtgatg  7080
ttttcatcga cctggtgtgc taccgccgtc acggccacaa cgaagccgac gagccgagcg  7140
caacccagcc gctgatgtat cagaaaatca aaaaacatcc gacaccgcgc aaaatctacg  7200
ctgacaagct ggagcaggaa aaagtggcga cgctggaaga tgccaccgag atggttaacc  7260
tgtaccgcga tgcgctggat gctggcgatt gcgtagtggc agagtggcgt ccgatgaaca  7320
tgcactcttt cacctggtcg ccgtacctca accacgaatg ggacgaagag tacccgaaca  7380
aagttgagat gaagcgcctg caggagctgg cgaaacgcat cagcacggtg ccggaagcag  7440
ttgaaatgca gtctcgcgtt gccaagattt atggcgatcg ccaggcgatg gctgccggtg  7500
agaaactgtt cgactggggc ggtgcggaaa acctcgctta cgccacgctg gttgatgaag  7560
gcattccggt tcgcctgtcg ggtgaggact ccggtcgcgg taccttcttc caccgccacg  7620
cggtgatcca caaccagtct aacggttcca cttacacgcc gctgcaacat atccataacg  7680
ggcagggcgc gttccgtgtc tgggactccg tactgtctga agaagcagtg ctggcgtttg  7740
aatatggtta tgccaccgca gaaccacgca ctctgaccat ctgggaagcg cagttcggtg  7800
acttcgccaa cggtgcgcag gtggttatcg accagttcat ctcctctggc gaacagaaat  7860
ggggccggat gtgtggtctg gtgatgttgc tgccgcacgg ttacgaaggg caggggccgg  7920
agcactcctc cgcgcgtctg gaacgttatc tgcaactttg tgctgagcaa aacatgcagg  7980
tttgcgtacc gtctaccccg gcacaggttt accacatgct gcgtcgtcag gcgctgcgcg  8040
ggatgcgtcg tccgctggtc gtgatgtcgc cgaaatccct gctgcgtcat ccgctggcgg  8100
tttccagcct cgaagaactg gcgaacggca ccttcctgcc agccatcggt gaaatcgacg  8160
agcttgatcc gaagggcgtg aagcgcgtag tgatgtgttc tggtaaggtt tattacgacc  8220
tgctggaaca gcgtcgtaag aacaatcaac acgatgtcgc cattgtgcgt atcgagcaac  8280
tctacccgtt cccgcataaa gcgatgcagg aagtgttgca gcagtttgct cacgtcaagg  8340
attttgtctg gtgccaggaa gagccgctca accaggggcgc atggtactgc agccagcatc  8400
atttccgtga agtgattccg tttgggggct ctctgcgtta tgcaggccgc ccggcctccg  8460
cctctccggc ggtagggtat atgtccgttc accagaaaca gcaacaagat ctggttaatg  8520
acgcgctgaa cgtcgaataa ataaaggata cacaatgagt gccgtagata ttctggtcct  8580
tgacctgcct gaatccgtag ccgatgccac cgtcgcaacc tggcataaaa aaccggcga  8640
cgcagtcgta cgtgatgaag tgctggtaga aatcgaaact gacaaagtgg tactggaagt  8700
accggcatca gcagacggca ttctggatgc ggttctggaa gatgaaggta caacggtaac  8760
gtctcgtcag atccttggtc gcctgcgtga aggcaacagc gaaggtaaag aaaccagcgc  8820
caaatctgaa gagaaagcgt ccactccggc gcaacgccag caggcgtctc tggaagagca  8880
aaacaacgat gcgttaagcc cggcgatccg tcgcctgctg gctgaacaca atctcgacgc  8940
cagcgccatt aaaggcaccg gtgtgggtgg tcgtctgact cgtgaagatg tggaaaaaca  9000
tctggcgaaa gcc                                                       9013
```

```
SEQ ID NO: 6              moltype = DNA  length = 6608
FEATURE                  Location/Qualifiers
source                   1..6608
                         mol_type = genomic DNA
                         organism = Escherichia coli
SEQUENCE: 6
cgcgttgctg gcgttttttcc acaggctccg ccccctgac gagcatcaca aaaatcgacg  60
ctcaagtcag aggtggcgaa acccgacagg actataaaga taccaggcgt ttccccctgg  120
aagctccctc gtgcgctctc ctgttccgac cctgccgctt accggatacc tgtccgcctt  180
tctcccttcg ggaagcgtgg cgctttctca tagctcacgc tgtaggtatc tcagttcggt  240
gtaggtcgtt cgctccaagc tgggctgtgt gcacgaaccc cccgttcagc ccgaccgctg  300
cgccttatcc ggtaactatc gtcttgagtc caacccggta agacacgact tatcgccact  360
ggcagcagcc actggtaaca ggattagcag agcgaggtat gtaggcggtg ctacagagtt  420
cttgaagtgg tggcctaact acggctacac tagaagaaca gtatttggta tctgcgctct  480
gctgaagcca gttaccttcg gaaaaagagt tggtagctct tgatccggca aacaaaccac  540
cgctggtagc ggtggttttt ttgtttgcaa gcagcagatt acgcgcagaa aaaaaggatc  600
tcaagaagat cctttgatct tttctacggg gtctgacgct cagtggaacg aaaactcacg  660
ttaagggatt ttggtcatga gattatcaaa aaggatcttc acctagatcc ttttaaatta  720
aaaatgaagt tttaaatcaa tctaaagtat atatgagtaa acttggtctg acagctcgag  780
tttacggcta gctcagtcct aggtatagtg ctagctactt gttagaaaag agaagcacgt  840
aatgcagaac tcagcattga aagcatggct tgatagctcc tatttatcag gtgctaacca  900
gagctggatt gaacagctgt atgaagattt tctgacagat ccggattcag tggatgccaa  960
ttggcgcagc acttttcagc agttgcctgg caccggtgta aaaccggatc agtttcattc  1020
ccagacgcgg gagtatttttc gtcgtctggc gaaagatgcg agccggtatt caagtacaat  1080
ttctgatccg gatacgaatg taaaacaggt gaaagtgctt cagttaatta atgcgtatcg  1140
ctttagaggc catcagcatg cgaatctgga tccgctgggc ttatggcagc aggataaagt  1200
cgcggatctg gatccaagtt ttcacgattt aacggaagct gattttcagg aaacctttaa  1260
```

-continued

```
cgtcggctca ttcgcaagtg ggaaagaaac aatgaaactg ggcgaacttc ttgaggcgct   1320
gaaacagact tattgtggcc ctattggtgc ggaatatatg catattacct caactgaaga   1380
gaaacgttgg attcagcaga gaatcgagag tggccgcgcg acttttaact ccgaagaaaa   1440
aaaaagattc ctgtcagaac tgacagccgc ggaaggctta gagcggtatt tgggtgccaa   1500
attcccagga gcaaaacggt tcagcctgga gggcggtgat gcgctgatcc cgatgctgaa   1560
agaaatgatt cggcatgcgg gaaatagcgg aactcgggaa gtggtgttag gaatggcaca   1620
ccgcggccgt ttgaatgtac tggttaacgt attaggaaaa aaacctcagg atttatttga   1680
tgagttcgcg ggaaaacata aagaacatct gggcactggt gatgtcaaat atcacatggg   1740
cttctcaagt gattttcaga cggatggagg tctggttcac ctggcactgg catttaatcc   1800
ttctcatctg gaaatcgtaa gtccggtcgt tattggttcc gtgcgcgctc gcttagatcg   1860
gttagatgaa cctagctcaa acaaagtttt accaatcacg atccatgggg atgcagctgt   1920
taccggacag ggtgttgtgc aggagacttt gaatatgtcc aaagcgcgcg ggtatgaggt   1980
gggtggtacg gtgcgtattg ttatcaataa tcaggtgggg tttacaacca gtaacccttc   2040
ggatgctcgc tctacgccgt attgcactga tattggtaaa atggtgcagg caccaatttt   2100
tcacgtcaat gccgatgatc cggaagctgt tgcctttgtt acgcgcctgg ctctggattt   2160
tcgtaacact ttcaaacgtg atgtatttat cgatttagta tgctatcgtc gtcatggtca   2220
taatgaggct gatgaaccta gcgctaccca gccactgatg tatcagaaaa ttaaaaaaca   2280
tcctacccct cgtaaaattt atgcggataa actggagcag gaaaaagtgg ctactcttga   2340
agatgctact gaaatggtca atctttatcg ggatgcattg gatgcgggtg attgcgtggt   2400
cgcggaatgg cgcccgatga atatgcattc atttacttgg tcaccgtatt taaatcatga   2460
gtgggatgag gaatatccga ataaagtgga gatgaaacgc ctgcaggaat tagcaaaacg   2520
tattagcaca gtacctgaag cggttgagat gcagtctgaa gttgccaaaa tctatggaga   2580
tcgccaggcc atggcagcag gggaaaaaact tttttgattgg gggggagccg aaaacctggc   2640
atatgcgacg ctggtagatg agggcattcc ggtgcgcctt tctggtgaag attctgggcg   2700
cggtactttt tttcatcggc acgctgttat tcataaccag tctaacggta gtacttatac   2760
tccgctgcag cacatccaca atggtcaggg tgcgttccgt gtatgggatt ccgtgctgag   2820
tgaagaagcg gttcttcgt ttgagtatgg gtatgcaact gccgagccac gcacgctgac   2880
gatctgggaa gcccagtttg gcgattttgc aaatggtgcc caggtggtaa tcgatcagtt   2940
tattagctcc ggcgaacaga aatgggggcg gatgtgtggt ttagttatgt tgttaccgca   3000
tggctatgaa ggtcagggac ctgagcacag ctcagcgcgc ctggaacgct atcttcagct   3060
gtgtgcggaa cagaacatgc aggtatgcgt tccttccacg ccggctcagg tttatcatat   3120
gttaagacgt caggccttgc gcggtatgcg gcgcccgttg gtcgtgatgt ccccgaaaag   3180
tttactgcgc catccgttag cagttagcag cctggaggaa ctggcaaacg gtacgttctt   3240
gccagctatc ggcgaaatcg atgaactgga tcctaaaggg gtgaaacgcg ttgttatgtg   3300
ttctggtaaa gtgtattatg atcttttgga acagcgtgac aaaaataatc agcacgatgt   3360
agctattgtg cggatcgagc agctgtatcc gttcccgcac aaagcaatgc aggaagtgct   3420
gcagcagttc gcacatgtca aagattttgt ctggtgtcag gaggaaccgc ttaatcaggg   3480
ggcctggtat tgtagtcagc accatttccg ggaggtgatc ccgtttgggg cgtccttacg   3540
gtatgctggt cgccctgcct ccgcaagtcc ggccgtggga tatatgagcg ttcaccagaa   3600
acagcagcag gatttggtga atgatgcttt gaatgtggaa tgaatgtcca tcctgatcga   3660
caaaaacact aaagtaattt gtcagggctt taccggttcc cagggcacat ttcactcaga   3720
gcaggccatc gcttatggga ccaaaatggt gggtggtgta acgcctggta aaggaggcac   3780
cacccatctg ggtttgccgg tatttaatac cgtgcgtgag gcggttgccg caaccggtaa   3840
cacggcttca gttatctatg ttcctgcccc attttgtaaa gattcaattc tggaagctat   3900
tgatgcgggc atcaaattga ttattacgat taccgaaggt atccctacgc tggatatgtt   3960
gacggttaaa gtgaaacttg atgaagcggg ggtacgcatg attggtccga attgtccggg   4020
cgttattact ccaggtgagt gcaaaattgg tattcagccg ggtcatattc acaaacctgg   4080
gaaagtcgga attgtgtctc gttctggcac tctgacgtat gaggcagtta aacagaccac   4140
agattatggc tttgggcaga gtacctgtgt cggcatcgga ggcgatccta ttccggggag   4200
taattttatc gatattctgg aaatgtttga gaaagatccg cagaccgagg caatcgtcat   4260
gattggcgag attggcggtt ccgcggaaga agaagctgca gcctatatca aagaacatgt   4320
cacaaaaccg gtagtgggct atatcgcggg agtcacggcc ccaaaaggta aacgtatggg   4380
ccatgccgga gcgatcatcg cgggcggcaa aggcactgca gatgaaaaat ttgcagccct   4440
tgaggccgct ggcgtaaaaa cggtccgttc ccttgctgat attggtgaag cactgaaaac   4500
cgtgttgaaa taaaggtcca ggcatcaaat aaaacgaaag gctcagtcga aagactgggc   4560
ctttcgtttt atctgttgtt tgtcggtgaa cgctctctac tagagtcaca ctggctcacc   4620
ttcgggtggg cctttctgcg tttatactcg agtgccacct gacgtctaag aaaccattat   4680
tatcatgaca ttaacctata aaaataggcg tatcacgagg cagaatttca gataaaaaaa   4740
atccttagct ttcgctaagg atgatttctg gaattcgcgg ccgcttctag aactagtagg   4800
aagacatcgc tagagacctg caccatatgc ggtgtgaaat accgcacaga tgcgtaagga   4860
gaaaataccg catcaggcgc cattcgccat tcaggctgcg caactgttgg gaagggcgat   4920
cggtgcgggc ctcttcgcta ttacgccagc tggcgaaagg gggatgtgct gcaaggcgat   4980
taagttgggt aacgccaggg ttttcccagt cacgacgttg taaaacgacg gccagtgaat   5040
tcgagctcgg tacccgggga tcctctagag tcgacctgca ggcatgcaag cttggctcac   5100
tcatggtcat agctgtttcc tgtgtgaaat tgttatccgc tcacaattcc acacaacata   5160
cgagccggaa gcataaagtg taaagcctgg ggtgcctaat gagtgagcta actcacatta   5220
attgcgttgc gctcactgcc cgctttccag tcgggaaacc tgtcgtgcca gctgcattaa   5280
tgaatcggcc aacgcgcggg ggtttataaa atcccgtcaa gtcagcgtaa tgctctgcca   5340
gtgttacaac caattaacca attctgatta gaaaaactca tcgagcatca aatgaaactg   5400
caatttattc atatcaggat tatcaatacc atatttttga aaaagccgtt tctgtaatga   5460
aggagaaaac tcaccgaggc agttccatag gatggcaaga tcctggtatc ggtctgcgat   5520
tccgactcgt ccaacatcaa tacaacctat taatttcccc tcgtcaaaaa taaggttatc   5580
aagtgagaaa tcaccatgag tgacgactga atccggtgag aatggcaaaa gcttatgcat   5640
ttctttccag acttgttcaa caggccagcc attacgctcg tcatcaaaat cactcgcatc   5700
aaccaaaccg ttattcattc gtgattgcgc ctgagcgaga cgaaatacgc gatcgctgtt   5760
aaaaggacaa ttacaaacag gaatcgaatg caaccggcgc aggaacactg ccagcgcatc   5820
aacaatattt tcacctgaat caggatattc ttctaatacc tggaatgctg ttttcccggg   5880
gatcgcagtg gtgagtaacc atgcatcatc aggagtacgg ataaaatgct tgatggtcgg   5940
aagaggcata aattccgtca gccagtttag tctgaccatc tcatctgtaa catcattggc   6000
```

-continued

```
aacgctacct ttgccatgtt tcagaaacaa ctctggcgca tcgggcttcc catacaatcg    6060
atagattgtc gcacctgatt gcccgacatt atcgcgagcc catttatacc catataaatc    6120
agcatccatg ttggaattta atcgcggcct ggagcaagac gtttcccgtt gaatatggct    6180
cataacaccc cttgtattac tgtttatgta agcagacagt tttattgttc atgatgatat    6240
attttatct tgtgcaatgt aacatcagag attttgagac acaacgtggc tttgttgaat    6300
aaatcgaact tttgctgagt tgaaggatca gggtctcttg ccatgtcttc tactagtagc    6360
ggccgctgca gtccggcaaa aaagggcaag gtgtcaccac cctgccctt ttctttaaaa    6420
ccgaaaagat tacttcgcgt tatgcaggct tcctcgctca ctgactcgct gcgctcggtc    6480
gttcggctgc ggcgagcggt atcagctcac tcaaaggcgg taatacggtt atccacagaa    6540
tcaggggata acgcaggaaa gaacatgtga gcaaaaggcc agcaaaaggc caggaaccgt    6600
aaaaaggc                                                              6608

SEQ ID NO: 7            moltype = DNA  length = 9517
FEATURE                 Location/Qualifiers
source                  1..9517
                        mol_type = genomic DNA
                        organism = Escherichia coli
SEQUENCE: 7
cgcgttgctg gcgtttttcc acaggctccg cccccctgac gagcatcaca aaaatcgacg     60
ctcaagtcag aggtggcgaa acccgacagg actataaaga taccaggcgt ttccccctgg    120
aagctccctc gtgcgctctc ctgttccgac cctgccgctt accggatacc tgtccgcctt    180
tctccccttcg ggaagcgtgg cgctttctca tagctcacgc tgtaggtatc tcagttcggt    240
gtaggtcgtt cgctccaagc tgggctgtgt gcacgaaccc cccgttcagc ccgaccgctg    300
cgccttatcc ggtaactatc gtcttgagtc caacccggta agacacgact tatcgccact    360
ggcagcagc actggtaaca ggattagcag agcgaggtat gtaggcggtg ctacagagtt    420
cttgaagtgg tggcctaact acggctacac tagaagaaca gtatttggta tctgcgctct    480
gctgaagcca gttaccttcg gaaaaagagt tggtagctct tgatccggca aacaaaccac    540
cgctggtagc ggtggttttt ttgtttgcaa gcagcagatt acgcgcagaa aaaaaggatc    600
tcaagaagat cctttgatct tttctacggg gtctgacgct cagtggaacg aaaactcacg    660
ttaagggatt ttggtcatga gattatcaaa aaggatcttc acctagatcc ttttaaatta    720
aaaatgaagt tttaaatcaa tctaaagtat atatgagtaa acttggtctg acagctcgag    780
gtaggcctga taagacgcgc aagcgtcgca tcaggcaacc agtgccggat gcggcgtgaa    840
cgccttatcc ggcctacaag tcattacccg taggcctgat aagcgcagcg catcaggcgt    900
aacaaagaaa tgcaggaaat ctttaaaaac tgcccctgac actaagacag tttttaaagg    960
ttccttcgcg agccactacg tagacaagag ctcgcaagtg aaccccggca cgcacatcac    1020
tgtgcgtggt agtatccacg gcgaagtaag cataaaaaag atgcttaagg gatcacgaat    1080
gcagaacagc gctttgaaag cctggttgga ctcttcttac ctctctggcg caaaccagag    1140
ctggatagaa cagctctatg aagatttctt aaccgatcct gactcggttg acgctaactg    1200
gcgttcgacg ttccagcagt tacctggtac gggagtcaaa ccggatcaat tccactctca    1260
aacgcgtgaa tatttccgcc gcctggcgaa agacgcttca cgttactctt caacgatctc    1320
cgaccctgac accaatgtga agcaggttaa agtcctgcag ctcattaacg cataccgctt    1380
ccgtggtcac cagcatgcga atctcgatcc gctgggact tggcagcaag ataaagtggc    1440
cgatctggat ccgtctttcc acgatctgac cgaagcagac ttccaggaga ctttcaacgt    1500
cggttcattt gccagcggca agaaaccat gaaactcggc gagctgctgg aagccctcaa    1560
gcaaacctac tgcggcccga ttggtgccga gtatatgcac attaccagca ccgaagaaaa    1620
acgctggatc caacagcgta tcgagtctgg tcgcgcgact ttcaatagcg aagagaaaaa    1680
acgcttctta agcgaactga ccgccgctga aggtcttgaa cgttacctcg gcgcaaaatt    1740
ccctggcgca aaacgcttct cgctggaagg cggtgacgcg ttaatcccga tgcttaaaga    1800
gatgatccgc cacgctggca acagcggcac ccgcgaagtg gttctcggga tggcgcaccg    1860
tggtcgtctg aacgtgctgg tgaacgtgct gggtaaaaaa ccgcaagact tgttcgacga    1920
gttcgccggt aaacataaag aacacctcgg cacgggtgca gtgaaatacc acatgggctt    1980
ctcgtctgac ttccagaccg atggcggcct ggtgcacctg gcgctggcgt ttaacccgtc    2040
tcaccttgag attgtaagcc cggtagttat cggttctgtt cgtgcccgtc tggacagact    2100
tgatgagccg agcagcaaca aagtgctgcc aatcaccatc cacggtgacg ccgcagtgac    2160
cgggcagggc gtggttcagg aaaccctgaa catgtcgaaa gcgcgttatg aagttggttg    2220
cggtacggta cgtatcgtta tcaacaacca ggttggtttc accacctcta atccgctgga    2280
tgcccgttct acgccgtact gtactgatat cggtaagatg gttcaggccc cgattttcca    2340
cgttaacgcg gacgatccgg aagccgttgc ctttgtgacc cgtctggcgc tcgatttccg    2400
taacacctttt aaacgtgatg ttttcatcga cctggtgtgc taccgccgtc acggccacaa    2460
cgaagccgac gagccgagcg caacccagcc gctgatgtat cagaaaatca aaaaacatcc    2520
gacaccgcgc aaaatctacg ctgacaagct ggagcaggaa aaagtggcga cgctggaaga    2580
tgccaccgag atggttaacc tgtaccgcga tgcgctggat gctggcgatt gcgtagtggc    2640
agagtggcgt ccgatgaaca tgcactcttt cacctggtcg ccgtacctca accacgaatg    2700
ggacgaagag tacccgaaca aagttgagat gaagcgcctg cgaaacgcat    2760
cagcacggtg ccggaagcag ttgaaatgca gtctcgcgtt gccaagattt atggcgatcg    2820
ccaggcgatg gctgccggtg agaaactgtt cgactgggc ggtgcggaaa acctcgctta    2880
cgccacgctg gttgatgaag gcattccggt tcgcctgtcg ggtgaggact ccggtcgcgg    2940
taccttcttc caccgccacg cggtgatcca caaccagtct aacggttcca cttacacgca    3000
gctgcaacat atccataacg ggcagggcgc gttccgtgtc tgggactccg tactgtctga    3060
agaagcagtg ctggcgtttg aatatggtta tgccaccgca gaaccacgca ctctgaccat    3120
ctgggaagcg cagttcggtg acttcgccaa cggtgcgcag gtggttatcg accagttcat    3180
ctcctctggc aacagaaat ggggccggat gtgtggtctg gtgatgttgc tgccgcacgt    3240
ttacgaaggg caggggccgg agcactcctc cgcgcgtctg gaacgttatc tgcaactttg    3300
tgctgagcaa aacatgcagg tttgcgtacc gtctacccg gcacaggttt accacatgct    3360
gcgtcgtcag gcgctgcgcg ggatgcgtcg tccgctggtc gtgatgtcgc cgaaatccct    3420
gctgcgtcat ccgctggcgg tttccagcct cgaagaactg gcgaacggca cctcctgcc    3480
agccatcggt gaaatcgacg agcttgatcc gaagggcgtg aagcgcgtag tgatgtgttc    3540
tggtaaggtt tattacgacc tgctggaaca gcgtcgtaag aacaatcaac acgatgtcgc    3600
cattgtgcgt atcgagcaac tctacccgtt cccgcataaa gcgatgcagg aagtgttgca    3660
```

-continued

```
gcagtttgct cacgtcaagg attttgtctg gtgccaggaa gagccgctca accaggcgc   3720
atggtactgc agccagcatc atttccgtga agtgattccg tttgggcgtt ctctgcgtta   3780
tgcaggccgc ccggcctccg cctctccggc ggtagggtat atgtccgttc accagaaaca   3840
gcaacaagat ctggttaatg acgcgctgaa cgtcgaataa ataaaggata cacaatgagt   3900
agcgtagata ttctggtccc tgacctgcct gaatccgtag ccgatgccac cgtcgcaacc   3960
tggcataaaa aacccggcga cgcagtcgta cgtgatgaag tgctggtaga aatcgaaact   4020
gacaaagtgg tactggaagt accggcatca gcagacggca ttctggatgc ggttctggaa   4080
gatgaaggta caacggtaac gtctcgtcag atccttggtc gcctgcgtga aggcaacagc   4140
gccggtaaag aaaccagcgc caaatctgaa gagaaagcgt ccactccggc gcaacgccag   4200
caggcgtctc tggaagagca aaacaacgat gcgttaagcc cggcgatccg tcgcctgcta   4260
gctgaacaca atctcgacgc cagcgccatt aaaggcaccg gtgtgggtgg tcgtctgact   4320
cgtgaagatg tggaaaaaca tctggcgaaa gccccggcga aagagtctgc tccggcagcg   4380
gctgctccgg cggcgcaacc ggctctggct gcacgtagtg aaaaacgtgt cccgatgact   4440
cgcctgcgta agcgtgtggc agagcgtctg ctggaagcga aaaatccac cgccatgctg   4500
accacgttca acgaagtcaa catgaagccg attatggatc tgcgtaagca gtacggtgaa   4560
gcgtttgaaa aacgccacgg catccgtctg ggctttatgt ccttctacgt gaaagcggtg   4620
gttgaagccc tgaaacgtta cccggaagtg aacgcttcta tcgacggcga tgacgtggtt   4680
taccacaact atttcgacgt cagcatggcg gtttctacgc cgcgcggcct ggtgacgccg   4740
gttctgcgtg atgtcgatac cctcggcatg gcagacatcg agaagaaaat caaagagctg   4800
gcagtcaaag gccgtgacgg caagctgacc gttgaagatc tgaccggtgg taacttcacc   4860
atcaccaacg gtggtgtgtt cggttccctg atgtctacgc cgatcatcaa cccgccgcag   4920
agcgcaattc tgggtatgca cgctatcaaa gatcgtccga ggcgtggtaa tggtcaggtt   4980
gagatcctgc cgatgatgta cctggcgctg tcctacgatc accgtctgat cgatggtcgc   5040
gaatccgtgg gcttcctggt aacgatcaaa gagttgctgg aagatccgac gcgtctgctg   5100
ctggacgtgt agtagtttaa gtttcacctg cactgtagac cggataaggc attatcgcct   5160
tctccgcaa ttgaagcctg atgcgacgct gacgcgtctt atcaggccta cgggaccacc   5220
aatgtaggtc ggataaggcg caagcgccgc atccgacaag cgatgcctga tgtgacgttt   5280
aacgtgtctt atcaggccta cgggtgaccg acaatgcccg gaagcgatac gaaatattcg   5340
gtctacggtt taaaagataa cgattactga aggatggaca gaacacatga acttacatga   5400
atatcaggca aaacaacttt ttgcccgcta tggcttacca gcaccggtgg gttatgcctg   5460
tactactccg cgcgaagcag aagaagccgc ttcaaaaatc ggtgccggtc cgtggggtagt   5520
gaaatgtcag gttcacgctg gtgggccgcg taaagcgggc ggtgtgaaag ttgtaaacag   5580
caaagaggac atccgtgctt ttgcagaaaa ctggctgggc aagcgtctgg taacgtatca   5640
aacagatgcc aatggccaac cggttaacca gattctggtt gaagcagcga ccgatatcgc   5700
taaagagctg tatctcggtg ccgttgttga ccgtagttcc cgtcgtgtgg tctttatgcg   5760
ctccaccgaa ggcggcgtgg aaatcgaaaa agtggcggaa gaaactccgc acctgatcca   5820
taaagttgcg cttgatccgc tgactggccc gatgccgtat cagggacgcg agctggcgtt   5880
caaactgggt ctggaaggta aactggttca gcagttcacc aaaatcttca tgggcctggc   5940
gaccattttc ctggagcgcg acctggcgtt gatcgaaatc aacccgctgg tcatcaccaa   6000
acagggcgat ctgatttgcc tcgacggcgc aaa actgggcgct gacggcaacg cactgttccg   6060
ccagcctgat ctgcgcgaaa tgcgtgacca gtcgcaggaa gatccgcgtg aagcacaggc   6120
tgcacagtgg gaactgaact acgttgcgct ggacggtaac atcggttgta tggttaacgg   6180
cgcaggtctg gcgatgggta cgatggcaat cgttaaactg cacggcggcg aaccggctca   6240
cttccttgac gttggcggcg gcgcaaccaa agaacgtgta accgaagcgt tcaaaatcat   6300
cctctctgac gacaaagtga aagccgttct ggttaacatc ttcggcggta tcgttcgttg   6360
cgacctgatc gctgacggta tcatcggcgc ggtagcagaa gtgggtgtta acgtaccggt   6420
cgtggtacgt ctggaaggta acaacgccga actcggccgg aagaaactgg ctgacagcgg   6480
cctgaatatt attgcagcaa aaggtctgac ggatgcagct cagcaggttg ttgccgcagt   6540
ggaggggaaa taatgtccat tttaatcgat aaaaacacca aggttatctg ccagggcttt   6600
accggtagcc aggggacttt ccactcagaa caggccattg catacggcac taaaatggtt   6660
ggcggcgtaa ccccaggtaa aggcggcaca acccacctcg gcctgccggt gttcaacacc   6720
gtgcgtgaag ccgttgctgc cactggcgct accgcttctg ttatctacgt accagcaccg   6780
ttctgcaaag actccattct ggaagccatc gacgcaggca tcaaactgat tatcaccatc   6840
actgaaggca tcccgacgct ggatatgctg accgtgaaag tgaagctgga tgaagcaggc   6900
gttcgtatga tcggcccgaa ctgcccaggc gttatcactc cgggtgaatg caaaatcggt   6960
atccagcctg gtcacattca caaaccgggt aaagtgggta tcgtttcccg ttccggtaca   7020
ctgacctatg aagcggttaa acagaccacg gattacggtt tcggtcagtc gacctgtgtc   7080
ggtatcggcg gtgacccgat cccgggctct aactttatcg acattctcga aatgttcgaa   7140
aaagatccgc agaccgaagc gatcgtgatg atcggtgaga tcggcggtag cgctgaagaa   7200
gaagcagctc gtacatcaa agagcacgtt accaagccag ttgtgggtta catcgctggt   7260
gtgactgcgc cgaaaggcaa acgtatgggc cacgcgggtg ccatcattgc cggtgggaaa   7320
gggactgcgg atgagaaatt cgctgctctg gaagccgcag gcgtgaaaac cgttcgcagc   7380
ctggcggata tcggtgaagc actgaaaact gttctgaaat aaaggtccag gcatcaaata   7440
aaacgaaagg ctcagtcgaa agactgggcc tttcgtttta tctgttgttt gtcggtgaac   7500
gctctctact agagtcacac tggctcacct tcgggtgggc ctttctgcgt ttatactcga   7560
gtgccacctg acgtctaaga aaccattatt atcatgacat taacctataa aaataggcgt   7620
atcacgaggc agaatttcag ataaaaaaaa tccttagctt tcgctaagga tgatttctgg   7680
aattcgcggc cgcttctaga gactagtgga agacatcgct agagaccctgc accatatgcg   7740
gtgtgaaata ccgcacagat gcgtaaggag aaaataccgc atcaggcgcc attcgccatt   7800
caggctgcgc aactgttggg aagggcgatc ggtgcgggcc tcttcgctat tacgccagct   7860
ggcgaaaggg ggatgtgctg caaggcgatt aagttgggta acgccagggt tttcccagtc   7920
acgacgttgt aaaacgacgg ccagtgaatt cgagctcggt acccggggat cctctagagt   7980
cgacctgcag gcatgcaagc ttggcgtaat catggtcata gctgtttcct gtgtgaaatt   8040
gttatccgct cacaattcca cacaacatac gagccggaag cataaagtgt aaagcctggg   8100
gtgcctaatg agtgagctaa ctcacattaa ttgcgttgcg ctcactgccc gctttccagt   8160
cgggaaacct gtcgtgccag ctgcattaat gaatcggcca acgcgcgggg gtttataaaa   8220
tcccgtcaag tcagcgtaat gctctgccag tgttacaacc aattaaccaa ttctgattag   8280
aaaaactcat cgagcatcaa atgaaactgc aatttattca tatcaggatt atcaatacca   8340
tatttttgaa aaagccgttt ctgtaatgaa ggagaaaact caccgaggca gttccatagg   8400
```

```
atggcaagat cctggtatcg gtctgcgatt ccgactcgtc caacatcaat acaacctatt   8460
aatttccct cgtcaaaaat aaggttatca agtgagaaat caccatgagt gacgactgaa   8520
tccggtgaga atggcaaaag cttatgcatt tctttccaga cttgttcaac aggccagcca   8580
ttacgctcgt catcaaaatc actcgcatca accaaaccgt tattcattcg tgattgcgcc   8640
tgagcgagac gaaatacgcg atcgctgtta aaaggacaat tacaaacagg aatcgaatgc   8700
aaccggcgca ggaacactgc cagcgcatca acaatatttt cacctgaatc aggatattct   8760
tctaataccct ggaatgctgt tttcccgggg atcgcagtgg tgagtaacca tgcatcatca   8820
ggagtacgga taaaatgctt gatggtcgga agaggcataa attccgtcag ccagtttagt   8880
ctgaccatct catctgtaac atcattggca acgctacctt tgccatgttt cagaaacaac   8940
tctggcgcat cgggcttccc atacaatcga tagattgtcg cacctgattg cccgacatta   9000
tcgcgagccc atttataccc atataaatca gcatccatgt tggaatttaa tcgcggcctg   9060
gagcaagacg tttcccgttg aatatggctc ataacacccc ttgtattact gtttatgtaa   9120
gcagacagtt ttattgttca tgatgatata tttttatctt gtgcaatgta acatcagaga   9180
ttttgagaca caacgtggct ttgttgaata aatcgaactt ttgctgagtt gaaggatcag   9240
ggtctcttgc catgtcttct actagtagcg gccgctgcag tccggcaaaa aagggcaagg   9300
tgtcaccacc ctgccctttt tctttaaaac cgaaaagatt acttcgcgtt atgcaggctt   9360
cctcgctcac tgactcgctg cgctcggtcg ttcggctgcg gcgagcggta tcagctcact   9420
caaaggcggt aatacggtta ccacagaat caggggataa cgcaggaaag aacatgtgag   9480
caaaaggcca gcaaaaggcc aggaaccgta aaaaggc                           9517
```

SEQ ID NO: 8                   moltype = DNA   length = 7116
FEATURE                        Location/Qualifiers
source                         1..7116
                               mol_type = genomic DNA
                               organism = Escherichia coli
SEQUENCE: 8

```
tactgcgcca tccgttagca gttagcagcc tggaggaact ggcaaacggt acgttcttgc   60
cagctatcgg cgaaatcgat gaactggatc ctaaaggggt gaaacgcgtt gttatgtgtt   120
ctggtaaagt gtattatgat cttttggaac agcgtcgcaa aaataatcag cacgatgtag   180
ctattgtgcg gatcgagcag ctgtatccgt ccccgcacaa agcaatgcag gaagtgctgc   240
agcagttcgc acatgtcaaa gattttgtct ggtgtcagga ggaaccgctt aatcaggggg   300
cctggtattg tagtcagcac catttccggg aggtgatccc gtttggggcg tccttacggt   360
atgctggtcg ccctgcctcc gcaagtccgg ccgtgggata tatgagcgtt caccagaaac   420
agcagcagga tttggtgaat gatgctttga atgtggaatg aatgtccatc ctgatcgaca   480
aaaacactaa agtaatttgt cagggcttta ccggttccca gggcacattt cactcagagc   540
aggccatcgc ttatgggacc aaaatggtgg gtggtgtaac gcctggtaaa ggaggcacca   600
cccatctggg tttgccggta tttaataccg tgcgtgaggc ggttgccgca accggtgcca   660
cggcttcagt tatctatgtt cctgccccat tttgtaaaga ttcaattctg gaagctattg   720
atgcgggcat caaattgatt attacgatta ccgaaggtat ccctacgctg gatatgttga   780
cggttaaagt gaaacttgat gaagcggggg tacgcatgat tggtccgaat tgtccgggcg   840
ttattactcc aggtgagtgc aaaattggta ttcagccggg tcatattcac aaacctggga   900
aagtcggaat tgtgtctcgt tctggcactc tgacgtatga ggcagttaaa cagaccacag   960
attatgaggct tgggcagagt acctgtgtcg gcatcggagg cgatcctatt ccggggagta   1020
attttatcga tattctggaa atgtttgaga aagatccgca gaccgaggca atcgtcatga   1080
ttggcgagat tggcggttcc gcggaagaag aagctcagc ctatatcaaa gaacatgtca   1140
caaaaccggt agtgggctat atcgcgggag tcacggcccc aaaaggtaaa cgtatgggcc   1200
atgccgagc gatcatcgcg ggcggcaaag gcactgcaga tgaaaaattt gcagcccttg   1260
aggccgctgg cgtaaaaacg gtccgttccc ttgctgatat tggtgaagca ctgaaaaccg   1320
tgttgaaata aaggtccagg catcaaataa aacgaaaggc tcagtcgaaa gactgggcct   1380
ttcgttttat ctgttgtttg tcggtgaacg ctctctacta gagtcacact ggctcacctt   1440
cggggtgggc tttctgcgtt tatatcccgt caagtcagcg taatgctctg ccagtgttac   1500
aaccaattaa ccaattctga ttagaaaaac tcatcgagca tcaaatgaaa ctgcaattta   1560
ttcatatcag gattatcaat accatatttt tgaaaaagcc gtttctgtaa tgaaggagaa   1620
aactcaccga ggcagttcca taggatggca agatcctggt atcggtctgc gattccgact   1680
cgtccaacat caatacaacc tattaatttc ccctcgtcaa aataaggttat atcaagtgag   1740
aaatcaccat gagtgacgac tgaatccggt gagaatggca aaagcttatg catttctttc   1800
cagacttgtt caacaggcca gccattacgc tcgtcatcaa aatcactcgc atcaaccaaa   1860
ccgttattca ttcgtgattg cgcctgagcg agacgaaata cgcgatcgct gttaaaagga   1920
caattacaaa caggaatcga atgcaaccgg cgcaggaaca ctgccagcgc atcaacaata   1980
ttttcacctg aatcaggata ttcttctaat acctggaatg ctgtttttcc ggggatcgca   2040
gtggtgagta accatgcatc atcaggagta cggataaaat gcttgatggt cggaagaggc   2100
ataaattccg tcagccagtt tagtctgacc atctcatctg taacatcatt ggcaacgcta   2160
cctttgccat gtttcagaaa caactctggc gcatcgggct cccatacaa tcgatagatt   2220
gtcgcacctg attgcccgac attatcgcga gcccatttat accatataaa atcagcagca   2280
atgttggaat ttaatcgcgg cctggagcaa gacgtttccc gttgaatatg gctcataaca   2340
ccccttgtat tactgtttat gtaagcagac agtttttattg ttcatgatga tatatttttta   2400
tcttgtgcaa tgtaacatca gagattttga gacacaacgt ggctttgttg aataaatcga   2460
actttgctgt agttgaagga tcagctgag tgccacctga cgtctaagaa accattatta   2520
tcatgacatt aacctataaa aataggcgta tcacgaggca gaatttcaga taaaaaaaat   2580
ccttagcttt cgctaaggat gatttctgga attcgcggcc gcttctagag actagtggaa   2640
gacatcgctg gaaagtgaaa cgtgatttca tgcgtcattt tgaacatttt gtaaatctta   2700
tttaataatg tgtgcggcaa ttcacattta atttatgaat gtttttcttaa catcgcggca   2760
actcaagaaa cggcaggttc ggatcttagc tactagagaa agaggagaaa tactagatgc   2820
gtaaaggcga gagctgttca actggtgtcg tccctattct ggtggtactg gatggtgatg   2880
tcaacggtca taagttttcc gtgcgtggcg agggtgaagg tgacgcaact aatggtaaac   2940
tgacgctgaa gttcatctgt actactggta aactgccggt tccttggccg actctggtaa   3000
cgacgctgac ttatggtgtt cagtgctttg ctcgttatcc ggaccatatg aagcagcatg   3060
acttcttcaa gtccgccatg ccggaaggct atgtgcagga acgcacgatt tcctttaagg   3120
atgacggcac gtacaaaacg cgtgcggaag tgaaatttga aggcgatacc ctggtaaacc   3180
```

-continued

```
gcattgagct gaaaggcatt gactttaaag aggacggcaa tatcctgggc cataagctgg   3240
aatacaattt taacagccac aatgtttaca tcaccgccga taaacaaaaa aatggcatta   3300
aagcgaattt taaaattcgc cacaacgtgg aggatggcag cgtgcagctg gctgatcact   3360
accagcaaaa cactccaatc ggtgatggtc ctgttctgct gccagacaat cactatctga   3420
gcacgcaaag cgttctgtct aaagatccga acgagaaacg cgatcatatg gttctgctgg   3480
agttcgtaac cgcagcgggc atcacgcatg gtatggatga actgtacaaa tgaccaggca   3540
tcaaataaaa cgaaaggctc agtcgaaaga ctgggccttt cgttttatct gttgtttgtc   3600
ggtgaacgct ctctactaga gtcacactgg ctcaccttcg ggtgggcctt tctgcgttta   3660
tacgtgccat gtcttctact agtagcggcc gctgcagtcc ggcaaaaaag ggcaaggtgt   3720
caccaccctg cccttttct ttaaaaccga aagattact tcgcgttatg caggcttcct    3780
cgctcactga ctcgctgcgc tcggtcgttc ggctgcggcg agcggtatca gctcactcaa   3840
aggcggtaat acggttatcc acagaatcag gggataacgc aggaaagaac atgtgagcaa   3900
aaggccagca aaaggccagg aaccgtaaaa aggccgcgtt gctggcgttt ttccacaggc   3960
tccgcccccc tgacgagcat cacaaaaatc gacgctcaag tcagaggtgg cgaaacccga   4020
caggactata aagataccag gcgtttcccc ctggaagctc cctcgtgcgc tctcctgttc   4080
cgaccctgcc gcttaccgga tacctgtccg cctttctccc ttcgggaagc gtggcgcttt   4140
ctcatagctc acgctgtagg tatctcagtt cggtgtaggt cgttcgctcc aagctgggct   4200
gtgtgcacga accccccgtt cagcccgacc gctgcgcctt atccggtaac tatcgtcttg   4260
agtccaaccc ggtaagacac gacttatcgc cactggcagc agccactggt aacaggatta   4320
gcagagcgag gtatgtaggc ggtgctacag agttcttgaa gtggtggcct aactacggct   4380
acactagaag aacagtattt ggtatctgcg ctctgctgaa gccagttacc ttcggaaaaa   4440
gagttggtag ctcttgatcc ggcaaacaaa ccaccgctgg tagcggtggt tttttttgtt   4500
gcaagcagca gattacgcgc agaaaaaaag gatctcaaga agatcctttg atcttttcta   4560
cggggtctga cgctcagtgg aacgaaaact cacgttaagg gattttggtc atgagattat   4620
caaaaaggat cttcacctag atccttttaa attaaaaatg aagttttaaa tcaatctaaa   4680
gtatatatga gtaaacttgg tctgacagct cgagtttacg gctagctcag tcctaggtat   4740
agtgctagct acttgttaga aaagagaagc acgtaatgca gaactcagca ttgaaagcat   4800
ggcttgatag ctcctattta tcaggtgcta accagagctg gattgaacag ctgtatgaag   4860
attttctgac agatccggat tcagtggatg cgaattggcg cagcacttt cagcagttgc    4920
ctggcaccgg tgtaaaaccg gatcagtttc attcccagac gcgggagtat tttcgtcgtc   4980
tggcgaaaga tgcgagccgg tattcaagta caatttctga tccggatacg aatgtaaaac   5040
aggtgaaagt gcttcagtta attaatgcgt atcgctttag aggccatcag catgcgaatc   5100
tggatccgct gggcttatgg cagcaggata aagtcgcgga tctggatcca agttttcacg   5160
atttaacgga agctgatttt caggaaacct ttaacgtcag ctcattcgca agtgggaaag   5220
aaacaatgaa actgggcgaa cttcttgagg cgctgaaaca gacttattgt ggccctattg   5280
gtgcggaata tatgcatatt acctcaactg aagagaaacg ttggattcag cagagaatcg   5340
agagtggccg cgcgactttt aactccgaag aaaaaaaaag attcctgtca gaactgacag   5400
ccgcggaagg cttagagcgg tatttgggtg ccaaattccc aggagcaaaa cggttcagcc   5460
tggagggcg tgatgcgctg atcccgatgc tgaaagaaat gattcggcat gcgggaaata   5520
gcggaactcg ggagtggtg ttaggaatgg cacaccgcgg ccgtttgaat gtactggtta    5580
acgtattagg aaaaaaacct caggatttat ttgatgagtt cgcgggaaaa cataaagaac   5640
atctgggcac tggtgatgtc aaatatcaca tgggcttctc aagtgatttt cagacgatg    5700
gaggtcggt tcacctggca ctggcattta atccttctca tctggaaatc gtaagtcgg     5760
tcgttattgg ttccgtgcgc gctcgcttag atcggttaga tgaacctagc tcaaacaaag   5820
ttttaccaat cacgatccat ggggatgcag ctgttaccgg acagggtgtt gtgcaggaga   5880
ctttgaatat gtccaaagcg cgcgggtatg aggtgggtgg tacggtgcgt attgttatca   5940
ataatcaggt gggtttaca accagtaacc ctctggatg tcgctctacg ccgtattgca     6000
ctgatattgg taaaatggtg caggcaccaa tttttcacgt caatgccgat gatccggaag   6060
ctgttgcctt tgttacgcgc ctggctctgg attttcgtaa cactttcaaa cgtgatgtat   6120
ttatcgattt agtatgctat cgtcgtcatg gtcataatga ggctgatgaa cctagcgcta   6180
cccagccact gatgtatcag aaaattaaaa aacatcctac ccctcgtaaa atttatgcgg   6240
ataaactgga gcaggaaaaa gtggctactc ttgaagatgc tactgaaatg gtcaatcttt   6300
atcgggatgc attggatgcg ggtgattgcg tggtcgcgga atggcgcccg atgaatatgc   6360
attcatttac ttggtcaccg tatttaaatc atgagtggga tgaggaatat ccgaataaag   6420
tggagatgaa acgcctgcag gaattagcaa aacgtattag cacagtacct gaagcggttg   6480
agatgcagtc tagagttgcc aaaatctatg gagatcgcca ggccatggca gcagggggaaa   6540
aacttttga ttggggggga gccgaaaacc tggcatatgc gacgctggta gatgagggca    6600
ttccggtgcg cctttctggt gaagattctg gcgcgggtac tttttttcat cggcacgctg   6660
ttattcataa ccagtctaac ggtagtactt atactccgct gcagcacatc cacaatggtc   6720
agggtgcgtt ccgtgtatgg gattccgtgc tgagtgaaga agcggttctt gcgtttgagt   6780
atgggtatgc aactgccgag ccacgcacgc tgacgatctg ggaagcccag tttggcgatt   6840
ttgcaaatgt gcccaggtg gtaatcgatc agtttattag ctccggcgaa cagaaatggg    6900
ggcggatgtg tggtttagtt atgttgttac cgcatggcta tgaaggtcag ggacctgagc   6960
acagctcagc gcgcctggaa cgctatcttc agctgtgtgc ggaacagaac atgcaggtat   7020
gcgttccttc cacgccggct caggtttatc atatgttaag acgtcaggcc ttgcgcggta   7080
tgcggcgccc gttggtcgtg atgtcccga aaagtt                              7116
```

SEQ ID NO: 9               moltype = DNA    length = 10025
FEATURE                    Location/Qualifiers
source                     1..10025
                           mol_type = genomic DNA
                           organism = Escherichia coli SEQUENCE: 9
```
cgcgttgctg gcgttttttcc acaggctccg ccccctgac gagcatcaca aaaatcgacg    60
ctcaagtcag aggtggcgaa acccgacagg actataaaga taccaggcgt ttccccctgg   120
aagctccctc gtgcgctctc ctgttccgac cctgccgctt accggatacc tgtccgcctt   180
tctcccttcg ggaagcgtgg cgctttctca tagctcacgc tgtaggtatc tcagttcggt   240
gtaggtcgtt cgctccaagc tgggctgtgt gcacgaaccc cccgttcagc ccgaccgctg   300
cgccttatcc ggtaactatc gtcttgagtc caacccggta agacacgact tatcgccact   360
```

-continued

```
ggcagcagcc actggtaaca ggattagcag agcgaggtat gtaggcggtg ctacagagtt  420
cttgaagtgg tggcctaact acggctacac tagaagaaca gtatttggta tctgcgctct  480
gctgaagcca gttaccttcg gaaaaagagt tggtagctct tgatccggca aacaaaccac  540
cgctggtagc ggtggttttt ttgtttgcaa gcagcagatt acgcgcagaa aaaaaggatc  600
tcaagaagat cctttgatct tttctacggg gtctgacgct cagtggaacg aaaactcacg  660
ttaagggatt ttggtcatga gattatcaaa aaggatcttc acctagatcc tttttaaatta  720
aaaatgaagt tttaaatcaa tctaaagtat atatgagtaa acttggtctg acagctcgag  780
gtaggcctga taagacgcgc aagcgtcgca tcaggcaacc agtgccggat gcggcgtgaa  840
cgccttatcc ggcctacaag tcattacccg taggcctgac aagcgcagcg catcaggcgt  900
aacaaagaaa tgcaggaaat ctttaaaaac tgccctgac actaagacag tttttaaagg  960
ttccttcgcg agccactacg tagacaagag ctcgcaagtg aaccccggca cgcacatcac  1020
tgtgcgtggt agtatccacg gcgaagtaag cataaaaaag atgcttaagg gatcacgaat  1080
gcagaacagc gctttgaaag cctggttgga ctcttcttac ctctctggcg caaaccagag  1140
ctggatagaa cagctctatg aagatttctt aaccgatcct gactcggttg acgctaactg  1200
gcgttcgacg ttccagcagt tacctggtac gggagtcaaa ccggatcaat tccactctca  1260
aacgcgtgaa tatttccgcc gcctggcgaa agacgcttca cgttactctt caacgatctc  1320
cgaccctgac accaatgtga agcaggttaa agtcctgcag ctcattaacg cataccgctt  1380
ccgtcgtcac cagcatgcga atctcgatcc gctgggactg tggcagcaag ataaagtggc  1440
cgatctggat ccgtctttcc acgatctgac cgaagcagac ttccaggaga ctttcaacgt  1500
cggttcattt gccagcggca aagaaaccat gaaactcggc gagctgctgg aagccctcaa  1560
gcaaacctac tgcggcccga ttggtgccga gtatatgcac attaccagca ccgaagaaaa  1620
acgctggatc caacagcgta tcgagtctgg tcgcgcgact ttcaatagcg aagagaaaaa  1680
acgcttctta agcgaactga ccgccgctga aggtcttgaa cgttacctcg gcgcaaaatt  1740
ccctggcgca aaacgcttct cgctggaagg cggtgacgcg ttaatcccga tgcttaaaga  1800
gatgatccgc cacgctggca acagcggcac ccgcgaagtg gttctcggga tggcgcaccg  1860
tggtcgtctg aacgtgctgg tgaacgtgct gggtaaaaaa ccgcaagact tgttcgacga  1920
gttcgccggt aaacataaag aacacctcgg cacgggtgac gtgaaatacc acatgggctt  1980
ctcgtctgac ttccagaccg atggcggcct ggtgcacctg gcgctggcgt ttaacccgtc  2040
tcaccttgag attgtaagcc cggtagttat cggttctgtt cgtgcccgtc tggacagact  2100
tgatgagccg agcagcaaca aagtgctgcc aatcaccatc cacggtgacg ccgcagtgac  2160
cgggcagggc gtggttcagg aaaccctgaa catgtcgaaa gcgcgtggtt atgaagttgac  2220
cggtacggta cgtatcgtta tcaacaacca ggttggtttc accacctcta atccgctgga  2280
tgcccgttct acgccgtact gtactgatat cggtaagatg gttcaggccc cgattttcca  2340
cgttaacgcg gacgatccgg aagccgttgc ctttgtgacc cgtcttggcgc tgtatttccg  2400
taacaccttt aaacgtgatg ttttcatcga cctggtgtgc taccgccgtc acggccacaa  2460
cgaagccgac gagccgagcg caacccagcc gctgatgtat cagaaaatca aaaaacatcc  2520
gacaccgcgc aaaatctacg ctgacaagct ggagcaggaa aaagtggcga cgctggaaga  2580
tgccaccgag atggttaacc tgtaccgcga tgcgctggat gctggcgatt gcgtagtggc  2640
agagtggcgt ccgatgaaca tgcactcttt cacctggtcg ccgtacctca accacgaatg  2700
ggacgaagag tacccgaaca aagttgagat gaagcgcctg caggagctgg cgaaacgcat  2760
cagcacggtg ccggaagcag ttgaaatgca gtctcgcgtt gccaagattt atggcgatcg  2820
ccaggcgatg gctgccggtg agaaactgtt cgactggggc ggtgcggaaa acctcgctta  2880
cgccacgccg gttgatgaag gcattccggt tcgcctgtcg ggtgaggact ccggtcgcgg  2940
taccttcttc caccgccacg cggtgatcca caaccagtct aacggttcca cttacacgcc  3000
gctgcaacat atccataacg ggcagggcgc gttccgtgtc tgggactccg tactgtctga  3060
agaagcagtg ctggcgtttg aatatggtta tgccaccgca gaaccacgca ctctgaccat  3120
ctgggaagcg cagttcggtg acttcgccaa cggtgcgcag gtggttatcg accagttcat  3180
ctcctctggc gaacagaaat ggggccggat gtgtggtctg gtgatgttgc tgccgcacgg  3240
ttacgaaggg caggggccgg agcactcctc cgcgcgtctg gaacgttatc tgcaactttg  3300
tgctgagcaa aacatgcagg tttgcgtacc gtctaccccg gcacaggttt accacatgct  3360
gcgtcgtcag gcgctgcgcg ggatgcgtcg tccgct ggtc gtgatgtcgc cgaaatccct  3420
gctgcgtcat ccgctggcgg tttccagcct cgaagaactg gcgaacggca ccttcctgcc  3480
agccatcggt gaaatcgacg agcttgatcc gaagggcgtg aagcgcgtag tgatgtgttc  3540
tggtaaggtt tattacgacc tgctggaaca gcgtcgtaag aacaatcaac acgatgtcgc  3600
cattgtgcgt atcgagcaac tctacccgtt cccgcataaa ggtgcgcagg aagtgttgca  3660
gcagtttgct cacgtcaagg attttgtctg gtgccaggaa gagccgctca accagggcgc  3720
atggtactgc agccagcatc atttccgtga agtgattccg tttgggggctt ctctgcgtta  3780
tgcaggccgc ccggcctccg cctctccggc ggtagggtat atgtccgttc accagaaaca  3840
gcaacaagat ctggttaatg acgcgctgaa cgtcgaataa ataaaggata cacaatgagt  3900
agcgtagata ttctggtccc tgacctgcct gaatccgtag ccgatgccac cgtcgcaacc  3960
tggcataaaa aacccggcga cgcagtcgta cgtgatgaag tgctggtaga aatcgaaact  4020
gacaaagtgg tactggaagt accggcatca gcagacggca ttctggatgc ggttctggaa  4080
gatgaaggta caacggtaac gtctcgtcag atccttggtc gcctgcgtga aggcaacagc  4140
gccggtaaag aaaccagcgc caaatctgaa gagaaagcgt ccactccggc gcaacgccag  4200
caggcgtctc tggaagagca aaacaacgat gcgttaagcc cggcgatccg tcgcctgctg  4260
gctgaacaca atctcgacgc cagcgccatt aaaggcaccg gtgtgggtgg tcgtctgact  4320
cgtgaagatg tggaaaaaca tctggcgaaa gccccggcga aagagtctgc tccggcagcg  4380
gctgctccgg cggcgcaacc ggctctggct gcacgtagtg aaaaacgtgt cccgatgact  4440
cgcctgcgta aagcgtgtgc agagcgtctg ctggaagcga aaaactccgac cgccatgctg  4500
accacgttca acgaagtcaa catgaagccg attatggatc tgcgtaagca gtacggtgaa  4560
gcgtttgaaa aacgccacgg catccgtctg ggctttatgt ccttctacgt gaaagcggtg  4620
gttgaagccc tgaaacgtta cccggaagtg aacgcttcta tcgacggcga tgacgtggtt  4680
taccacaact atttcgacgt cagcatggcg gtttctacgc cgcgcggcct ggtgacgccg  4740
gttctgcgtga atgtcgatac cctcggcatg gcagacatcg agaagaaaat caaagagctg  4800
gcagtcaaag gccgtgacgg caagctgacc gttgaagatc tgaccggtgg taacttcacc  4860
atcaccaacg gtggtgtgtt cggttccctg atgtctacgc cgatcatcaa cccgccgcag  4920
agcgcaattc tgggtatgca cgctatcaaa gatcgtccga tggcggtgaa tggtcaggtt  4980
gagatcctgc cgatgatgta cctggcgctg tcctacgatc accgtctgat cgatggtcgc  5040
gaatccgtgg gcttcctggt aacgatcaaa gagttgctgg aagatccgac gcgtctgctg  5100
```

-continued

```
ctggacgtgt agtagtttaa gtttcacctg cactgtagac cggataaggc attatcgcct   5160
tctccggcaa ttgaagcctg atgcgacgct gacgcgtctt atcaggccta cgggaccacc   5220
aatgtaggtc ggataaggcg caagcgccgc atccgacaag cgatgcctga tgtgacgttt   5280
aacgtgtctt atcaggccta cgggtgaccg acaatgcccg gaagcgatac gaaatattcg   5340
gtctacggtt taaaagataa cgattactga aggatggaca gaacacatga acttacatga   5400
atatcaggca aaacaacttt ttgcccgcta tggcttacca gcaccggtgg gttatgcctg   5460
tactactccg cgcgaagcag aagaagccgc ttcaaaaatc ggtgccggtc cgtgggtagt   5520
gaaatgtcag gttcacgctg gtggccgcgg taaagcgggc ggtgtgaaag ttgtaaacag   5580
caaagaggac atccgtgctt ttgcagaaaa ctggctgggc aagcgtctgg taacgtatca   5640
aacagatgcc aatggccaac cggttaacca gattctggtt gaagcagcga ccgatatcgc   5700
taaagagctg tatctcggtg ccgttgttga ccgtagttcc cgtcgtgtgg tctttatggc   5760
ctccaccgaa ggcggcgtgg aaatcgaaaa agtggcggaa gaaactccgc acctgatcca   5820
taaagttgcg cttgatccgc tgactggccc gatgccgtat cagggacgcg agctggcgtt   5880
caaactgggt ctggaaggta aactggttca gcagttcacc aaaatcttca tgggcctggc   5940
gaccatttttc ctggagcgcg acctggcgtt gatcgaaatc aacccgctgg tcatcaccaa   6000
acagggcgat ctgatttgcc tcgacggcaa actgggcgct gacggcaacg cactgttccg   6060
ccagcctgat ctgcgcgaaa tgcgtgacca gtcgcaggaa gatccgcgtg aagcacaggc   6120
tgcacagtgg gaactgaact acgttgcgct ggacggtaac atcggttgta tggttaacgg   6180
cgcaggtctg gcgatgggta cgatggacat cgttaaactg cacggcgcg aaccggctaa    6240
cttccttgac gttggcggcg gcgcaaccaa agaacgtgta accgaagcgt tcaaaatcat   6300
cctctctgac gacaaagtga aagccgttct ggttaacatc ttcggcggta tcgttcgttg   6360
cgacctgatc gctgacggta tcatcggcgc ggtagcgaac gtgggtgtta acgtaccggt   6420
cgtggtacgt ctggaaggta acaacgccga actcggcgcg aagaaactgg ctgacagcgg   6480
cctgaatatt attgcagcaa aaggtctgac ggatgcagct cagcaggttg ttgccgcagt   6540
ggagggggaaa taatgtccat tttaatcgat aaaaacacca aggttatctg ccagggcttt   6600
accggtagcc aggggacttt ccactcagaa caggccattg catacggcac taaaatggtt   6660
ggcggcgtaa ccccaggtaa aggcggcacc acccacctcg gcctgccggt gttcaacacc   6720
gtgcgtgaag ccgttgctgc cactggcgct accgcttctg ttatctacgt accagcaccg   6780
ttctgcaaag actccattct ggaagccatc gacgcaggca tcaaactgat tatcaccatc   6840
actgaaggca tcccgacgct ggatatgctg accgtgaaag tgaagctgga tgaagcaggc   6900
gttcgtatga tcggcccgaa ctgcccaggc gttatcactc cgggtgaatg caaaatcggt   6960
atccagcctg gtcacattca caaaccgggc aaagtgggta tcgtttcccg ttccggtaca   7020
ctgacctatg aagcggttaa acagaccacg gattacggtt tcggtcagtc gacctgtgtc   7080
ggtatcggcg gtgaccgagc cccgggctct aactttatcg acattctcga aatgttcgaa   7140
aaagatccgc agaccgaagc gatcgtgatg atcggtgaga tcggcggtag cgctgaagaa   7200
gaagcagctg cgtacatcaa agagcacgtt accaagccag ttgtgggtta catcgctggt   7260
gtgactgcgc cgaaaggcaa acgtatgggc cacgcgggtg ccatcattgc cggtgggaaa   7320
gggactgcgg atgagaaatt cgctgctctg gaagccgcag gcgtgaaaac cgttcgcagc   7380
ctggcggata tcggtgaagc actgaaaact gttctgaaat aaaggtccag gcatcaaata   7440
aaacgaaagg ctcagtcgaa agactgggcc tttcgtttta tctgttgttt gtcggtgaac   7500
gctctctact agagtcacac tggctcacct tcgggtgggc ctttctgcgt ttatatcccg   7560
tcaagtcagc gtaatgctct gccagtgtta caaccaatta accaattctg attagaaaaa   7620
ctcatcgagc atcaaatgaa actgcaattt attcatatca ggattatcaa taccatattt   7680
ttgaaaaagc cgtttctgta atgaaggaga aaactcaccg aggcagttcc ataggatggc   7740
aagatcctgg tatcggtctg cgattccgac tcgtccaaca tcaatacaac ctattaattt   7800
cccctcgtca aaaataaggt tatcaagtga gaaatcacca tgagtgacga ctgaatccgg   7860
tgagaatggc aaaagcttat gcatttcttt ccagacttgt tcaacaggcc agccattacg   7920
ctcgtcatca aaatcactcg catcaaccaa accgttattc attcgtgatt gcgcctgagc   7980
gagacgaaat acgcgatcgc tgttaaaagg acaattacaa acaggaatcg aatgcaaccg   8040
gcgcaggaac actgccagcg catcaacaat attttcacct gaatcaggat attcttctaa   8100
tacctggaat gctgttttcc cggggatcgc agtggtgagt aaccatgcat catcaggagt   8160
acggataaaa tgcttgatgg tcggaagagg cataaaattc gtcagccagt ttagtctgac   8220
catctcatct gtaacatcat tggcaacgct acctttgcca tgtttcagaa acaactctgg   8280
cgcatcgggc ttcccataca atcgatagat tgtcgcacct gattgcccga cattatcgcg   8340
agcccattta tacccatata aatcagcatc catgttggaa tttaatcgcg gcctggagca   8400
agacgtttcc cgttgaatat ggctcataac accccttgta ttactgttta tgtaagcaga   8460
cagttttatt gttcatgatg atatattttt atcttgtgca atgtaacatc agagattttg   8520
agacacaacg tggctttgtt gaataaatcg aactttttgct gagttgaagg atcagctcga   8580
gtgccacctg acgtctaaga aaccattatt atcatgacat taacctataa aaataggcgt   8640
atcacgaggc agaatttcag ataaaaaaaa tccttagctt tcgctaagga tgatttctgg   8700
aattcgcggc cgcttctaga gactagtgga agacatcgct ggaaagtgaa acgtgatttc   8760
atgcgtcatt ttgaacattt tgtaaatctt atttaataat gtgtgcggca attcacattt   8820
aatttatgaa tgttttctta acatcgcggc aactcaagaa acgcaggtt cggatcttag    8880
ctactagaga aagaggagaa atactagatg cgtaaaggcg aagagctgtt cactggtgtc   8940
gtccctattc tggtggaact ggatggtgat gtcaacggtc ataagttttc cgtgcgtggc   9000
gagggtgaag gtgacgcaac taatggtaaa ctgacgctga gttcatctg tactactggt    9060
aaactgccgg ttccttggcc gactctggta acgacgctga cttatggtgt tcagtgcttt   9120
gctcgttatc cggaccatat gaagcagcat gacttcttca agtccgccat gccggaaggc   9180
tatgtgcagg aacgcacgat ttcctttaag gatgacggca cgtacaaaac gcgtgcgaaa   9240
gtgaaatttg aaggcgatac cctggtaaac cgcattgagc tgaaaggcat tgactttaaa   9300
gaggacggca atatcctggg ccataagctg gaatacaatt ttaacagcca caatgtttac   9360
atcaccgcca taaacaaaa aaatggcatt aaagcgaatt ttaaaattcg ccacaacgtg    9420
gaggatggca gcgtgcagct ggctgatcac taccagcaaa acactccaat cggtgatggt   9480
cctgttctgc tgccagacaa tcactatctg agcacgcaaa gcgttctgtc taaagatccg   9540
aacgagaaac gcgatcatat ggttctgctg gagttcgtaa ccgcagcggg catcacgcat   9600
ggtatggatg aactgtacaa atgaccaggc atcaaataaa acgaaaggct cagtcgaaag   9660
actgggcctt tcgttttatc tgttgtttgt cggtgaacgc tctctactag agtcacactg   9720
gctcaccttg gggtgggcct ttctgcgttt atacgtgcca tgtcttctac tagtagcggc   9780
cgctgcagtc cggcaaaaaa gggcaaggtg tcaccaccct gcccttttttc tttaaaaccg   9840
```

```
aaaagattac ttcgcgttat gcaggcttcc tcgctcactg actcgctgcg ctcggtcgtt   9900
cggctgcggc gagcggtatc agctcactca aaggcggtaa tacggttatc cacagaatca   9960
ggggataacg caggaaagaa catgtgagca aaaggccagc aaaaggccag gaaccgtaaa   10020
aaggc                                                                10025

SEQ ID NO: 10              moltype = DNA   length = 5088
FEATURE                    Location/Qualifiers
source                     1..5088
                           mol_type = genomic DNA
                           organism = Escherichia coli
SEQUENCE: 10
ggatggacag aacacatgaa cttacatgaa tatcaggcaa aacaactttt tgcccgctat    60
ggcttaccag caccggtggg ttatgcctgt actactccgc gcgaagcaga agaagccgct   120
tcaaaaatcg gtgccggtcc gtgggtagtg aaatgtcagg ttcacgctgg tggccgcggt   180
aaagcgggcg gtgtgaaagt tgtaaacagc aaagaggaca tccgtgcttt tgcagaaaac   240
tggctgggca agcgtctggt aacgtatcaa acagatgcca atggccaacc ggttaaccag   300
attctggttg aagcagcgac cgatatcgct aaagagctgt atctcggtgc cgttgttgac   360
cgtagttccc gtcgtgtggt ctttatggcc tccaccgaag gcggcgtgga aatcgaaaaa   420
gtggcggaag aaactccgca cctgatccat aaagttgcgc ttgatccgct gactggcccg   480
atgccgtatc agggacgcga gctggcgttc aaactgggtc tggaaggtaa actggttcag   540
cagttcacca aaatcttcat gggcctggcg accattttcc tggagcgcga cctggcgttg   600
atcgaaatca acccgctggt catcaccaaa cagggcgatc tgatttgcct cgacggcaaa   660
ctgggcgctg acggcaacgc actgttccgc cagcctgatc tgcgcgaaat gcgtgaccag   720
tcgcaggaag atccgcgtga agcacaggct gcacagtggg aactgaacta cgttgcgctg   780
gacggtaaca tcggttgtat ggttaacggc gcaggtctgg cgatgggtac gatggacatc   840
gttaaactgc acggcggcga accggctaac ttccttgacg ttggcggcgg cgcaaccaaa   900
gaacgtgtaa ccgaagcgtt caaaatcatc ctctctgacg acaaagtgaa agccgttctg   960
gttaacatct tcggcggtat cgttcgttgc gacctgatcg ctgacggtat catcggcgcg   1020
gtagcagaag tgggtgttaa cgtaccggtc gtggtacgtc tggaaggtaa caacgccgaa   1080
ctcggcgcga agaaactggc tgacagcggc ctgaatatta ttgcagcaaa aggtctgacg   1140
gatgcagctc agcaggttgt tgccgcagtg gaggggaaat aaaggtccag gcatcaaata   1200
aaacgaaagg ctcagtcgaa agactgggcc tttcgtttta tctgttgttt gtcggtgaac   1260
gctctctact agagtcacac tggctcacct tcgggtgggc ctttctgcgt ttatagctta   1320
tgtcttctac tagtagcggc cgctgcagtc cggcaaaaaa gggcaaggtg tcaccaccct   1380
gccctttttc tttaaaaccg aaaagattac ttcgcgttat gcaggcttcc tcgctcactg   1440
actcgctgcg ctcggtcgtt cggctgcggc gagcggtatc agctcactca aaggcggtaa   1500
tacggttatc cacagaatca ggggataacg caggaaagaa catgtgagca aaaggccagc   1560
aaaaggccag gaaccgtaaa aaggccgcgt tgctggcgtt tttccacagg ctccgccccc   1620
ctgacgagca tcacaaaaat cgacgctcaa gtcagaggtg gcgaaacccg acaggactat   1680
aaagatacca ggcgtttccc cctggaagct ccctcgtgcg ctctcctgtt ccgaccctgc   1740
cgcttaccgg atacctgtcc gcctttctcc cttcgggaag cgtggcgctt tctcatagct   1800
cacgctgtag gtatctcagt tcggtgtagg tcgttcgctc caagctgggc tgtgtgcacg   1860
aacccccgt tcagcccgac cgctgcgcct tatccggtaa ctatcgtctt gagtccaacc   1920
cggtaagaca cgacttatcg ccactggcag cagccactgg taacaggatt agcagagcga   1980
ggtatgtagg cggtgctaca gagttcttga agtggtggcc taactacggc tacactagaa   2040
gaacagtatt tggtatctgc gctctgctga gccagttac cttcggaaaa agagttggta   2100
gctctttgatc cggcaaacaa accaccgctg gtagcggtgg tttttttgtt tgcaagcagc   2160
agattacgcg cagaaaaaaa ggatctcaag aagatccttt gatcttttct acggggtctg   2220
acgctcagtg gaacgaaaac tcacgttaag ggattttggt catgagatta tcaaaaagga   2280
tcttcaccta gatcctttta aattaaaaat gaagttttaa atcaatctaa agtatatatg   2340
agtaaacttg gtctgacagc tcgagtcccg tcaagtcagc gtaatgctct gccagtgtta   2400
caaccaatta accaattctg attagaaaaa ctcatcgagc atcaaatgaa actgcaattt   2460
attcatatca ggattatcaa taccatattt ttgaaaaagc cgtttctgta atgaaggaga   2520
aaactcaccg aggcagttcc ataggatggc aagatcctgg tatcggtctg cgattccgac   2580
tcgtccaaca tcaatacaac ctattaattt ccctcgtca aaaataaggt tatcaagtga   2640
gaaatcacca tgagtgacga ctgaatccgg tgagaatggc aaaagcttat gcatttcttt   2700
ccagacttgt tcaacaggcc agccattacg ctcgtcatca aaatcactcg catcaaccaa   2760
accgttattc attcgtgatt gcgcctgagc gagacgaaat acgcgatcgc tgttaaaagg   2820
acaattacaa acaggaatcg aatgcaaccg gcgcaggaac actgccagcg catcaacaat   2880
attttcacct gaatcaggat attcttctaa tacctggaat gctgttttcc cggggatcgc   2940
agtggtgagt aaccatgcat catcaggagt acggataaaa tgcttgatgg tcggaagagg   3000
cataaattcc gtcagccagt ttagtctgac catctcatct gtaacatcat tggcaacgct   3060
acctttgcca tgtttcagaa acaactctgg cgcatcgggc ttcccataca atcgatagat   3120
tgtcgcacct gattgcccga cattatcgcg agcccattta cccatata aatcagcatc   3180
catgttggaa tttaatcgcg gcctggagca agacgtttcc cgttgaatat ggctcataac   3240
accccttgta ttactgttta tgtaagcaga cagtttattt gttcatgatg atatatttttt   3300
atcttgtgca atgtaacatc agagattttg agacacaacg tggctttgtt gaataaatcg   3360
aactttgct gagttgaagg atcagtcga gtgccacctg acgtctaaga aaccattatt   3420
atcatgacat taacctataa aaataggcgt atcacgaggc agaatttcag ataaaaaaaa   3480
tccttagctt tcgctaagga tgatttctgt aattcgcggc cgcttctaga gactagtgga   3540
agacatggag tttacggcta gctcagtcct aggtatagtg ctagctactt gttagaaaag   3600
agaagcacgt aatgagtagc gtagatattc tggtccctga cctgcctgaa tccgtagccg   3660
atgccaccgt cgcaacctgg cataaaaaac ccggcgacgc agtcgtacgt gatgaagtgc   3720
tggtagaaat cgaaactgac aaagtgataac tggaagtacc ggcatcagca gacggcattc   3780
tggatgcggt tctggaagat gaaggtacaa cggtaacgtc tcgtcagatc cttggtcgcc   3840
tgcgtgaagg caacagcgcc ggtaaagaaa ccagcgccaa atctgaagag aaagcgtcca   3900
ctccggcgca acgccagcag gcgtctctgg aagagcaaaa caacgatgcg ttaagcccgg   3960
cgatccgtcg cctgctggct gaacacaatc tcgacgccaq cgccattaaa ggcaccggtg   4020
tgggtggtcg tctgactcgt gaagatgtgg aaaaacatct ggcgaaagcc ccggcgaaag   4080
```

-continued

```
agtctgctcc ggcagcggct gctccggcgg cgcaaccggc tctggctgca cgtagtgaaa  4140
aacgtgtccc gatgactcgc ctgcgtaagc gtgtggcaga gcgtctgctg gaagcgaaaa  4200
actccaccgc catgctgacc acgttcaacg aagtcaacat gaagccgatt atggatctgc  4260
gtaagcagta cggtgaagcg tttgaaaaac gccacggcat ccgtctgggc tttatgtcct  4320
tctacgtgaa agcggtggtt gaagccctga aacgttaccc ggaagtgaac gcttctatcg  4380
acggcgatga cgtggtttac cacaactatt tcgacgtcag catggcggtt tctacgccgc  4440
gcggcctggt gacgccggtt ctgcgtgatg tcgataccct cggcatggca gacatcgaga  4500
agaaaatcaa agagctggca gtcaaaggcc gtgacggcaa gctgaccgtt gaagatctga  4560
ccggtggtaa cttcaccatc accaacggtg gtgtgttcgg ttccctgatg tctacgccga  4620
tcatcaaccc gccgcagagc gcaattctgg gtatgcacgc tatcaaagat cgtccgatgg  4680
cggtgaatgg tcaggttgag atcctgccga tgatgtacct ggcgctgtcc tacgatcacc  4740
gtctgatcga tggtcgcgaa tccgtgggct tcctggtaac gatcaaagag ttgctggaag  4800
atccgacgcg tctgctgctg gacgtgtagt agtttaagtt tcacctgcac tgtagaccgg  4860
ataaggcatt atcgccttct ccggcaattg aagcctgatg cgacgctgac gcgtcttatc  4920
aggcctacgg gaccaccaat gtaggtcgga taaggcgcaa gcgccgcatc cgacaagcga  4980
tgcctgatgt gacgtttaac gtgtcttatc aggcctacgg gtgaccgaca atgcccggaa  5040
gcgatacgaa atattcggtc tacggtttaa aagataacga ttactgaa            5088
```